(12) United States Patent
Sweeney et al.

(10) Patent No.: US 12,415,284 B2
(45) Date of Patent: Sep. 16, 2025

(54) MOVEABLE DISPLAY SYSTEM

(71) Applicant: Intuitive Surgical Operations, Inc., Sunnyvale, CA (US)

(72) Inventors: Charles A. Sweeney, Manteca, CA (US); Scott O. Luke, San Jose, CA (US); Michael C. Waldo, Los Gatos, CA (US); Allen C. Thompson, Los Altos, CA (US); Randal P. Goldberg, San Mateo, CA (US); Peling G. Lee, Palo Alto, CA (US); Pushkar Hingwe, Los Altos, CA (US); Lawton N. Verner, San Jose, CA (US); Goran A. Lynch, Oakland, CA (US); Russell L. E. Blanchard, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 288 days.

(21) Appl. No.: 17/637,336

(22) PCT Filed: Aug. 21, 2020

(86) PCT No.: PCT/US2020/047494
§ 371 (c)(1),
(2) Date: Feb. 22, 2022

(87) PCT Pub. No.: WO2021/041249
PCT Pub. Date: Mar. 4, 2021

(65) Prior Publication Data
US 2023/0064265 A1 Mar. 2, 2023

Related U.S. Application Data

(60) Provisional application No. 62/890,844, filed on Aug. 23, 2019.

(51) Int. Cl.
*B25J 13/08* (2006.01)
*A61B 34/00* (2016.01)
(Continued)

(52) U.S. Cl.
CPC .............. *B25J 13/088* (2013.01); *A61B 34/25* (2016.02); *A61B 34/35* (2016.02); *A61B 34/74* (2016.02);
(Continued)

(58) Field of Classification Search
CPC ..... B25J 13/088; B25J 9/00; B25J 9/16; B25J 9/0096; B25J 9/1689; B25J 13/02;
(Continued)

(56) References Cited

U.S. PATENT DOCUMENTS 5,748,366 A * 5/1998 Yasunaga ........... G02B 21/0012
359/368
5,876,325 A 3/1999 Mizuno et al.
(Continued)

FOREIGN PATENT DOCUMENTS

CN 108064354 A * 5/2018 ............. G02B 27/01
CN 108194800 A * 6/2018 ........... F16M 11/048
(Continued)

OTHER PUBLICATIONS

Hu, "CN 108194800 A ," Jun. 22, 2018 (Year: 2018).*
(Continued)

*Primary Examiner* — Adam R Mott
*Assistant Examiner* — Byron Xavier Kasper
(74) *Attorney, Agent, or Firm* — IP Spring

(57) ABSTRACT

Implementations relate to a moveable display system. In some implementations, a control unit includes a first support and a second support coupled to the first support. The second support is linearly translatable along a first axis in a first degree of freedom with respect to the first support, and at
(Continued)

least a portion of the second support is linearly translatable along a second axis in a second degree of freedom with respect to the first support. The control unit includes a display unit rotatably coupled to the second support. The display unit is rotatable about a third axis in a third degree of freedom with respect to the second support, and the display unit includes a display device.

20 Claims, 23 Drawing Sheets

(51) Int. Cl.
| | | |
|---|---|---|
| A61B 34/20 | (2016.01) | |
| A61B 34/35 | (2016.01) | |
| A61B 90/00 | (2016.01) | |
| A61B 90/50 | (2016.01) | |
| F16M 11/04 | (2006.01) | |
| F16M 11/08 | (2006.01) | |
| F16M 11/12 | (2006.01) | |
| F16M 11/18 | (2006.01) | |
| F16M 11/20 | (2006.01) | |
| F16M 11/24 | (2006.01) | |
| F16M 11/28 | (2006.01) | |
| G06F 3/01 | (2006.01) | |

(52) U.S. Cl.
CPC ......... *F16M 11/048* (2013.01); *F16M 11/126* (2013.01); *F16M 11/28* (2013.01); *G06F 3/012* (2013.01); *F16M 2200/066* (2013.01)

(58) Field of Classification Search
CPC .. B25J 13/06; B25J 1/12; A61B 34/25; A61B 34/35; A61B 34/74; A61B 34/76; A61B 90/361; A61B 2034/2059; A61B 2034/742; A61B 2090/502; A61B 2090/508; A61B 34/00; A61B 90/50; A61B 90/37; A61B 34/37; A61B 34/30; A61B 1/00042; F16M 11/048; F16M 11/126; F16M 11/28; F16M 2200/066; F16M 11/08; F16M 11/2021; F16M 11/2092; F16M 11/24; F16M 11/18; G06F 3/012
See application file for complete search history.

(56) References Cited

U.S. PATENT DOCUMENTS

| | | |
|---|---|---|
| 8,808,164 B2 | 8/2014 | Hoffman et al. |
| 2003/0090790 A1* | 5/2003 | Metelski ............... A61B 90/25 359/368 |
| 2006/0023324 A1 | 2/2006 | Otsuka et al. |
| 2009/0198136 A1 | 8/2009 | Yanagihara et al. |
| 2010/0039351 A1* | 2/2010 | Nishi ................. F16M 11/2064 345/7 |
| 2010/0187372 A1 | 7/2010 | Smirnov |
| 2013/0140424 A1* | 6/2013 | Frick ................. F16M 11/2092 248/550 |
| 2014/0061425 A1* | 3/2014 | Eoh ..................... F16M 11/2014 248/479 |
| 2015/0208913 A1* | 7/2015 | Watanabe ............. A61B 3/005 351/206 |
| 2016/0183930 A1 | 6/2016 | Herzlinger et al. |
| 2017/0165014 A1* | 6/2017 | Nakanishi ............. A61B 34/74 |
| 2017/0319283 A1 | 11/2017 | Suresh et al. |
| 2018/0353247 A1* | 12/2018 | Ishihara ................ A61B 34/35 |
| 2018/0368656 A1* | 12/2018 | Austin .................. A61B 1/045 |
| 2019/0262089 A1 | 8/2019 | Marshall et al. |
| 2020/0012116 A1* | 1/2020 | Fuerst .................... G06F 3/012 |
| 2020/0064615 A1* | 2/2020 | Ishikawa .............. G02B 21/362 |
| 2020/0405420 A1 | 12/2020 | Purohit et al. |

FOREIGN PATENT DOCUMENTS

| | | |
|---|---|---|
| CN | 207990090 U | 10/2018 |
| EP | 3412240 A1 | 12/2018 |
| JP | S4927235 A | 3/1974 |
| JP | H06315487 A | 11/1994 |
| JP | H10254381 A | 9/1998 |
| JP | 2003180710 A | 7/2003 |
| JP | 2004167259 A | 6/2004 |
| JP | 2006042913 A | 2/2006 |
| JP | 2006346106 A | 12/2006 |
| JP | 2012254305 A | 12/2012 |
| JP | 2018085573 A | 5/2018 |
| JP | 2018202032 A | 12/2018 |
| JP | 2018202134 A | 12/2018 |
| WO | WO-2014028573 A1 | 2/2014 |
| WO | WO-2015142957 A1 | 9/2015 |
| WO | WO-2018075527 A1 | 4/2018 |
| WO | WO-2019120553 A1 * | 6/2019 |

OTHER PUBLICATIONS

Zheng, "CN 108064354 A ," May 22, 2018 (Year: 2018).*
International Search Report and Written Opinion for Application No. PCT/US2020/047501, mailed Dec. 3, 2020, 14 pages.
International Search Report and Written Opinion for Application No. PCT/US2020/047494, mailed Dec. 3, 2020, 15 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

MOVEABLE DISPLAY SYSTEM

CROSS-REFERENCE TO RELATED APPLICATIONS

The present application is a U.S. National Phase application of International Patent Application No. PCT/US2020/047494, filed Aug. 21, 2020 and titled "Moveable Display System," which claims priority to U.S. Provisional Patent Application No. 62/890,844, filed Aug. 23, 2019 and titled "Moveable Display System," the entire contents of both of which are hereby incorporated by reference.

BACKGROUND

Display devices, including display screens, wearable display devices, projectors, etc., are used in a variety of devices and applications. In some applications, a display device outputs images captured by a camera that provide a view of a scene.

In some applications, a display device can be used in conjunction with other devices and allow a user to, e.g., observe a displayed view provided by the display device in conjunction with operating the other devices. For example, in a teleoperated system, a user typically operates a control input device to remotely control (e.g., teleoperate) the motion and/or other functions of a controlled device, such as a manipulator system, at a work site. In some examples, in some teleoperated surgery systems, a user operates a control input device to manipulate surgical instruments and other devices to perform a surgical operation at a surgical site. A control input device often includes hand input devices such as pincher grips, joysticks, exo-skeletal gloves, or the like. In some examples of a surgical or other medical task, a hand input device may control a variety of surgical instruments such as tissue graspers, needle drivers, electrosurgical cautery probes, cameras, etc., which perform functions such as holding or driving a needle, grasping a blood vessel, or dissecting, cauterizing, or coagulating tissue. Other applications can include a variety of telemanipulated tasks performed at a worksite using a teleoperated system.

In various teleoperated systems, a display unit is used in conjunction with the control input device. For example, the display unit can include a display device that displays images depicting a view of a remote work site, or a portion thereof, as captured by a camera at the work site. The display unit can be held by a mechanically-grounded support so that the user can operate the control input device and control a manipulator device to perform tasks at the work site while observing the view of the work site displayed by the display unit. Other systems may also include a display unit that provides a displayed view of a work site to a user without that user using control input devices, e.g., to monitor tasks or events occurring at the work site. In some of these systems, the user can adjust the displayed view by manipulating hand input devices to manipulate a camera, e.g., rotate, pan, and zoom the view of the camera to obtain desired magnification and angles of view of the work site. This allows views of the work site to be customized for more clear presentation, and allows tasks at the work site to be performed accurately based on user-customized views.

However, teleoperated systems may provide a viewing device that has a restrictive viewing area (e.g., the user must peer through viewports or eyepieces) and is static and rigid in its position relative to the user. The user must conform the user's head and body position to the viewing device during system operation to be able to use the viewing device. For example, a user that wishes to look down to view an object closer to the user must adjust his or her eyes downward without tilting his or her head so that the user can continue to view the images in the restrictive viewing area of the viewing device.

Furthermore, manipulation of the displayed view in a viewing device can be challenging to a user of some systems. For example, if the user is grasping hand input devices of a control input device to move manipulator instruments at a work site, adjusting the view in the viewing device may require the user to provide hand input to a control input device and/or enter a different control mode to change the displayed view. Such operation typically requires the user to interrupt and pause manipulation of manipulator instruments to perform view adjustments, thus causing distractions and potential inaccuracies when performing tasks. Furthermore, some hands-free methods of controlling the displayed view, such as eye tracking sensors or voice commands, are often not precise nor reliable, potentially introducing ambiguity to provided commands from the user.

SUMMARY

Implementations of the present application relate to a moveable display system. In some implementations, a control unit includes a first support and a second support coupled to the first support. The second support is linearly translatable along a first axis in a first degree of freedom with respect to the first support, and at least a portion of the second support is linearly translatable along a second axis in a second degree of freedom with respect to the first support. The control unit includes a display unit rotatably coupled to the second support. The display unit is rotatable about a third axis in a third degree of freedom with respect to the second support, and the display unit includes a display device.

In various implementations of the control unit, the first axis is orthogonal to the second axis, and the third axis is orthogonal to the first axis and orthogonal to the second axis. In some implementations, the first support and the second support are fixed in orientation with respect to each other. In some implementations, the first support includes a first telescoping base portion and a second telescoping base portion, the second telescoping base portion is linearly translatable along the first axis with respect to the first telescoping base portion, the second support includes a first telescoping arm portion and a second telescoping arm portion, the second telescoping arm portion is linearly translatable along the second axis with respect to the first telescoping arm portion, and the second telescoping base portion of the first support is rigidly coupled to the first telescoping arm portion of the second support. In some implementations, the second support is coupled to the first support by a middle support, the middle support includes a horizontal portion coupled rigidly to a vertical portion that are orthogonal to each other, the second support is horizontally translatable in the second degree of freedom with respect to the middle support, and the middle support and the second support are vertically translatable in the first degree of freedom with respect to the first support.

In some implementations, the display unit includes a tilt member rotatably coupled to an end of the second support, the tilt member rotatable about the third axis in the third degree of freedom, and the display unit is coupled to and moveable with respect to the tilt member in a fourth degree of freedom. For example, the display unit can be rotatable about a fourth axis with respect to the tilt member in the fourth degree of freedom, the fourth axis orthogonal to the third axis. In some examples, the control unit further comprises an actuator configured to output a force on the display unit about the fourth axis in the fourth degree of freedom. In some implementations, the portion of the second support includes a yoke portion including two yoke members, and the display unit is rotatably coupled to the two yoke members and is positioned between the two yoke members. In some implementations, the control unit includes a first actuator, a second actuator, and a third actuator, the first actuator configured to output first forces on the display unit in the first degree of freedom, the second actuator configured to output second forces on the display unit in the second degree of freedom, and the third actuator configured to output third forces on the display unit in the third degree of freedom. For example, the first actuator, the second actuator, and the third actuator can be configured to output the first forces, the second forces, and the third forces in combination to cause rotation of the display unit about a defined pivot axis.

In some implementations, the display unit includes a head input device provided on the display unit and configured to receive input from a head of a user, and/or a hand input device provided on the display unit and configured to receive input from a hand of a user. In some implementations, the control unit is coupled to a device including a control input device manipulable by a user to control of one or more functions of a teleoperated manipulator system.

In some implementations, a teleoperated system control unit includes a vertical member having a first portion and a second portion, the second portion of the vertical member being linearly translatable along a vertical axis with respect to the first portion of the vertical member; a horizontal member having a first portion and a second portion, the first portion of the horizontal member being rigidly coupled to the second portion of the vertical member and the second portion of the horizontal member being linearly translatable along a horizontal axis with respect to the first portion of the horizontal member; and a display unit rotatably coupled to the second portion of the horizontal member and rotatable about a tilt axis with respect to the horizontal member, the display unit including a display device.

In various implementations of the teleoperated system control unit, the first portion of the vertical member and the second portion of the vertical member are telescopically coupled, and the first portion of the horizontal member and the second portion of the horizontal member are telescopically coupled. In some implementations, a tilt member is coupled to the display unit and rotatably coupled to the second portion of the horizontal member, and the tilt member and display unit are rotatable about the tilt axis. In some implementations, the second portion of the horizontal member includes a yoke portion including two parallel members, the display unit being rotatably coupled to, and positioned between, the two parallel members. In some implementations, the teleoperated system control unit further includes a first actuator, a second actuator, a third actuator, and/or a fourth actuator, the first actuator configured to output first forces on the second portion of the vertical member, the second actuator configured to output second forces on the second portion of the horizontal member, the third actuator configured to output third forces on the display unit about the tilt axis, and the fourth actuator configured to output fourth forces on the display unit about a fourth axis in a fourth degree of freedom in which the display unit is rotatable with respect to the tilt member.

In some implementations, the display unit is rotatable about a defined pivot axis, and the rotation of the display unit about the defined pivot axis is caused by a coordinated combination of linear movement of the second portion of the vertical member, linear movement of the second portion of the horizontal member, and rotational movement of the display unit. For example, the defined pivot axis can be positioned at a location such that the defined pivot axis extends through a neck of a user when the user operates the display unit, can extend through a head input device provided on the display unit at a point configured to contact a forehead of the user that operates the head input device, can be coincident with an eye axis extending through eyes of the user that operates the display unit, or can extend through a hand input device provided on the display unit, e.g., the hand input device configured to be operated by a hand of the user when the user operates the display unit. In some implementations, the display unit is rotatable about a yaw axis with respect to the horizontal member in a fourth degree of freedom, and the yaw axis orthogonal to the tilt axis. In some implementations, the teleoperated system control unit is coupled to a device including a control input device manipulable by a user to control of one or more functions of a teleoperated manipulator system.

In some implementations, a control unit includes a support mechanism and a control system. The support mechanism includes a support linkage that includes a plurality of links, a display unit coupled to the support linkage, and a plurality of actuators coupled to the support linkage. The display unit is moveable in multiple degrees of freedom based on relative movement between the plurality of links, and the display unit includes a display device. The control system is in communication with the support mechanism and is configured to provide control signals to one or more of the plurality of actuators to cause the display unit to rotate about a defined pivot axis. The rotation about the defined pivot axis results from movement of the display unit in at least two of the multiple degrees of freedom.

In various implementations of the control unit, the plurality of links include a tilt member rotatably coupled to a different link of the plurality of links, the tilt member is rotatable about a tilt axis, the display unit is rotatably coupled to the tilt member, and a distance between the defined pivot axis and the tilt axis is fixed during the rotation of the display unit about the defined pivot axis. In various implementations, the multiple degrees of freedom of the support linkage include two or more of a linear first degree of freedom, a linear second degree of freedom, a rotational third degree of freedom, or a rotational fourth degree of freedom. In some examples, the defined pivot axis is: a horizontal axis extending through a neck of a user who operates the display unit, a horizontal axis aligned with an axis extending through eyes of a user who operates the display unit, a horizontal axis aligned with an axis extending through a portion of an input device provided on the display unit, the portion of the input device configured to contact a forehead of a user who operates the display unit, or a horizontal axis aligned with an axis extending through portion of a hand input device provided on the display unit, the hand input device configured to be operated by a hand of a user who operates the display unit and the hand input device. In further examples, the defined pivot axis is adjustable in space based on user input to the control unit.

In some implementations, the control system is configured to provide the control signals to control the actuators to move the display unit about the defined pivot axis to follow movement of a head of a user who operates the control unit. In some example implementations, the display unit is not attached to the head of the user. In some implementations, the control system is in communication with a control input device, and is configured to receive commands from the control input device and send signals based on the commands to a teleoperated manipulator system.

In some implementations, a control unit includes a support, a curved track coupled to the support, and a display unit coupled to the curved track, the display unit including a display device and guided by the curved track to be rotatable about a yaw axis in a rotary degree of freedom. In some implementations, the display unit is movable left or right along the curved track with respect to a user who operates the display unit, the yaw axis extending vertically with respect to the user. In some implementations, the support includes a linkage having a plurality of links moveable with respect to each other, the plurality of links enabling the display unit to move in at least one additional degree of freedom, and an actuator is coupled to the display unit and is configured to output force in the rotary degree of freedom that causes the display unit to move in the rotary degree of freedom. In some examples, the display unit can be rigidly coupled to the curved track and the curved track is slidably coupled to the support, or the display unit can be slidably coupled to the curved track and the curved track is rigidly coupled to the support.

In some implementations, a method includes receiving first user input at a first input device and causing movement of a display unit in one or more degrees of freedom provided by a support linkage coupled to the display unit. The display unit includes a display device. The movement is based on the first user input, and causing the movement includes causing a second link of the support linkage to linearly translate with respect to a first link of the support linkage along a first axis in a first degree of freedom; causing a portion of the second link to linearly translate with respect to the first link along a second axis in a second degree of freedom; and causing the display unit to rotate about a third axis in a third degree of freedom with respect to the second link.

In some implementations, the first user input is received from at least one of a head input device provided on the display unit that receives input from a head of a user, and/or a hand input device provided on the display unit that receives input from a hand of the user. In some implementations, causing the movement of the display unit includes causing the display unit to rotate about a fourth axis with respect to the second link in a fourth degree of freedom, the fourth axis being orthogonal to the third axis. In some implementations, the method includes receiving second user input at a second input device (e.g., that is coupled to the support linkage), and, based on the second user input, controlling an instrument actuator to move a manipulator instrument in space. For example, the display unit can display a view of a workspace in which the manipulator instrument operates. In some implementations, the method further includes updating images displayed by the display device of the display unit in accordance with the first user input (or otherwise in accordance with the movement of the display unit). In some implementations, the method includes causing a actuator of a manipulator system to move an image capture device of the manipulator system in accordance with the first user input, and image data is received from the image capture device and displayed by the display device of the display unit.

In some implementations, a control unit includes means for receiving first user input at a first input device, means for causing, based on the first user input, of a display unit movement in one or more degrees of freedom provided by a support linkage coupled to the display unit. The display unit includes a display device. The means for causing the movement of the display unit includes means for causing a second link of the support linkage to linearly translate with respect to a first link along a first axis in a first degree of freedom, means for causing a portion of the second link to linearly translate with respect to the first link along a second axis in a second degree of freedom, and means for causing the display unit to rotate about a third axis in a third degree of freedom with respect to the second link. In some implementations, the control unit further comprises means for receiving second user input, and means for controlling a slave instrument actuator, based on the second user input, to move a slave instrument in space.

DETAILED DESCRIPTION

Figure 1:
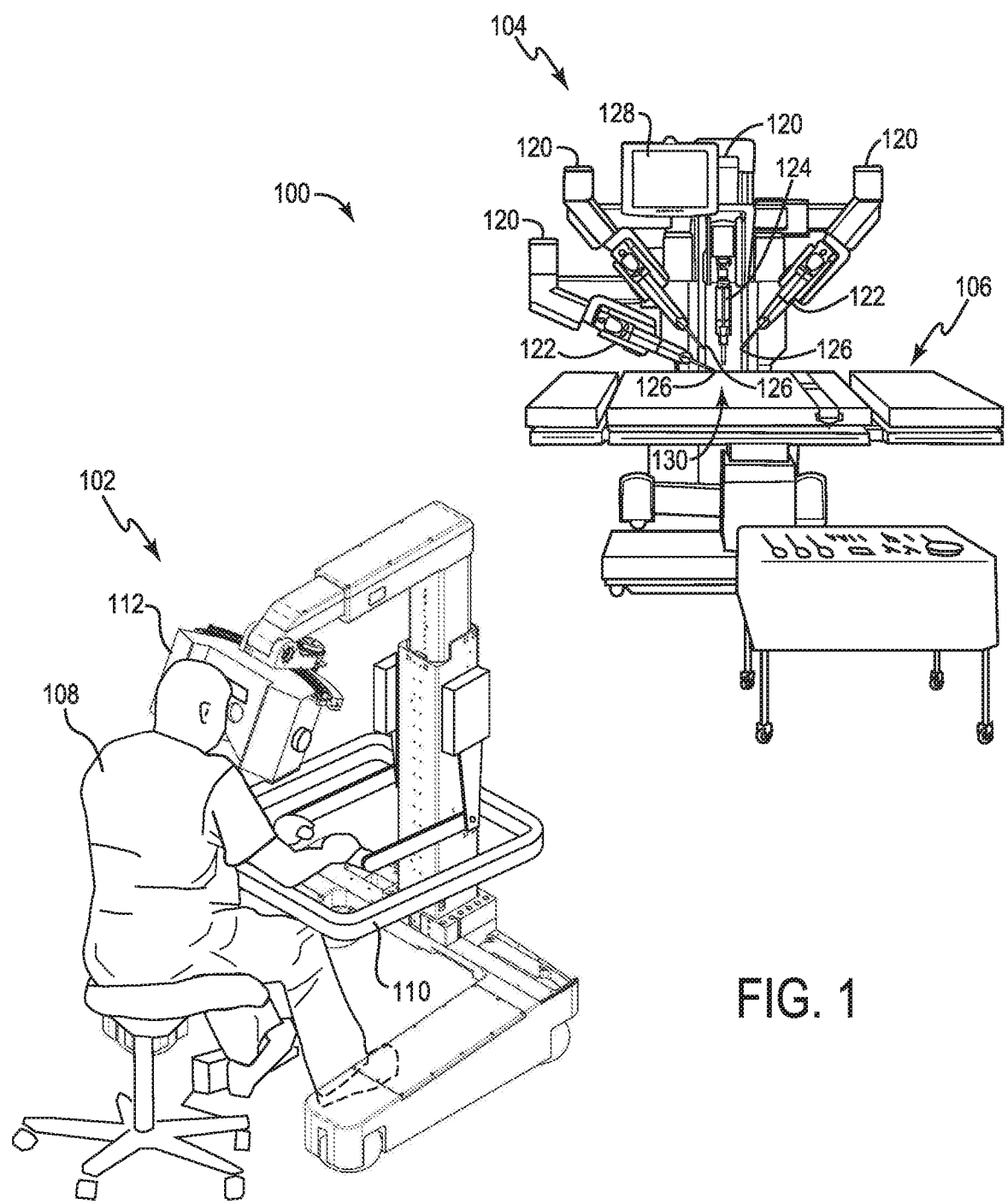
FIG. 1 is a diagrammatic view of an example teleoperated surgical system including a control input device, display system, and manipulator device, according to some implementations.

Implementations relate to a moveable display system that accommodates and/or is responsive to user viewing. For example, in some implementations, the display system is used in a user control system to provide a displayed view of a work site or environment to a user while the user operates one or more other devices, such as a control input device of a teleoperated system. As described in more detail herein, implementations provide a display system that is responsive to the user's motions to move a viewed display unit in ways that accommodate and/or follow user head motion. In various examples, the display system can include a display unit that displays images and is mechanically grounded, allowing the user to manipulate other devices, such as hand-operated and/or foot-operated control input devices, while viewing the output of the display unit. Some implementations can provide various views of a work site by the display unit via camera images that are responsive to user input provided via the display system.

Described features of the display system include a support linkage providing multiple degrees of freedom to the display unit. The support linkage includes a first (e.g., vertical) support having a first portion and a second portion, and the second portion is linearly translatable along a vertical axis with respect to the first portion (e.g., telescoping portions). The support linkage includes a second (e.g., horizontal) support rigidly coupled to the vertical support and having a first portion and a second portion, and the first portion is rigidly coupled to the second portion of the vertical member and the second portion is linearly translatable along a horizontal axis with respect to the first portion (e.g., telescoping portions). In some implementations, the support linkage includes a tilt member rotatably coupled to a distal end of the second support, the tilt member rotatable about a third axis in a third degree of freedom. In some implementations, a display unit is coupled to the tilt member. In some implementations, the display unit is moveable with respect to the tilt member in a fourth degree of freedom, e.g., rotational movement about a fourth (yaw) axis. Actuators such as motors are coupled to one or more of these components to allow a control system to move the components and thereby move the display unit in a workspace in particular degrees of freedom. User input devices on the display unit allow the user to provide user input to direct the movement, e.g., change in position and orientation, of the display unit. The display system can be used in conjunction with a control input device that provides control signals to a manipulator system in a teleoperated system to control manipulator system functions, e.g., movement and other functions of manipulator instruments.

Described features provide various benefits. For example, the support linkage and actuators allow the display system to change the position and orientation of the display unit based on received user input, e.g., to accommodate changes in angle and motion of the user's head and eyes or to respond to commands input by the user's hands, head, eyes, etc. For example, the display unit can be rotated about a defined pivot axis that can coincide with the user's eyes or coincide with a pivot axis of the user's neck, thus providing motion of the display unit that is aligned with the user's natural body motions. These features allow the user to easily re-orient the display unit during procedures to obtain different comfortable viewing angles and to reduce the physical constraints of using the display unit, thus decreasing fatigue of the user in associated procedures. The motion of display unit in the provided tilt, horizontal, and vertical degrees of freedom, e.g., providing motion about a defined pivot axis and a yaw axis, allows the display unit to follow and stay close to the user's head and/or eyes (e.g., movement of the display unit mirrors or copies movement of the user's head and/or eyes) during user head motion, and/or to maintain a physical connection between the user's forehead and the display unit. In some implementations, this allows the display unit to follow movement of a user's head and eyes without having to physically attach the display unit to the user's head, thus avoiding user irritation and fatigue from such attachment.

Furthermore, the defined pivot axis of the display unit can be a virtual axis that need not be confined to physical axes of motion of the mechanical components of the display system. This allows the location of the defined pivot axis to be adjusted for various use conditions and/or customized for a particular user, e.g., to accommodate a particular user's height, arm reach, size of neck or head, etc., to allow greater comfort in operating the display system. Furthermore, sensors such as head sensors on the display unit allow the user to easily provide user input without using hands that may be manipulating other input devices such as a control input device.

In addition, changes in the position and/or orientation of the display unit, directed by user input, can be used to modify the display of images by the display unit. For example, a displayed image or user interface can be scrolled, tilted, panned, or zoomed based on corresponding received user input to the display device that also direct the display unit to perform similar or corresponding motions. In some implementations, functions of an image capture device (or other instrument or device) at a remote work site are manipulated based on the user input to the display unit, e.g., movement of the image capture device or other device functions such as panning, tilting, and zooming. Head sensors on the display unit allow the user to provide such user input without having to interrupt or pause a teleoperated procedure using other user input devices such as a control input device operated by hand or foot.

Various terms including "linear," "center," "parallel," "orthogonal," "perpendicular," "aligned," "horizontal," "vertical," or particular measurements or other units as used herein can be approximate, need not be exact, and can include typical engineering tolerances.

Some implementations herein may relate to various instruments and portions of instruments in terms of their state in three-dimensional space. As used herein, the term "position" refers to the location of an object or a portion of an object in a three dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw around the Cartesian X, Y, and Z axes). As used herein, the term "pose" refers to the position of an object or a portion of an object in at least one degree of translational freedom and to the orientation of that object or portion of the object in at least one degree of rotational freedom (up to six total degrees of freedom).

As referred to herein, a mechanically grounded unit or device is constrained with respect to possible position and orientation motion in a large working environment (e.g., an operating area or room). Also, such a unit is kinematically coupled to the ground (e.g., mechanically supported by a console, supports, or other object attached to the ground). As used herein, the term "proximal" refers to an element that is close to (or closer to) a mechanical ground and the term "distal" refers to an element that is away from (or further from) a mechanical ground.

Various features described herein can be used to augment the control capability of a computer-assisted teleoperated system. In some implementations, the teleoperated system includes one or more control input devices (e.g., one, two, three, or more) for providing manipulator instrument control in various procedures (surgical, procedures in extreme environments, or other procedures), instruction, supervision, proctoring, and other feedback to a user of the system.

FIG. 1 is a diagrammatic view of an example teleoperated surgical system 100, which can be used with one or more features disclosed herein. As shown, teleoperated surgical system 100 may include a user control system (e.g., console or workstation) 102 and a manipulator system 104.

Figure 2:
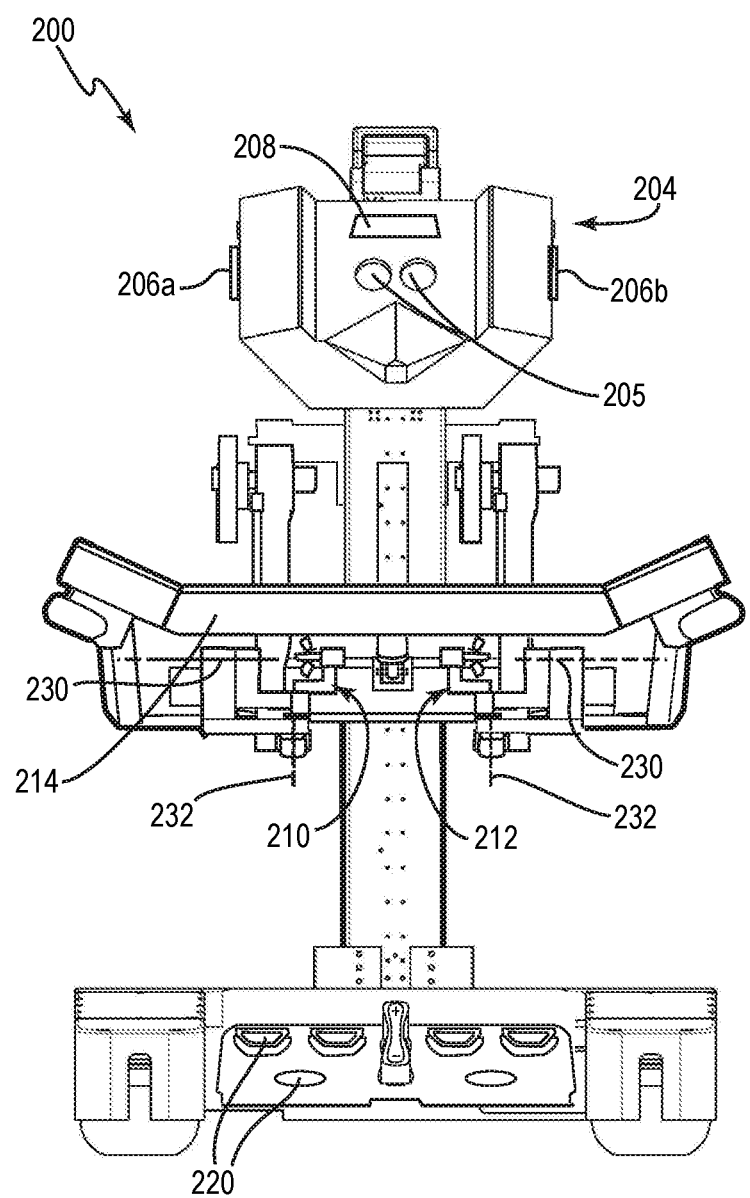
FIG. 2 is a front view of a user control system including control input devices and a display system, according to some implementations.
Figure 40:
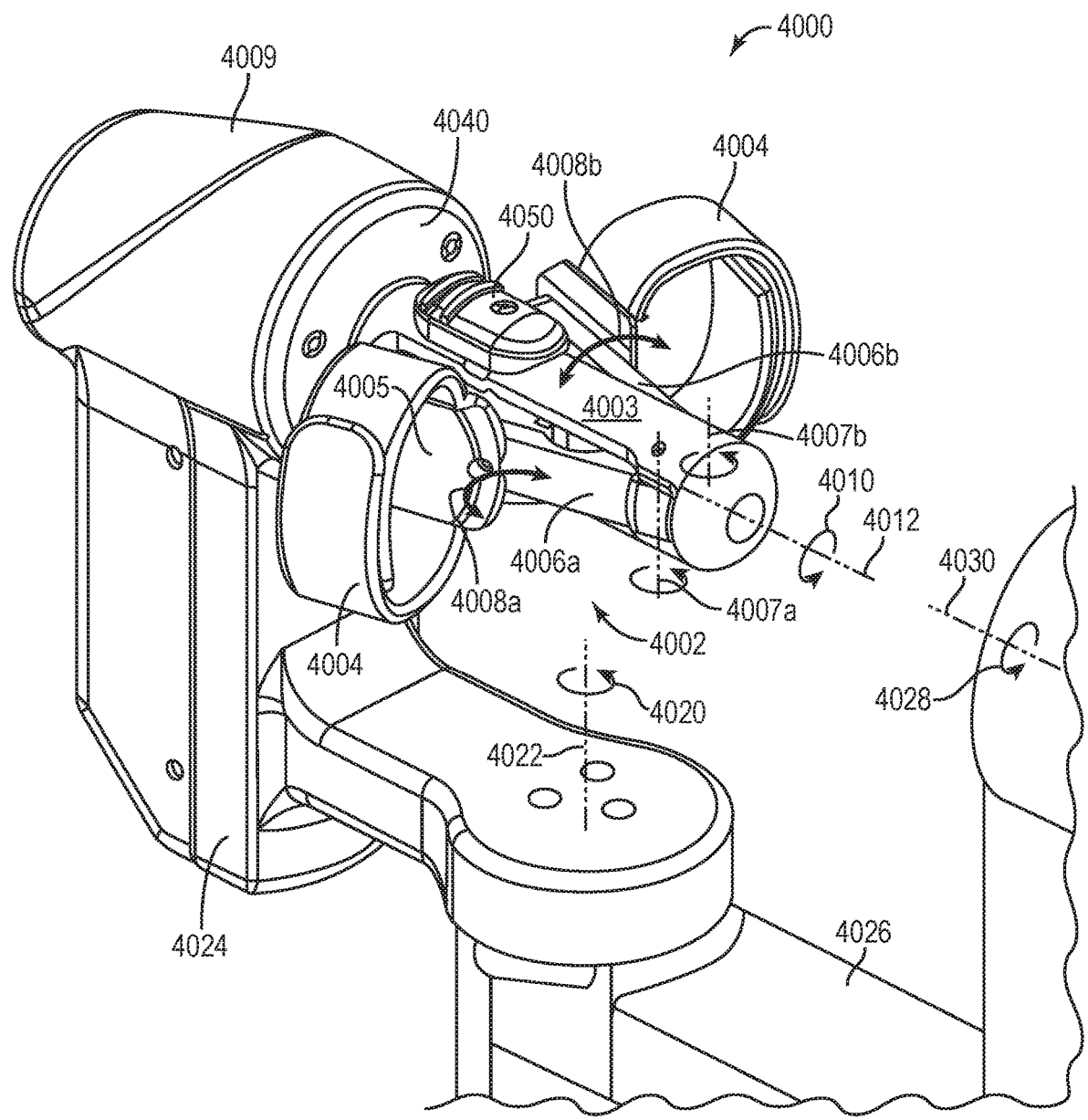
FIG. 40 is a perspective view of an example portion of a control input device that can be used with the described display systems, according to some implementations.

In this example, the user control system 102 includes one or more control input devices which are contacted and manipulated by the user's hands, e.g., one control input device for each hand. FIGS. 2 and 40 show some example implementations of control input devices which are described in greater detail below. The control input devices are supported by the user control system 102 and can be mechanically grounded. An ergonomic support 110 (e.g., forearm rest) can be provided in some implementations, on which user 108 can rest his or her forearms while grasping control input devices. For example, the control input devices can be positioned in a workspace disposed inwardly (away from user 108) beyond the support 110. In some examples, the user 108 may perform surgical tasks at a work site near the manipulator system 104 during a surgical procedure by controlling the manipulator system 104 using the control input devices.

A display unit 112 is included in the user control system 102. Display unit 112 can display images for viewing by the user 108. For example, the images can be displayed by a display device in the display unit, such as one or more display screens, projectors, or other devices. The display unit 112 can be moved in various degrees of freedom to accommodate the user's viewing position and/or to provide control functions, as described in greater detail below. In the example of the teleoperated system 100, displayed images can depict a work site at which the user is performing various tasks via control of the control input devices. In some examples, the images displayed by the display unit 112 can be received by the user control system 102 from one or more image capture devices arranged at a remote work site. In other examples, the images displayed by the display unit can be generated by the display unit (or by a connected other device or system). In an example of a surgical procedure using teleoperated system 100, the display unit 112 can display images of a physical surgical site at a patient near the manipulator system 104, or a generated virtual representation of a surgical site or a combination of physical and virtual sites (e.g., augmented reality), and can display real or virtual instruments of the manipulator system 104 controlled by the control input devices of user control system 102. Display unit 112 can provide a two dimensional image and/or a three-dimensional image of, for example, an end effector of a manipulator instrument 126 and the surgical site. A three-dimensional image can provide three-dimensional depth cues to permit user 108 to assess relative depths of instruments and patient anatomy and to use visual feedback to steer the manipulator instruments 126 using control input devices to precisely target and control features.

When using the user control system 102, the user 108 can sit in a chair or other support in front of the user control system 102, position his or her eyes in front of the display unit 112 (and/or move the display unit 112 to a position/orientation of his or her eyes), grasp and manipulate the control input devices, e.g., one in each hand, and rest his or her forearms on the ergonomic support 110 as desired. In some implementations, the user can stand at the user control system or assume other poses, and the display unit 112 and control input devices can be adjusted in position (height, depth, etc.) to accommodate various user body poses and individual user preferences.

The teleoperated system 100 may also include manipulator system 104 which can be controlled by the user control system 102. In this example, the manipulator system 104 is mounted to or near an operating table 106 (e.g., table, bed, or other support) on which a patient may be positioned. A work site 130 can be provided on the operating table 106, e.g., on or in a patient, simulated patient or model, etc. (not shown). In other implementations, a work site can be a different site or area at which tasks are to be performed using a manipulator system. The teleoperated manipulator system 104 includes a plurality of manipulator arms 120, each coupled to an instrument assembly 122. An instrument assembly 122 may include, for example, an instrument 126. In some examples, instruments 126 may include surgical instruments. In some implementations, a surgical instrument can include a surgical end effector at its distal end, e.g., for treating tissue of a patient.

In various implementations, one or more of the instruments 126 can include image capture devices (e.g., cameras), such as a camera included in an endoscope assembly 124, which can provide captured images of a portion of the work site (e.g., a region or portion of a patient in which a surgical task is being performed). In some implementations, captured images can be transmitted to the display unit 112 of the user control system 102 for output. In some implementations, a display device 128 can be included on the manipulator system 104 to display captured images and/or other information related to a procedure being performed at the work site. In some implementations, an image capture device can be moved in multiple degrees of freedom, e.g., based on translation and rotation of portions of a manipulator arm 120 holding the camera.

In an example of a surgical procedure using the teleoperated system 100, the manipulator system 104 can be positioned close to a patient (or simulated patient) for surgery, where it can remain stationary until a particular surgical procedure or stage of a procedure is completed. In various implementations, the user control system 102 can be positioned in various locations relative to the manipulator system 104, e.g., in a sterile surgical field close to manipulator system 104 and the work site 130, in the same room as the manipulator system 104 and work site 130, or remotely from the manipulator system 104 and work site 130, e.g., in a different room, building, or other geographic location. The number of teleoperated instruments 126 used at one time, and/or the number of arms 120 used in manipulator system 104, may depend on the procedure to be performed and the space constraints within the available area, among other factors.

In some implementations, the manipulator arms 120 and/or instrument assemblies 122 may be controlled to move and articulate the instruments 126 in response to manipulation of control input devices by the user 108, so that the user 108 can perform tasks at the work site 130. For example, the user can direct surgical procedures at internal surgical sites through minimally invasive surgical apertures. In some implementations, one or more actuators coupled to the manipulator arms 120 and/or instrument assemblies 122 may output force to cause links or other portions of the arms 120 and/or instruments 126 to move in particular degrees of freedom in response to control signals received from the control input devices.

Some implementations of the teleoperated system 100 can provide different modes of operation. In some examples, in a non-controlling mode (e.g., safe mode) of the teleoperated system 100, the controlled motion of the manipulator system 104 is controllably decoupled (disconnected) from the control input devices in disconnected configuration, such that movement and other manipulation of the control input devices do not cause motion of the manipulator system 104. In a controlling mode of the teleoperated system 100 (e.g., following mode), motion of the manipulator system 104 can be controllably coupled (connected) to the control input devices such that movement and other manipulation of the control input devices causes motion of the manipulator system 104, e.g., during a surgical procedure. For example, each manipulator arm 120 and the teleoperated instrument assembly 122 controlled by that arm 120 may be controllably coupled to and decoupled from one or more control input devices to allow control over movement and/or other functions of that arm.

In some examples, the control over manipulator systems enables the user to direct surgical procedures at internal surgical sites through minimally invasive surgical apertures. For example, one or more actuators coupled to the manipulator arms 120 can output force to cause links or other portions of the arms to move in particular degrees of freedom in response to control signals provided by the control input devices. The control input devices can be used within a room (e.g., an operating room) that also houses the manipulator system and worksite (e.g., within or outside a sterile surgical field close to an operating table), or can be positioned more remotely from the manipulator system, e.g., at a different room, building, or other location than the manipulator system.

In some implementations, a control system (not shown in FIG. 1) is provided in user control system 102 and/or is provided externally to the user control system 102 (e.g., in communication with the user control system). As the user 108 moves control input device(s), sensed spatial information and sensed orientation information is provided to the control system based on the movement of the control input devices. Other user input is also provided to the control system, e.g., user input received at the display unit 112, and/or activation of other input devices. The control system can provide control signals to the manipulator system 104 to control the movement of arms 120, instrument assemblies 122, and instruments 126 based on the received information and user input. For example, the control system can map sensed spatial motion data and sensed orientation data describing the control input devices in space to a common reference frame. The control system may process the mapped data and generate commands to appropriately position an instrument 126, e.g., an end effector or tip, of manipulator system 104 based on the movement (e.g., change of position and/or orientation) of one or more control input devices. The control system can use a teleoperation servo control system to translate and to transfer the sensed motion of the control input devices to an associated arm 120 of the manipulator system 104 through control commands so that user 108 can manipulate the instruments 126 of the manipulator system 104. The control system can similarly generate commands based on activation or manipulation of input controls of the control input devices to perform other functions of the manipulator system 104 and/or instruments 126, e.g., move jaws of an instrument end effector, activate a cutting tool or output energy, activate a suction or irrigation function, etc. In some implementations, the control system can similarly generate commands based on activation or manipulation of input controls of the display unit 112 to perform other functions of the manipulator system 104 and/or instruments 126. In one embodiment, the control system supports one or more wireless communication protocols such as Bluetooth, IrDA, HomeRF, IEEE 802.11, DECT, and Wireless Telemetry. Some examples of a control system are described below with respect to FIG. 34.

In some implementations, the display unit 112 can be operated by a user in conjunction with the operation of one or more ungrounded control input devices, which are control input devices that are not kinematically grounded, e.g., control input devices held by the user's hands without additional support. For example, the user can sit or stand and view images in display unit 112 while grasping and manipulating ungrounded control input devices in his or her hands. Some examples of an ungrounded control input device are disclosed in U.S. Pat. No. 8,521,331 B2 (issued on Aug. 27, 2013, titled "Patient-side Surgeon Interface For a Minimally Invasive, Teleoperated Surgical Instrument"), which is incorporated herein by reference in its entirety. In some implementations, the user can use display unit 112 that is positioned near to the work site such that the user can operate manual surgical instruments at the work site, such as a laparoscopic instrument or a stapler, while viewing images displayed by the display unit 112.

In some implementations, the teleoperated system 100 may also include one or more additional input systems which allow additional users to provide input to the system. For example, a second (or third, etc.) display unit 112 can be used by an additional user to monitor and/or assist the procedure. A second user control system 102 can be provided for use by a second user, e.g., for training, to alternate control or provide simultaneous control of the manipulator system 104, etc. Additional ungrounded control input devices, side carts with display devices, and other components can be used in the teleoperated system 100.

In some implementations, a virtual representation of manipulator system 104 can be controlled instead of the physical manipulator system 104, e.g., presented in a graphical training simulation provided by a computing device coupled to the teleoperated system 100. For example, a user can manipulate control input devices to control a displayed representation of an end effector in virtual space of the simulation, similarly as if the end effector were a physical object coupled to a physical manipulator system. Some implementations can use control input devices in training, e.g., demonstrate the use of instruments and controls of a user control system including control input devices.

In some implementations, non-teleoperated systems can also use one or more features of the user control system and/or display unit 112 as described herein. For example, various types of control systems and devices, peripherals, etc. can be used with described display unit systems. In some examples, display unit 112 can be used in some non-teleoperated systems, e.g., to view a remote work site or physical scene at which the user does not manipulate a manipulator system, to view a displayed virtual environment unrelated to a physical manipulator system or physical work site, etc. In some of these systems, the user control system 102 and manipulator system 104 can be omitted and the display unit 112 can be used in a standalone display system.

Some implementations can include one or more components of a teleoperated medical system such as a da Vinci® Surgical System (e.g., a Model IS3000 or IS4000, marketed as the da Vinci® Si® or da Vinci® Xi® Surgical System), commercialized by Intuitive Surgical, Inc. of Sunnyvale, California. Features disclosed herein may be implemented in various ways, including in implementations at least partially computer-controlled, controlled via electronic control signals, manually controlled via direct physical manipulation, etc. Implementations on da Vinci® Surgical Systems are merely examples and are not to be considered as limiting the scope of the features disclosed herein. For example, different types of teleoperated systems having manipulator systems at work sites can make use of features described herein. Other, non-teleoperated systems can also use one or more described features, e.g., various types of control systems and devices, peripherals, etc.

FIG. 2 is a front elevational view of an example user control system 200 including control input devices and a display system, according to some implementations. For example, user control system 200 can be similar to the user control system 102 described for FIG. 1.

User control system 200 includes display unit 204 which can, for example, display images during a procedure implemented by the teleoperated system 100 similarly as described for display unit 112 of FIG. 1. The images can be captured by an image capture device and depict a physical work site at which a task is performed, such as a surgical site displayed during a surgical procedure, or can depict a generated representation of a virtual work site. The display unit 204 can also display other information, such as a graphical user interface allowing selection of commands and functions, status information, alerts and warnings, notifications, etc. Such information can be displayed in combination with (e.g., overlaid on) a view of a work site, or without a work site view.

In the example shown, the display unit 204 includes two viewports 205. A user can position the user's head such that the user's eyes are aligned with the viewports 205 to view images displayed by the display unit 204. Furthermore, as described herein, display unit 204 is moveable (translatable and/or rotatable) within a defined workspace based on user input such that the user can align the viewports of the display unit and a viewing angle of the display unit with the user's eyes. In some examples, one or more display screens can be provided behind the viewports which display images to the viewing user. In some implementations, one or more display screens or other display devices can be used instead of viewports 205. The display unit 204 is connected to a support mechanism and can be moved in one or more degrees of freedom, examples of which are described in greater detail below.

In some implementations, the user control system 200 includes one or more input control devices to allow a user to adjust or otherwise manipulate the position and/or orientation of the display unit 204 with respect to the other portions of the user control system 200 (e.g., with respect to control input devices 210 and 212, described below). In this example, a hand input device 206a is positioned on the left side of the display unit 204 and a hand input device 206b on the right side of the display unit 204. In some implementations, the hand input devices 206a and 206b can receive user input to cause the display unit 204 to change its orientation and/or position, e.g., to provide ergonomic adjustments for more user comfort. Such hand input devices can alternatively or additionally be positioned at other areas or components of the user control system 200. Examples of hand input devices 206a and 206b are described in greater detail below.

In some implementations, a head input device 208 is positioned on a side of the display unit 204 that is facing the user. Head input device 208 can sense a user's head (e.g., forehead), e.g., sense presence and/or contact with the user's head, as user input to cause the display unit 204 to be moved in accordance with the user input, e.g., change the orientation and/or position of the display unit 204. Additionally or alternatively, the control system can command one or more components, changes in state, or processes of the user control system 102 and/or manipulator system 104 in accordance with the user input to head input device 208. Examples of head input device 208 are described in greater detail below.

Two control input devices 210 and 212 are provided in user control system 200 for user manipulation. For example, a user can rest the user's forearms on an ergonomic support 214 while gripping portions of the two control input devices 210 and 212, with one control input device in each hand (e.g., the control input devices 210 and 212 can be moved to positions above the support 214 and/or the support 214 can be moved to positions lower than the control input devices 210 and 212). In some implementations, ergonomic support 214 can be adjustable in height for different users. The user also positions the user's head to view the display unit 204 as described above while manipulating the control input devices 210 and 212. The control input devices may include one or more of any number of a variety of input devices manipulable by the user, such as kinematically linked (mechanically grounded) hand grips, joysticks, trackballs, data gloves, trigger-guns, hand-operated controllers, voice recognition devices, touch screens, and the like.

In some implementations, each control input device 210 and 212 can include grip portions that are moveable in a plurality of degrees of freedom. For example, each control input device 210 and 212 can control motion and functions of an associated arm assembly 120 of the manipulator system 104 shown in FIG. 1. In some examples, control input device 210 can be moved in a plurality of degrees of freedom to move one corresponding end effector 126 of the manipulator system 104 in corresponding degrees of freedom, and control input device 212 can be moved in a plurality of degrees of freedom to move a different corresponding end effector 126 of the manipulator system 104 in corresponding degrees of freedom. In some implementations, the control input devices 210 and 212 are provided with the same degrees of freedom as the instruments 126 of the manipulator system to provide the operator with telepresence, e.g., the perception that the control input devices are integral with the instruments so that the operator has a strong sense of directly controlling instruments as if present at the work site. In other implementations, the control input devices 210 and 212 may have more or fewer degrees of freedom than the associated instruments 126. In some implementations, the control input devices are manual input devices which move in all six Cartesian degrees of freedom, and which may also include an actuatable grip portion (e.g., handle) for actuating manipulator instruments, e.g., for closing grasping jaws, applying an electrical potential to an electrode, delivering a medicinal treatment, and the like. In some implementations, a grip function, such as moving two grip portions of a control input device together and apart in a pincher movement, can provide an additional mechanical degree of freedom (i.e., a grip DOF). In some example implementations, control input devices 210 and 212 may provide control of one or more surgical instruments 126 in a surgical environment or proxy surgical instruments in a virtual environment. Examples of some implementations of a control input device are described with respect to FIG. 32.

Some implementations of user control system 200 can include one or more foot controls 220 positioned below the control input devices 210 and 212. The foot controls 220 can be depressed, slid, and/or otherwise manipulated by a user's feet to input various commands to a control system of a teleoperated system while the user is operating the user control system 200. In some implementations, foot controls 220 or other controls can be considered "control input devices" that can control one or more functions or operations of the manipulator system 104.

In some implementations, one or more user presence sensors can be positioned at one or more locations of the user control system 200 to detect the presence of a user operating the user control system 200 and/or located next to or near to the user control system 200. For example, user presence sensors can be positioned on display unit 204 and sense a presence of a user's head aligned with the viewports 205. For example, an optical sensor can be used for a presence sensor, where the optical sensor includes an emitter and a detector and an interruption of an optical beam is sensed by the detector when the user's head is positioned to view the output of the display unit 204 and the user is in a proper position to use the control input devices 210 and 212. In some implementations, hand input devices 206 and/or head input device 208 can be used to sense user presence. Additional or alternative types of presence sensors can be used in various implementations.

Figure 3:
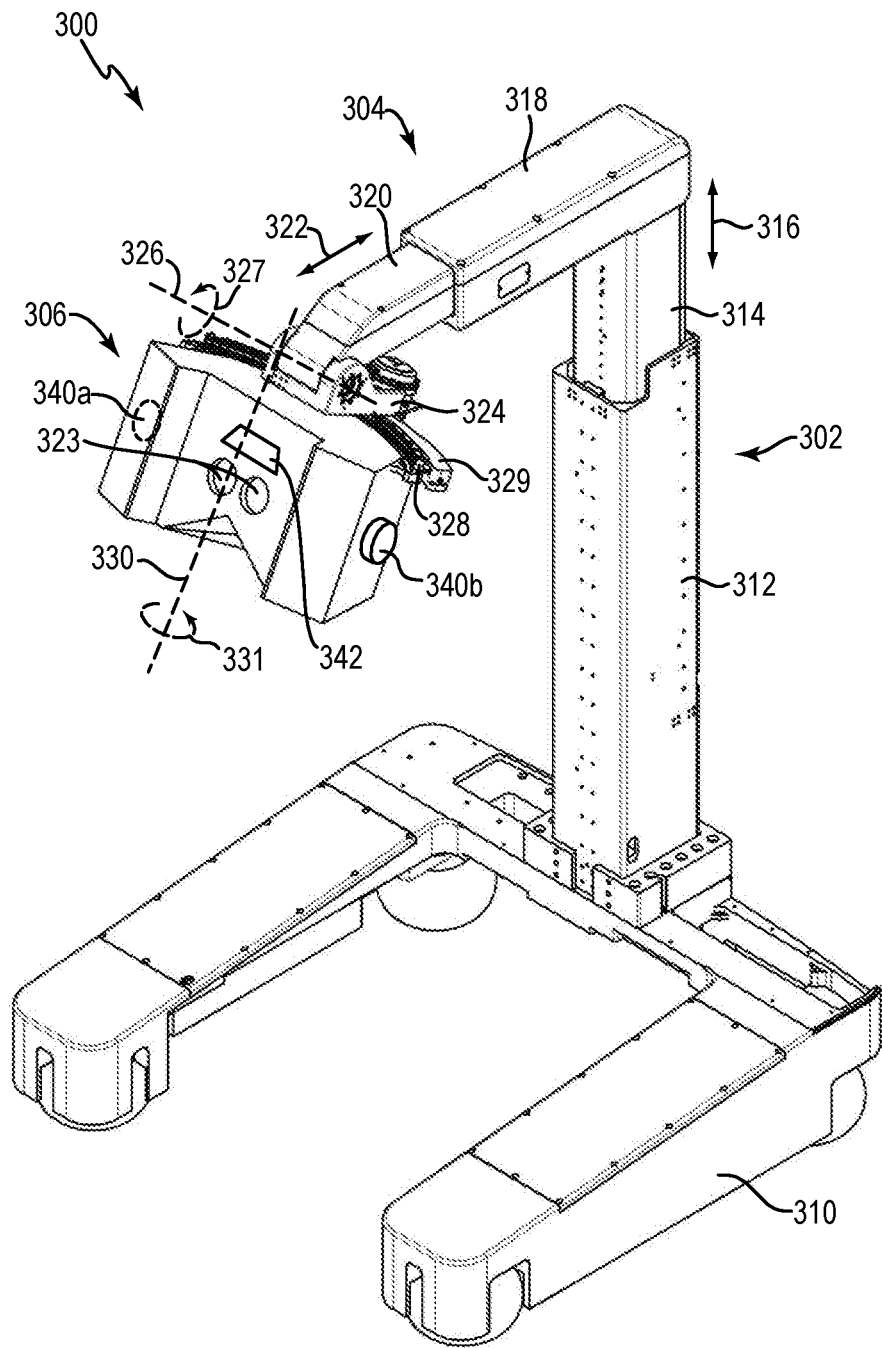
FIGS. 3-5 are perspective, front, and side views, respectively, of an example display system, according to some implementations.
Figure 4:
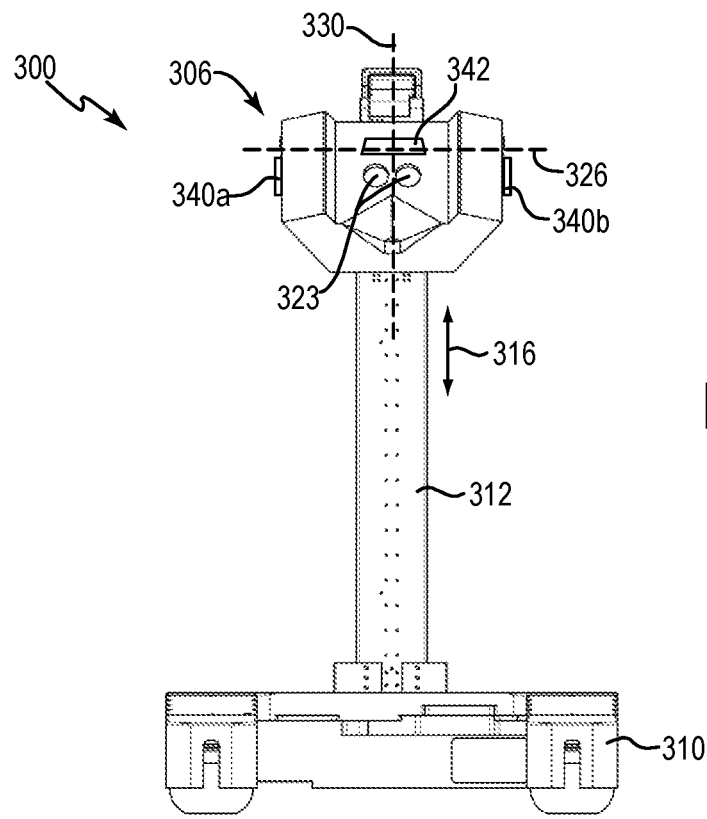
Figure 5:
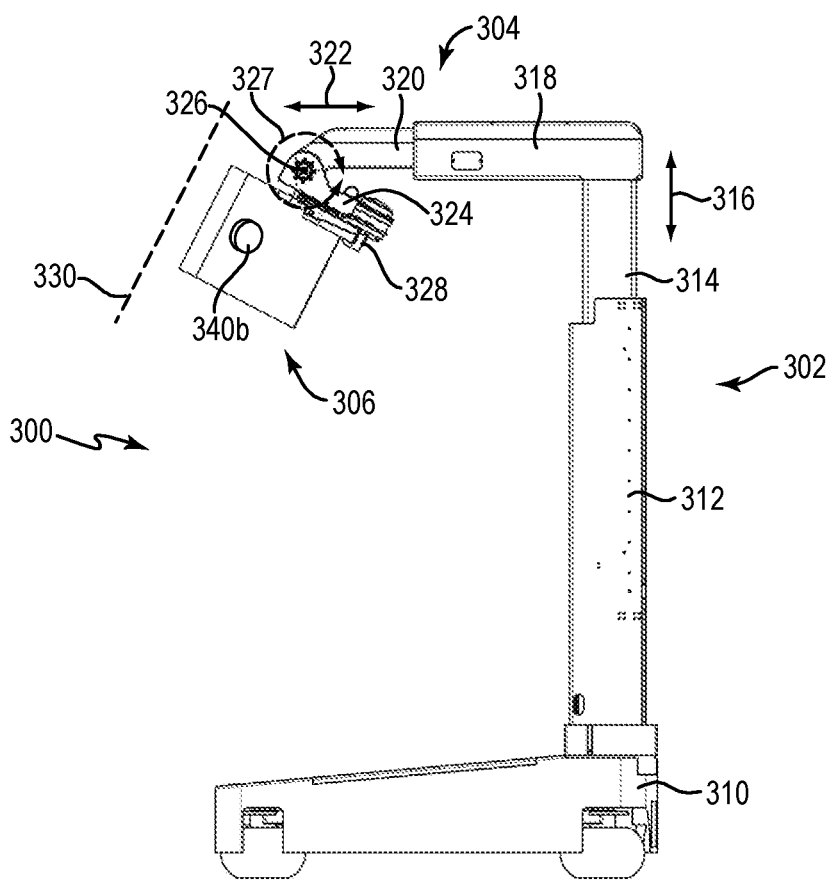

FIG. 3 is a perspective view, FIG. 4 is a front view, and FIG. 5 is a side view of an example display system 300, according to some implementations. In some examples, display system 300 can be used in a user control system of a teleoperated system, e.g., user control system 102 of teleoperated surgical system 100 of FIG. 1, or can be used in other systems or as a standalone system, e.g., to allow a user to view a work site or other physical site, a displayed virtual environment, etc.

Display system 300 includes a base support 302, an arm support 304, and a display unit 306. As described in greater detail below, display unit 306 is provided with multiple degrees of freedom of movement provided by a support linkage including base support 302, arm support 304 coupled to the base support 302, and a tilt member 324 (described below) coupled to the arm support 304. Display unit 306 is coupled to the tilt member.

Base support 302, in this example, is a vertical member that is mechanically grounded, e.g., coupled to ground. For example, base support 302 can be mechanically coupled to a support structure 310 that is coupled to (e.g., resting on) the ground to provide stability to the base support 302. Base support 302 includes a first base portion 312 and a second base portion 314. The first base portion 312 is a proximal portion of the base support 302 that can be mechanically grounded, and the second base portion 314 is a distal portion of the base support 302 that is linearly coupled to the first base portion 312 such that the second base portion 314 is translatable with respect to the first base portion 312 in a linear degree of freedom. In some examples, first base portion 312 and second arm portion 314 are telescopically coupled, e.g., first base portion 312 is a first telescoping base portion and second base portion 314 is a second telescoping base portion, such that one of the portions 312 or 314 is configured as a tube or sleeve with a hollow interior through which the other of the portions 314 or 312 extends. In the example of FIGS. 3-5, second base portion 314 is linearly translatable through an interior of first base portion 312 in a linear degree of freedom 316. The linear translation of second base portion 314 with respect to first base portion 312 can be driven by one or more actuators, e.g., motors, as described in greater detail below. Other implementations can use different configurations. For example, first base portion 312 can extend through the interior of second base portion 314 such that second base portion 314 can be linearly translated with respect to first base portion 312. In other examples, the base portions 312 and 314 can be positioned adjacent to each other along their vertical lengths to allow the linear translation.

Arm support 304 is a horizontal member that is mechanically coupled to the base support 302. Arm support 304 can include a first arm portion 318 and a second arm portion 320. The first arm portion 318 is a proximal portion of the arm support 304 that is rigidly coupled to the second base portion 314 of base support 302, and the second arm portion 320 is a distal portion of the arm support 304 that is linearly coupled to the first arm portion 318 such that the second arm portion 320 is linearly translatable with respect to the first arm portion 318 in a linear degree of freedom. In some examples, first arm portion 318 and second arm portion 320 are telescopically coupled, e.g., first arm portion 318 is a first telescoping arm portion and second arm portion 320 is a second telescoping arm portion, such that one of the portions 318 or 320 is configured as a tube or sleeve with a hollow interior through which the other of the portions 320 or 318 extends. In the example of FIGS. 3-5, second arm portion 320 is linearly translatable through an interior of first arm portion 318 in a linear degree of freedom 322. The linear translation of second arm portion 320 with respect to first arm portion 318 can be driven by one or more actuators, e.g., motors, as described in greater detail below. Other implementations can use different configurations, e.g., first arm portion 318 can extend through the interior of second arm portion 320 such that second arm portion 320 can be linearly translated with respect to first arm portion 318. In other examples, the arm portions 318 and 320 can be positioned adjacent to each other along their vertical lengths to allow the linear translation.

In some implementations, first arm portion 318 and second base portion 314 can be considered to be a single piece, e.g., a middle support or middle portion that is coupled between first base portion 312 and second arm portion 320. The middle support includes the horizontal first arm portion 318 coupled rigidly to the vertical second base portion 314 that are oriented orthogonally to each other. Second arm portion 320 is horizontally translatable in the degree of freedom 322 with respect to the middle support, and the middle support and second arm portion 320 are vertically translatable in the degree of freedom 316 with respect to first base portion 312.

In some examples as shown, arm support 304 extends along a horizontal axis that is orthogonal to a vertical axis along which base support 302 extends. In some examples, base support 302 and arm support 304 are fixed in orientation with respect to each other, e.g., they translate but do not change orientation with respect to each other. In some examples, the arm support 304 extends along an axis above a user operating the display unit, and a vertical axis extending through the base support 302 extends through the first arm portion 318 of the arm support 302. In other implementations, arm support 304 can extend at other heights and/or configurations, e.g., below a user's head or body, at the height of the user's head, in back of user and yoking around a user, etc.

Reducing vibration in the supports and members of the display system 300 can cause a smoother experience for a user operating the display unit 306. Some implementations can include one or more components in base support 302 and/or arm support 304 to provide damping that can reduce vibration in the support linkage that includes these supports 302 and 304. For example, a portion of a lever arm can be rigidly coupled internally to arm support 304 that brushes or compresses a highly damped material provided in the base support 302 to reduce vibration in the arm support 304. For example, Sorbothane® material, a viscous material, or other material having a damping coefficient above a particular threshold can be used. Similar damping components can be provided between the display unit 306 and tilt member 324, between tilt member 324 and arm support 302, etc.

Display unit 306 is mechanically coupled to arm support 304. Display unit 306 is moveable in two linear degrees of freedom provided by the linear translation of the second base portion 314 and second arm portion 320. In some implementations, these linear degrees of freedom can be provided within a vertical plane. In some examples, as shown, the vertical plane can be defined by the base support 302 and arm support 304.

Display unit 306 includes a display device, e.g., one or more display screens, projectors, or other display devices, that can display digital images. In some implementations, as in FIGS. 3-5, the display unit 306 includes two viewports 323, and the display device is provided behind or included in the viewports. In some implementations, one or more display screens or other display devices can be positioned on the display unit 306 in place of viewports 323.

Display unit 306 is rotationally coupled to the arm support 304 by a tilt member 324. In the example of FIGS. 3-5, tilt member 324 is rotationally coupled at a first end to the second arm portion 320 of the arm support 304 by a rotary coupling providing rotational motion of the tilt member 324 and display unit 306 about tilt axis 326 with respect to the second arm portion 320. In some implementations, tilt axis 326 is oriented orthogonally to the linear degrees of freedom provided to the display unit 306 by base support 302 and arm support 304. For example, tilt member 324 can provide a rotary degree of freedom to display unit 306 that is in a vertical plane the same as, or is parallel to, the vertical plane in which the degrees of freedom 316 and 322 are provided by base support 302 and arm support 304. In some implementations, tilt axis 326 is orthogonal to the plane defined by the degrees of freedom 316 and 322. In some implementations, tilt axis 326 is positioned above the display device in the display unit 306. In some implementations, tilt axis 326 is positioned above a position of a user's head when the user operates the display unit 306. In other implementations, the tilt axis can be positioned closer to the user, e.g., lower and closer to a pivot axis of the user's neck as described below. In some examples, arm support 304 can have two branches that extend on either side of the user's head, where the tilt axis 326 extends between the ends of the two branches and is aligned with a defined pivot point in the user's head or neck.

In this example, an extended portion of tilt member 324 extends toward the base support 302 from tilt axis 326 and display unit 306 is coupled to a second end of the tilt member at the extended portion. The rotational motion of tilt member 324 and display unit 306 about tilt axis 326 can be driven by one or more actuators, e.g., motors, as described in greater detail below. In some implementations, the base support 302, arm support 304, and tilt member 324 can be considered to be a support linkage having display unit 306 coupled at the distal end of the support linkage. For example, the motor(s) can be controlled by control signals from a control circuit (e.g., control system) to move display unit 306 about tilt axis 326 to a particular orientation in the tilt degree of freedom 327.

In some implementations, display unit 306 is rotationally coupled to the tilt member 324 and may rotate about a yaw axis (e.g., lateral rotation axis) 330. For example, this can be lateral or left-right rotation from the point of view of a user viewing images of display unit 306 via viewports 323. In the example of FIGS. 3-5, display unit 306 is coupled to the tilt member by a rotary mechanism which, in some implementations, can include a track mechanism. For example, in some implementations, the track mechanism includes a curved track 328, and curved track 328 is coupled to display unit 306. Track 328 slidably engages a groove member coupled to tilt member 324, allowing display unit 306 to rotate about yaw axis 330 by moving curved track 328 through a groove of the groove member. In some implementations, a curved track is coupled to tilt member 324 and a groove member is coupled to display unit 306, and the groove member engages and slides along the length of the curved track to allow the rotary movement of display unit 306 about yaw axis 330. In some implementations, the groove member can be about as long as the width of tilt member 324 and/or include at least a portion of a loop through which the curved track 328 slides.

In some implementations, curved track 328 is a curved rail that slidably engages a groove member as described. In some implementations, curved track 328 can be a curved cam follower that engages a cam roller. For example, the cam roller can be rotatably coupled to display unit 306 and, in various implementations, have an axis of rotation that is orthogonal to the yaw axis 330, or parallel to the yaw axis 330. For example, the cam roller can be cylindrical and can roll along the curved surface of the cam follower that is rigidly coupled to tilt member 324. For example, the cam roller can be held against the cam follower by walls or ridges of the cam follower. In some implementations, the cam follower can be rigidly coupled to the display unit 306, and the cam roller can be rotatably coupled to tilt member 324.

The curvature (e.g., radius) of the curved track 328 and/or groove member is selected to provide the yaw axis 330 at a particular distance from a user-facing side of display unit 306 and/or from tilt axis 326. For example, this can be a particular horizontal distance that is parallel to the degree of freedom 322 of the arm portion 320 in some implementations. For example, the yaw axis 330 can be provided at a particular distance from display unit 306 such that it approximately intersects a defined (e.g., virtual or software-defined) neck pivot axis corresponding to a pivot axis in a user's neck, as described below. The defined neck pivot axis can be used as a reference for motion of display unit 306 in some implementations. In the described implementation, the angle between yaw axis 330 and a vertical axis (e.g., parallel to degree of freedom 316) varies based on the orientation of the tilt member 324 about tilt axis 326. The yaw motion of display unit 306 about yaw axis 330 can be driven by one or more actuators, e.g., motors, using a drive mechanism such as a gear mechanism, capstan drive mechanism, etc. An example of a capstan drive mechanism is described in greater detail below with respect to FIG. 22. For example, a drive mechanism can include a capstan drum 329 that is coupled to a capstan pulley driven by a motor.

In some implementations, other couplings or bearings can be used to provide rotational motion of display unit 306 about yaw axis 330 with respect to the tilt member 324 and arm support 304. For example, a rotary joint similar to the rotary coupling between tilt member 324 and arm support 304 can be used to couple the display unit 306 to tilt member 324. In further examples, a vertically-aligned track mechanism that provides rotation about a horizontal axis, e.g., similar to members 2324 and 2330 of implementations of FIGS. 23-25, can provide a tilt degree of freedom to display unit 306 and a rotary coupling can provide a yaw degree of freedom to display unit 306.

Display system 300 thus provides display unit 306 with vertical linear degree of freedom 316, horizontal linear degree of freedom 322, rotational (tilt) degree of freedom 327, and rotational yaw degree of freedom 331. For example, the vertical and horizontal degrees of freedom allow the display unit 306 to be moved to any position within an allowed workspace (e.g., in a vertical plane), and the tilt degree of freedom allows the display unit to be moved to a particular orientation within its range of motion (e.g., within the vertical plane or a parallel vertical plane).

A combination of coordinated movement of components of display system 300 in at least two of these degrees of freedom allow display unit 306 to be positioned at various positions and orientations in its workspace, e.g., translated and/or rotated around a user, to facilitate a custom viewing experience for the user using the display unit. The motion of display unit 306 in the tilt, horizontal, and/or vertical degrees of freedom allows display unit 306 to stay close to the user's head and eyes during user head motion, and/or maintain a physical connection between the user's head (e.g., forehead) and display unit 306.

For example, display unit 306 is positionable (e.g., translatable and/or rotatable) in its workspace such that eyes of the user align with the viewports of the display unit. In addition, display unit 306 can be rotated in physical space about a defined eye pivot axis corresponding to (e.g., coincident with), for example, an eye axis through both of a user's eyes to allow a desired vertical (e.g., up-down) eye viewing angle for the user. The display unit can also be moved about yaw axis 330 to allow a desired yaw (e.g., left-right) viewing angle or orientation for the user. These rotations allow the display unit 306 to be oriented comfortably for the user to view images through the viewports.

The degrees of freedom of the display system also or alternatively allow the display system 300 to provide motion of display unit 306 in physical space about a different defined pivot axis that can be positioned in any of various locations in the workspace of the display unit 306 (examples described in greater detail below). For example, the system 300 can provide motion of display unit 306 in physical space that corresponds to motion of a user's head when operating the display system 300. This motion can include rotation about a defined neck pivot axis that approximately corresponds to a neck axis of the user's head at the user's neck. This rotation allows the display unit 306 to be moved in accordance with the user's head that is directing movement of the display unit 306, e.g., using a head input device 342. Some examples of such motion of a display unit about a neck pivot axis (FIGS. 8-11) and an eye pivot axis (FIGS. 12-14) are described below.

In another example, the motion of display unit 306 can include rotation about a defined forehead pivot axis that approximately corresponds to a forehead axis extending through the user's head at the user's forehead when the display unit 306 is oriented, as shown, in a centered yaw rotary position about yaw axis 330. In some implementations, the forehead pivot axis corresponds to a forehead axis extending through a portion of an input device of the display unit 306 (e.g., head input device 342), where the portion is at or near a point of contact between the user's forehead and the input device. In some implementations, the defined forehead pivot axis can be oriented parallel to tilt axis 326, e.g., orthogonal to the linear degrees of freedom 316 and 322. The forehead pivot axis can alternately be positioned to correspond to a different location or portion of the user's forehead or display unit.

In another example, the motion of display unit 306 can include rotation about a defined hand input device pivot axis that approximately corresponds to an axis that extends through one or more hand input devices of display unit 306 (examples described below). For example, this axis can extend through portions (e.g., the centers of grips) of both hand input devices 340*a* and 340*b* that are positioned on opposing (left and right) sides of display unit 306. In some implementations, the defined hand input device pivot axis can be oriented parallel to tilt axis 326, e.g., orthogonal to the linear degrees of freedom 316 and 322, similarly to the neck, eye, and forehead pivot axes described above. The hand input device pivot axis can alternately be positioned to correspond to a different location or portion of the display unit, e.g., a location of a different hand input device. For example, the hand input device pivot axis provides an axis of rotation about which the display unit 306 can be commanded to be rotated by manipulation of the hand input devices 340*a* and 340*b* by the user, and/or by user manipulation of other user input devices such as head input device 342, control input devices 210 and 212, etc.

In another example, the motion of display unit 306 in its workspace can include linear motion, e.g., based on linear translation in the vertical linear degree of freedom 316 and horizontal linear degree of freedom 322 and without rotational motion in the tilt and/or yaw degrees of freedom 327 and/or 331. In another example, the motion can include both linear motion and rotational motion. For example, display unit 306 can be moved linearly and then rotationally in its workspace, and/or vice-versa.

During rotation of the display unit 306 about a defined pivot axis, the movement of base support 302 in vertical degree of freedom 316 and/or the movement of arm support 304 in horizontal degree of freedom 322 can have a change in direction without a change in direction in rotation of the display unit about the defined pivot axis. For example, arm support 304 can reverse direction as the display unit is rotated from fully up to fully down positions. Thus, it is possible in some implementations for the base support or arm support to end up in the same position while the display unit has rotated from a first orientation to a second orientation about the defined pivot axis, where the support moves back and forth while the display unit transitions between those two orientations.

Display unit 306 can include input devices that allow a user to provide input to manipulate the orientation and/or position of the display unit 306 in space, and/or to manipulate other functions or components of the display system 300 and/or a larger system (e.g., teleoperated system).

For example, hand input devices 340 can be provided on display unit 306 similarly as described for FIG. 2 (shown as 206 in FIG. 2). For example, a hand input device 340*a* is positioned on a left side of the display unit 306 and a hand input device 340*b* on a right side of the display unit 306, or can be positioned on any surface of the display unit 306. The hand input devices 340*a* and 340*b* can be any of various types of user input devices (e.g., buttons, touchpads, force sensors, joysticks, knobs, trackballs, keyboards, etc.) manipulated by a user's hands to provide user hand input to the hand input device 340. The hand input device 340 outputs a control signal to the display system 300 based on the user hand input. The control signal can be used to cause display unit 306 to change its orientation and/or position in space. For example, the control system controls actuators of the display system 300 to move the base portion 314 in linear degree of freedom 316, arm portion 320 in linear degree of freedom 322, tilt member 324 in rotary degree of freedom 327, and/or display unit 306 in rotary degree of freedom 331, to cause the display unit 306 to be moved corresponding to the sensed user hand input. Sensed user hand input can also be used to control other functions of the display system 300 and/or functions of a larger system (e.g., teleoperated system 100 of FIG. 1).

Display unit 306 can include a head input device 342 similarly as described for FIG. 2 (shown as 208 in FIG. 2). In this example, head input device 342 is positioned on a surface of the display unit 306 that is facing the user's head during operation of the display unit 306. For example, head input device 342 can include one or more sensors that sense user head input that is received as commands to cause the display unit 306 to change its position and/or orientation in space. In some implementations, sensing the user head input can include sensing a presence or contact by a user's head or portion of the head (e.g., forehead) with the head input device 342. In some examples, the one or more sensors can include any of a variety of types of sensors, e.g., resistance sensors, capacitive sensors, force sensors, optical sensors, etc.

The orientation and/or position of the display unit 306 can be changed by the display system 300 based on the user head input to head input device 342. For example, sensed user input is provided to a control system, which controls actuators of the display system 300 to move the base portion 314 in linear degree of freedom 316, arm portion 320 in linear degree of freedom 322, tilt member 324 in rotary degree of freedom 327, and/or display unit 306 in rotary degree of freedom 331, to cause the display unit 306 to be moved as commanded by (e.g., in accordance with) the sensed user head input. For example, sensed head input can be used to rotate display unit 306 about a defined pivot axis, e.g., a neck pivot axis or other pivot axis as described herein. In some implementations, sensed head input can be additionally or alternatively used to rotate display unit 306 about yaw axis 330. Sensed user head input can also be used to control other functions of the display system 300 and/or of a larger system (e.g., teleoperated system 100 of FIG. 1). Thus, in some implementations, the user can move his or her head to provide input to input device to control the display unit 306 to be moved by the display system in accordance with the motion of the head, thus allowing the display unit to follow motions of the user's head and changes in viewing angle, e.g., without having to attach the display unit to the head of the user and without requiring the user to physically move the display unit. In some implementations, moving the user's head away from display unit 306 (e.g., to "pull" the display unit 306 toward the user who is moving back) can be sensed as movement in a direction away from the head input device 342 or away from display unit 306 (e.g., sensed via optical sensor or other type of sensor), or sensed as a reduction of force on the head input device 342, which causes the display system to move the display unit via control of actuators to follow the user's head.

In some implementations, display unit 306 can additionally or alternatively be moved in one or more of its described degrees of freedom in response to receiving user input from other input devices of display system 300 or of other connected systems. For example, additional hand input devices can be provided such as control input devices 210 and 212 of FIG. 2 or other control devices. In some examples, input devices can be coupled to a support surface that is coupled to base support 302, or coupled to ergonomic support 214, etc. In some implementations, user input received at foot controls 220 or other types of input devices can be used to move the display unit 306 in one or more of its degrees of freedom.

In some implementations, images displayed by the display unit 306, and/or other controlled devices, are changed and manipulated based on the sensed motion of the display unit 306, e.g., in the workspace of the display unit, about a defined pivot axis, etc. For example, motion of the display unit up and down about a defined neck pivot axis can modify display images or view in a corresponding direction.

In some implementations of a display system, display unit 306 is rotatable about yaw axis 330 in degree of freedom 331 and one or more of the other degrees of freedom 316, 322, and/or 327 are omitted from the display system 300. For example, display unit 306 can be rotated about yaw axis 330 (e.g., by actuator(s) and/or manually by a user) and the display unit 306 can be manually positioned higher and/or lower (e.g., by actuator(s) and/or manually by a user), e.g., using base support 302 or other mechanism, where horizontal degree of freedom 322 and/or tilt degree of freedom 327 are omitted.

In some example implementations, a control unit comprises a first support, a second support coupled to the first support, and a display unit rotatably coupled to the second support. The display unit and the second support are linearly translatable along a first axis in a first degree of freedom with respect to the first support, the display unit is linearly translatable along a second axis in a second degree of freedom with respect to the first support and the second support, and the display unit is rotatable about a third axis with respect to the second support in a third degree of freedom. In further examples, a tilt member couples the display unit to the second support, the tilt member being rotatable about a fourth axis with respect to the tilt member.

Figure 6:
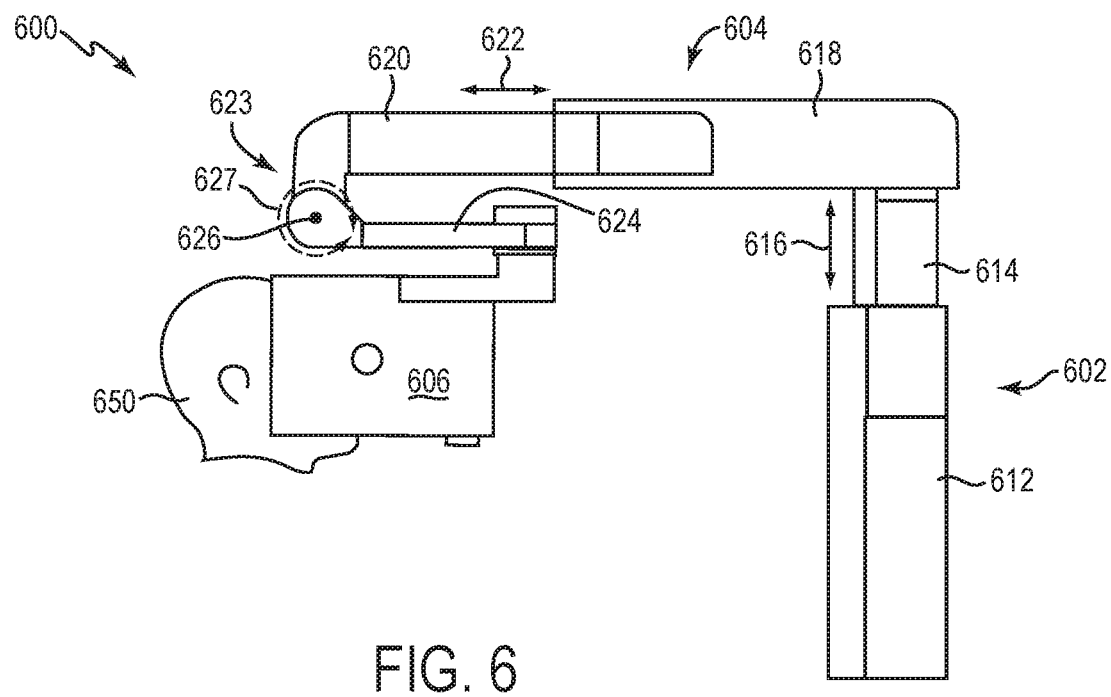
FIG. 6 is a side view of another example of a portion of display system, according to some implementations.

FIG. 6 is a side view of another example of a portion of display system 600. Display system 600 includes similar components to the display system 300 described above.

In the example of FIG. 6, second arm portion 620 of arm support 604 includes a distal portion 623 which extends vertically lower than the distal portion of the second arm portion 320 of display system 300 of FIGS. 3-5. Tilt axis 626 of tilt member 624 is located at the end of the distal portion 622. In some implementations, the extended distal portion 622 may allow tilt axis 626 to be positioned lower than the tilt axis 326 of display system 300 and closer to a defined (virtual or software-defined) pivot axis around which the display unit is to be rotated. For example, the defined pivot axis can be any of the example defined pivot axes herein, e.g., an eye pivot axis or neck pivot axis of a user 650 operating the display unit 606, examples of which are shown with respect to FIGS. 8-11.

Providing tilt axis 626 closer to a defined pivot axis may require less movement of the components of the display system 600 to rotate the display unit 606 about that defined pivot axis, as compared to a tilt axis located further from the defined pivot axis. For example, less movement may be required for second arm portion 620, second base portion 614, and/or tilt member 624, allowing a reduction in cost in some implementations due to reduced component size, motor size, etc.

Figure 7:
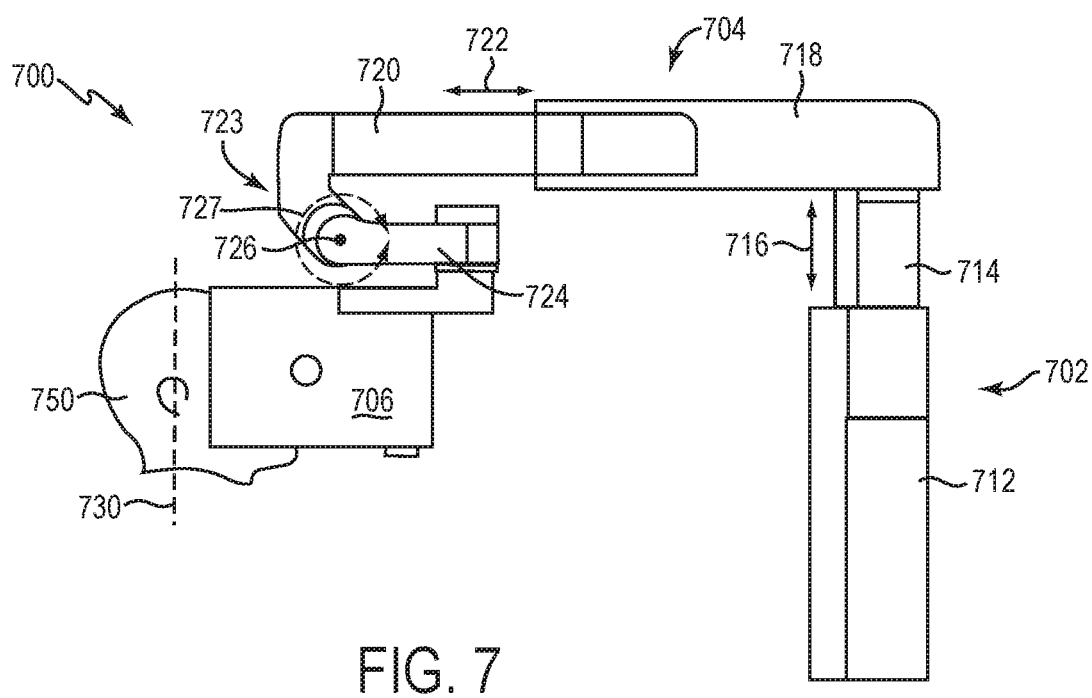
FIG. 7 is a side view of yet another example of a portion of display system, according to some implementations.

FIG. 7 is a side view of yet another example of a portion of display system 700. Display system 700 includes similar components to the display systems 300 and 600 described above.

In the example of FIG. 7, second arm portion 720 of arm support 704 includes a distal portion 723 which extends vertically lower than the distal portion of the second arm portion 320 of display system 300 of FIGS. 3-5. Distal portion 722 includes an end that extends both vertically down and toward the base support 702, e.g., away from a user location that is occupied by a user 750 when operating the display system. Tilt axis 726 is located at the end of the distal portion 722. This position of tilt axis 726 is moved further downward, and further away from the user position, as compared to tilt axis 326 of display system 300 and tilt axis 626 of display system 600.

The position of tilt axis 726 may have advantages in some implementations. For example, the end of the distal portion 723 can be further from the user 750, providing the user with a more open-feeling area in which to operate the display unit 706. Furthermore, this position can allow a reduction in the maximum gravity load on the joint of the tilt axis 726, and can also reduce the gravity load of display unit 706 in particular rotary positions about tilt axis 726, e.g., at higher tilt positions (e.g., view angles oriented horizontally and downward) where display unit 706 may be often situated during operation. For example, the position of tilt axis 726 may be closer to a position directly above a center of gravity of the component that includes display unit 706 and the track mechanism coupling display unit 706 to the tilt member 724. The position of tilt axis 726 also changes the amount of movement required by the second arm portion 720, second base portion 714, and/or tilt member 724 as compared to the tilt axis positions of display systems 300 and 600. For example, the position of tilt axis 726 may require less horizontal movement in degree of freedom 722 and more vertical movement in degree of freedom 716 than in display systems 300 and 600, which may be advantageous in some implementations, e.g., for enabling greater stiffness of the display system, operating within component or environment limitations, etc.

In addition, as shown in FIG. 7, tilt member 724 can be reduced in length compared to the lengths of tilt members 324 and 624 described in display systems 300 and 600. In addition, the distance can be reduced between the tilt axis 724 and the center of gravity of the component that includes display unit 706 and the track mechanism coupling display unit 706 to the tilt member 724. These smaller distances can reduce the joint side inertia of tilt motion of display unit 706 about tilt axis 726. In some implementations, the decrease in length of the tilt member 724 can also improve the stiffness and reduce the weight of the overall support structure.

In some implementations, the above features of display system 700 can result in lower torque output requirements, lower average current use, and lower power dissipation by a motor or other actuator used to drive rotation of the display unit 706 about the tilt axis 726, and may allow additional operating headroom for the actuator and/or drive gearing mechanism (allowing the actuator to output forces greater than typically required for operation of the display system 700).

FIGS. 8-11 are side views a portion of a display system 800 showing rotation of a display unit about an example defined neck pivot axis, according to some implementations. Display system 800 includes similar components to the display systems 300 and 600 described above.

Figure 8:
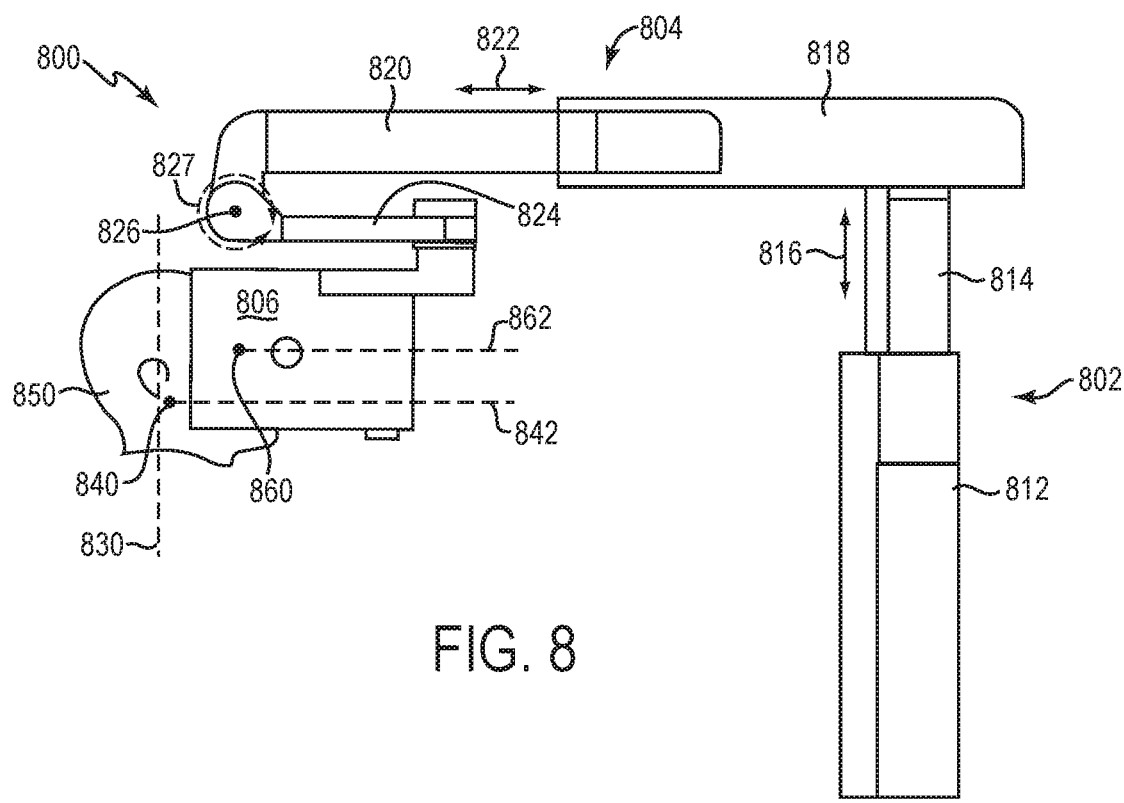
FIGS. 8-11 are side views a portion of a display system showing rotation of a display unit about a defined neck pivot axis, according to some implementations.

In FIG. 8, display system 800 is shown having a display unit in a first pivot orientation. Display system 800 includes a base support 802, an arm support 804, and a display unit 806 similarly as described above. In this example, base support 802 includes a second base portion 814 that is linearly translatable through an interior of a first base portion 812 in a linear degree of freedom 816. Arm support 804 includes a first arm portion 818 rigidly coupled to second base portion 814, and a second arm portion 820 that is linearly translatable through an interior of first arm portion 818 in a linear degree of freedom 822.

Display unit 806 is coupled to the second arm portion 820 by a tilt member 824 similarly as described in examples above. Tilt member 824 is rotationally coupled at a first end to the second arm portion 820 and rotates about axis 826. Display unit 806 can be rotationally coupled to a second end of the tilt member 824 similarly as described in examples above, and rotates about axis 826 in accordance with tilt member 824.

In FIG. 8, display unit 806 is oriented in a first pivot orientation about an example defined neck pivot axis 840 that can be approximately horizontal and can extend approximately parallel to tilt axis 826, e.g., orthogonal to a plane defined by the degrees of freedom 816 and 822. In the example implementations shown, neck pivot axis 840 is located below the tilt axis 826. In some implementations, the defined neck pivot axis 840 is located further away from the base support 802 than the display unit 806.

The defined neck pivot axis 840 (and any of the defined neck pivot axes described herein) is oriented at a location that is aligned (e.g., approximately aligned) with a pivot axis of a neck of a typical user such as user 850 when the display unit 806 is oriented, as shown, in a centered yaw rotary orientation about yaw axis 830. For example, the defined neck pivot axis can be a horizontal axis that is positioned to intersect a location at which a neck of a typical user operating the display unit approximately pivots. This location may be different in different users (e.g., users of different heights, different sizes of necks, etc.), and/or users may have different preferences as to where the defined neck pivot axis is located, such that in some implementations, a location determined (e.g., averaged) from preferred pivot locations of multiple users can be used for the defined neck pivot axis. In some example implementations, the defined neck pivot axis can be located at a location that is approximately aligned with a particular bone or any particular cervical vertebra of a neck of a user operating the display unit, e.g., an atlas bone or axis bone of a neck. In further examples, the defined neck pivot axis can be defined to correspond to other locations of a user's neck.

The neck pivot axis 840 is a virtual axis that is defined based on system parameters. The movement of the base support 802, arm support 804, and tilting member 824 can provide the rotation about neck pivot axis 840. Neck pivot axis 840 can be at different positions than shown in FIG. 8, as defined by the movement of these components in creating rotation about the desired neck pivot axis.

Some implementations may allow the location of the defined neck pivot axis to be changed, e.g., by user input, to accommodate the specific preferences or physiology of particular users. In some examples, the defined neck pivot axis can be changed to a different location at which the defined neck pivot axis is parallel to tilt axis 826 (such as a different location in which the axis is orthogonal to a vertical plane defined by the degrees of freedom 816 and 822), e.g., a new location that is up, down, forward, and/or back from a previous location in the point of view of a user. In some implementations, a stored profile or settings can be stored in association with a particular user and applied for use of the display system by that user. The stored profile includes preferred locations in space for the defined neck pivot axis and/or defined eye pivot axis (described below), any of which can be loaded for system operation. Some implementations can guide a user in determining a defined neck pivot axis customized for that user. For example, the system can output instructions to the user to bend their neck, straighten their neck, etc., and sense the rotation and trajectory of the user's head in relation to the user's body based on sensor data (e.g., images captured by an image capture device). This data is used by the display system (or control system) to determine a location of a suggested defined neck pivot axis for that user, a description of which can be output by an output device such as the display device of the display unit 806.

In the first pivot orientation shown, display unit 806 is in a horizontal view orientation about the defined pivot axis 840. A view orientation of display unit 806 with respect to neck pivot axis 840 is indicated by a line 842 that, in FIG. 8, extends horizontally through the neck pivot axis 840. In this implementation, the horizontal view orientation corresponds to tilt member 824 in a horizontal orientation parallel to arm support 804. Rotation of display unit 806 about the neck pivot axis 840 is achieved by moving portion 814 of the base support 802, portion 820 of the arm support 804, and/or tilt member 824 to appropriate positions and/or orientations.

FIG. 8 also shows a defined eye pivot axis 860. The defined eye pivot axis 860 is positioned at a location that corresponds to (e.g., is coincident with) an eye axis that intersects the eyes of a typical user such as user 850 that is looking through the viewports of the display unit 806 when the display unit 806 is oriented, as shown, in a centered yaw rotary orientation about yaw axis 830. In some implementations, the defined eye pivot axis extends parallel to tilt axis 826, e.g., orthogonal to a plane defined by the degrees of freedom 816 and 822. This defined eye pivot axis can be orthogonal to the view orientation of the display unit 806 when the display unit 806 is oriented, as shown, in a centered yaw rotary orientation about axis 830. A view orientation of display unit 806 with respect to eye pivot axis 860 is indicated by a sight line 862 that, in FIG. 8, extends horizontally through eye pivot axis 860 and indicates a reference view angle for user 850 of the display unit. In some implementations, as shown, the tilt axis 826 is located above the sight line 862. Movement of the display system 800 based on the eye pivot axis 860 is described in greater detail below with respect to FIGS. 12-14. Movement of the display system 800 about other defined pivot axes of the display unit 306, e.g., forehead pivot axis or hand input device axis, can be similarly implemented to the movement about the neck and/or eye pivot axes.

Figure 9:
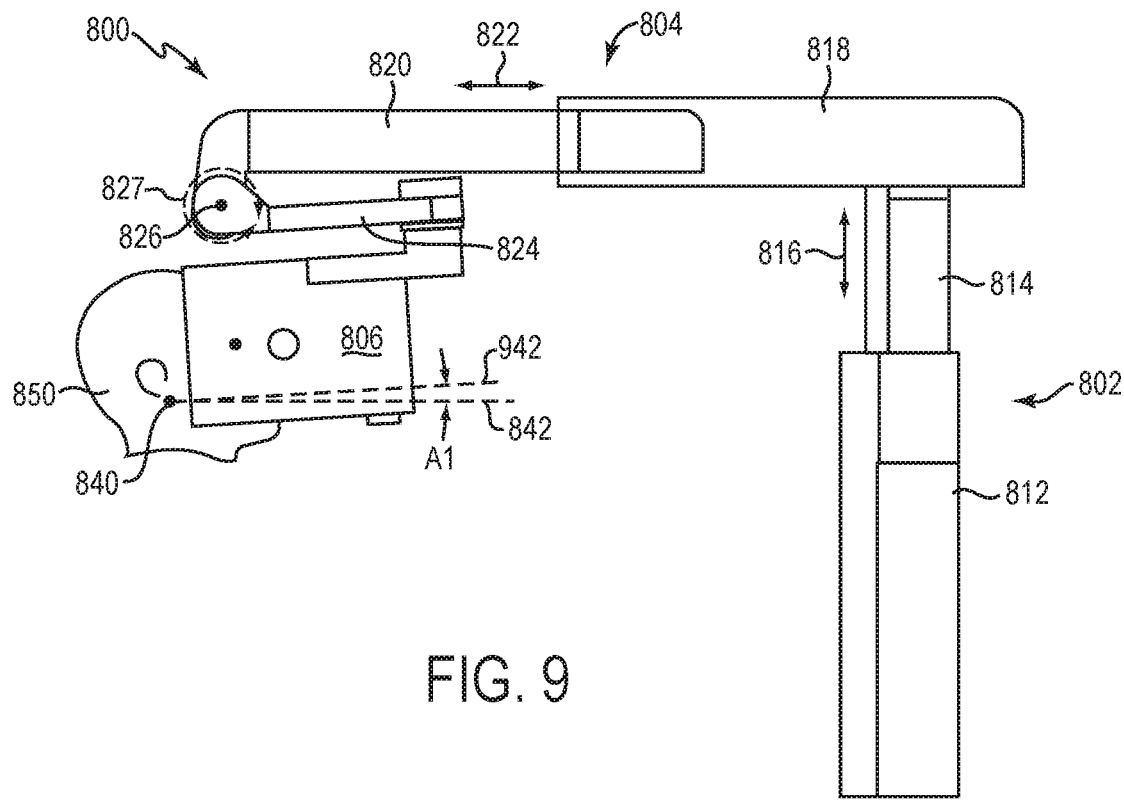

In FIG. 9, display unit 806 is oriented at a second pivot orientation rotated about the neck pivot axis 840 to allow an "upward" view angle of the user 850. An angle A1 is an example angle of rotation of the display unit 806 about the neck pivot axis 840, where angle A1 is the angle between the horizontal view orientation 842 of the display unit 806 and a neck-axis view orientation 942 of display unit 806. Display unit 806 has been rotated about the neck pivot axis 840 relative to the first pivot orientation shown in FIG. 8 by moving the base support 802, arm support 804, and tilt member 824 to positions and/or orientations as shown. For example, relative to the first pivot orientation shown in FIG. 8, the display unit 806 is moved to the second pivot orientation by rotating tilt member 824 upward to the angle shown (counterclockwise about axis 826 in the viewpoint of FIG. 9), linearly translating second arm portion 820 away from base support 802 and toward the user 850 to the position shown, and linearly translating second base portion 814 upward (e.g., away from ground) to the position shown. The tilt axis 826 is independent of the neck pivot axis 840, since rotation about the neck pivot axis 840 uses rotation about the tilt axis 826 as well as linear motion (translation) in the degrees of freedom 822 and 816.

In some implementations, the view angle shown in FIG. 9 is the upward (e.g., counterclockwise as shown in FIG. 9) rotational limit of the display unit 806. In other implementations, display unit 806 can be rotated upward (e.g., counterclockwise) by greater amounts than shown in FIG. 9 before reaching a limit to rotation in this direction.

Figure 10:
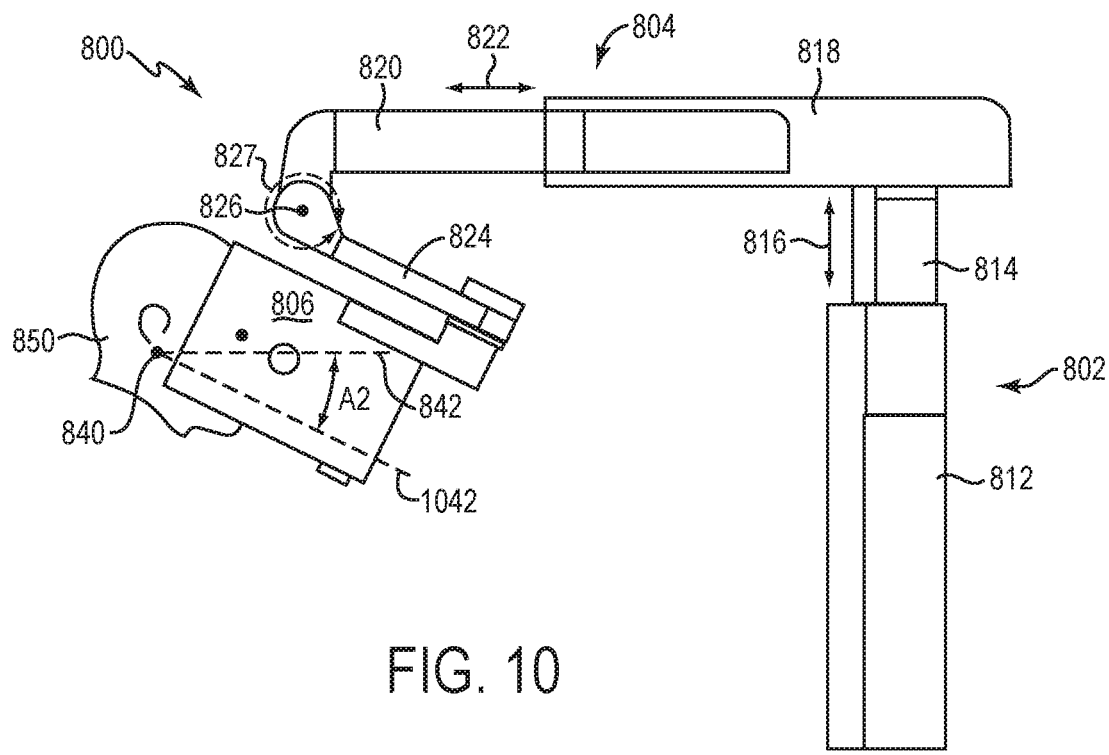

In FIG. 10, display unit 806 is oriented at a third pivot orientation rotated about the defined neck pivot axis 840 to allow a "downward" view angle of the user 850. An angle A2 is an example angle of rotation of the display unit 806 about the neck pivot axis 840, where angle A2 is the angle between the horizontal view orientation 842 of the display unit 806 and a neck-axis view orientation 1042 of the display unit. Display unit 806 has been rotated about the neck pivot axis 840 by moving the base support 802, arm support 804, and tilt member 824 to positions and/or orientations as shown. For example, relative to the first pivot orientation shown in FIG. 8, the display unit 806 is moved to the third pivot orientation by rotating tilt member 824 downward to the angle shown (clockwise about axis 826 in the viewpoint of FIG. 10), linearly translating second arm portion 820 in degree of freedom 822 toward the base support 802 and away from the user 850 to the position shown, and linearly translating second base portion 814 downward (e.g., toward ground) to the position shown.

Figure 11:
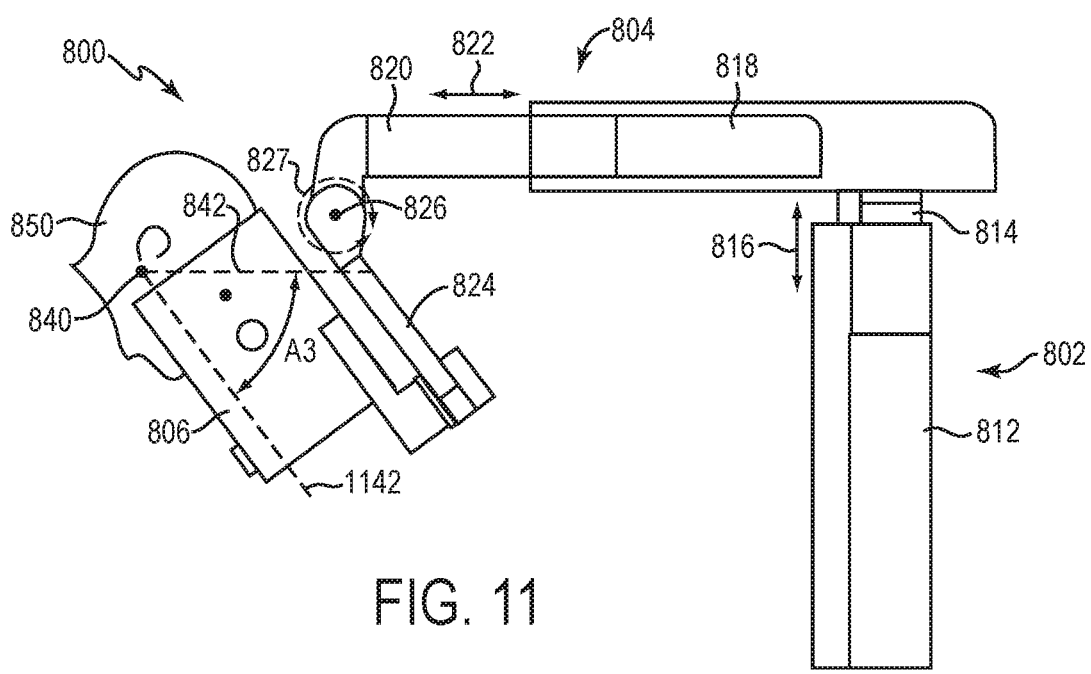

In FIG. 11, display unit 806 is oriented at a fourth pivot orientation rotated about the defined neck pivot axis 840 to allow a further downward view angle of the user 850. An angle A3 is an example angle of rotation of the display unit 806 about the neck pivot axis 840, where angle A3 is the angle between the horizontal view orientation 842 of the display unit 806 and a neck-axis view orientation 1142 of the display unit. Display unit 806 has been rotated about the neck pivot axis 840 by moving the base support 802, arm support 804, and tilt member 824 to positions and/or orientations as shown. For example, relative to the third pivot orientation shown in FIG. 10, the display unit 806 is moved to the fourth pivot orientation by rotating tilt member 824 further downward to the angle shown (clockwise about axis 826 in the viewpoint of FIG. 11), linearly translating second arm portion 820 in degree of freedom 822 toward the base support 802 and away from the user 850 to the position shown, and linearly translating second base portion 814 downward (e.g., toward ground) to the position shown.

In the example implementations shown in FIGS. 8-11, the distance between defined neck pivot axis 840 and tilt axis 826 is fixed during rotation of the display unit about the defined neck pivot axis 840.

Figure 12:
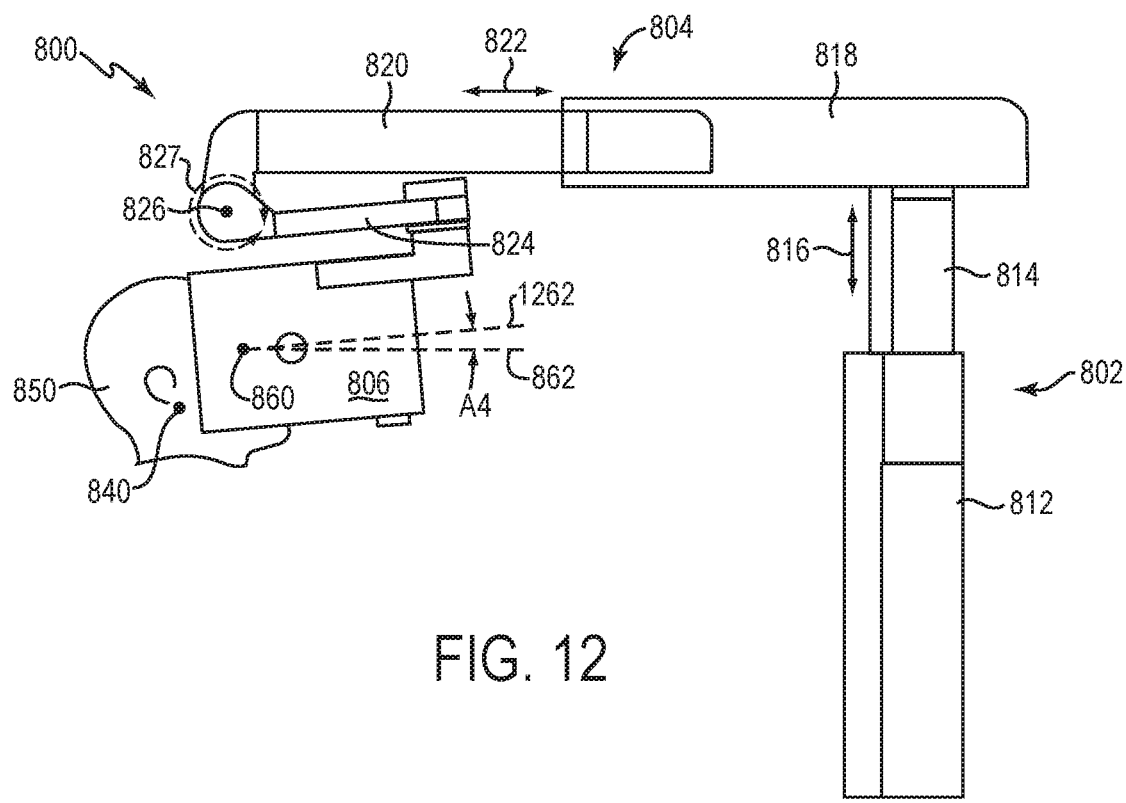
FIGS. 12-14 are side views of a portion of display system of FIG. 8 showing rotation of a display unit about a defined eye pivot axis, according to some implementations.
Figure 13:
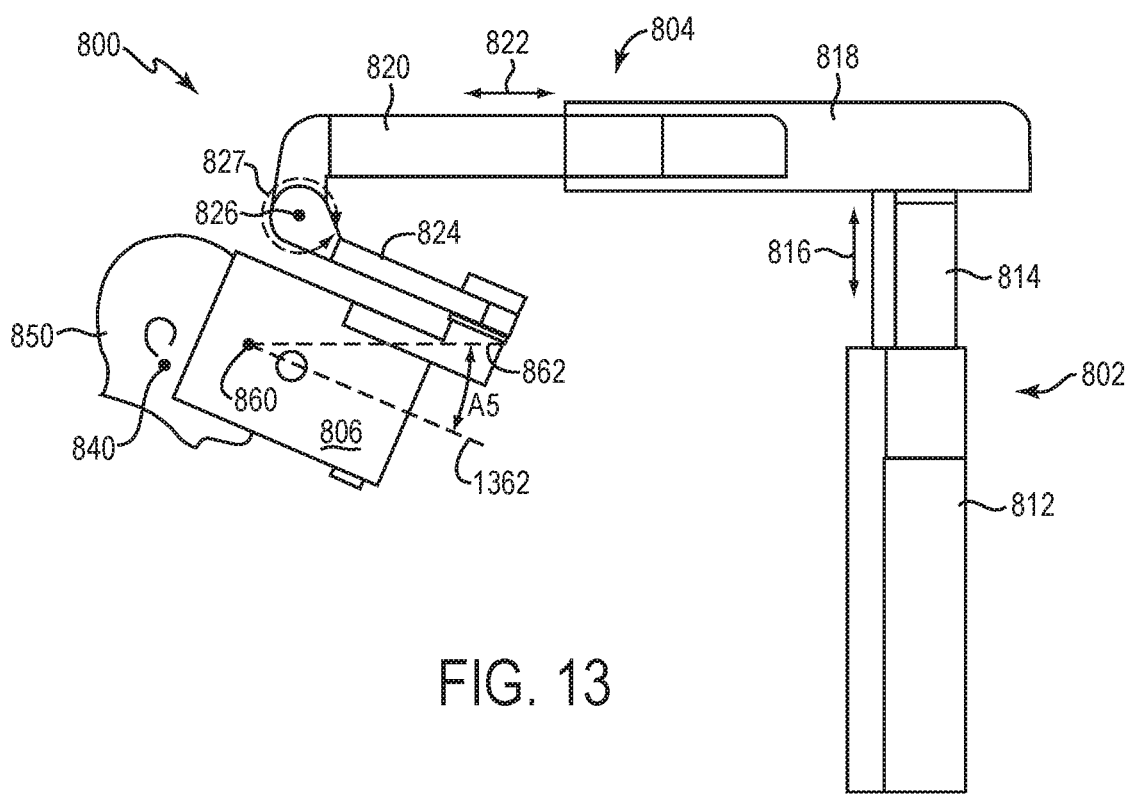
Figure 14:
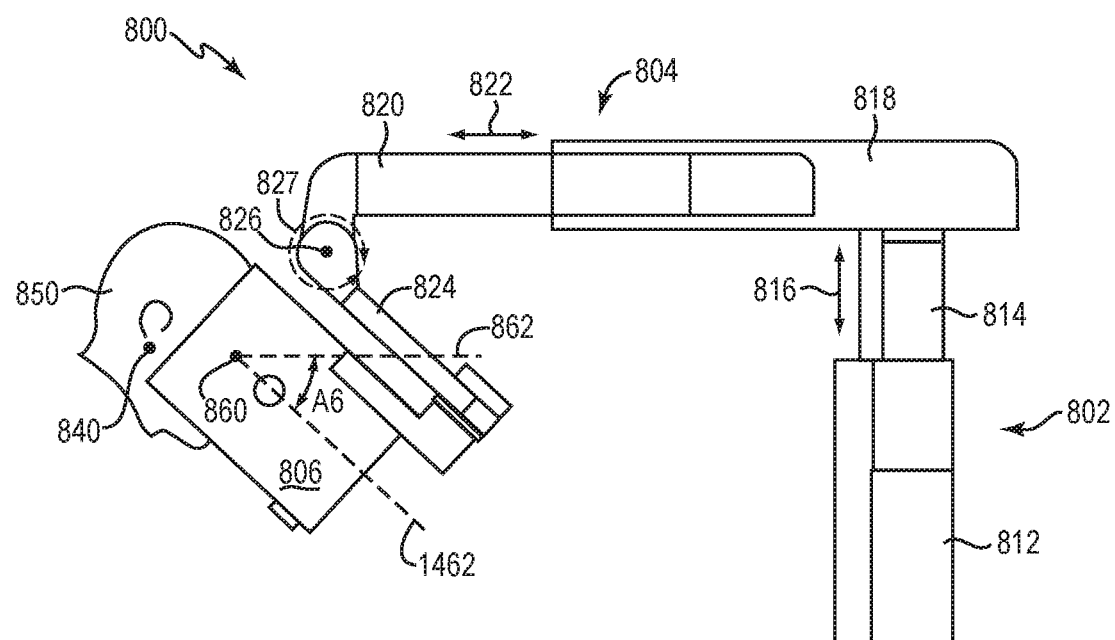

FIGS. 12-14 are side views of a portion of display system 800 showing rotation of a display unit about a defined eye pivot axis, according to some implementations. Display system 800 includes similar components to the display systems 300, 600, and 700 described above.

In FIG. 12, display unit 806 is oriented at a fifth pivot orientation, which is rotated about the defined eye pivot axis 860 to allow an upward view angle of the user 850. An angle A4 is an example angle of rotation of the display unit 806 about the eye pivot axis 860, where angle A4 is the angle between the horizontal eye-axis view orientation 862 of the display unit 806 (as shown in FIG. 8) and an eye-axis view orientation 1262 of the display unit. Display unit 806 has been rotated about the eye pivot axis 860 relative to the first pivot orientation shown in FIG. 8 by moving the base support 802, arm support 804, and tilt member 824 to positions and/or orientations as shown. For example, relative to the first pivot orientation shown in FIG. 8, the display unit 806 is moved to the fifth pivot orientation by rotating tilt member 824 upward to the angle shown (counterclockwise about axis 826 in the viewpoint of FIG. 12), linearly translating second arm portion 804 away from base support 802 and toward the user 850 to the position shown, and linearly translating second base portion 814 upward (e.g., away from ground) to the position shown. The tilt axis 826 is independent of the eye pivot axis 860, since rotation of the display unit 806 about the eye pivot axis 860 uses rotation about the tilt axis 826 as well as linear motion (translation) in the degrees of freedom 822 and 816.

In FIG. 13, display unit 806 is oriented at a sixth pivot orientation, which is rotated about the defined eye pivot axis 860 to allow a downward view angle of the user 850. An angle A5 is an example angle of rotation of the display unit 806 about the eye pivot axis 860, where angle A5 is the angle between the horizontal eye-axis view orientation 862 of the display unit 806 and an eye-axis view orientation 1362 of the display unit. Display unit 806 has been rotated about the eye pivot axis 860 by moving the base support 802, arm support 804, and tilt member 824 to positions and/or orientations as shown. For example, relative to the first pivot orientation shown in FIG. 8, the display unit 806 is moved to the sixth pivot orientation by rotating tilt member 824 downward to the angle shown (clockwise about axis 826 in the viewpoint of FIG. 13), linearly translating second arm portion 804 in degree of freedom 822 toward the base support 802 and away from the user 850 by the distance shown, and linearly translating second base portion 814 downward (e.g., toward ground) by the distance shown.

In FIG. 14, display unit 806 is oriented at a seventh pivot orientation, which is rotated about the defined eye pivot axis 860 to allow a further downward view angle of the user 850. An angle A6 is an example angle of rotation of the display unit 806 about the eye pivot axis 860, where angle A6 is the angle between the horizontal eye-axis view orientation 862 of the display unit 806 and an eye-axis view orientation 1462 of the display unit. Display unit 806 has been rotated about the eye pivot axis 860 by moving the base support 802, arm support 804, and tilt member 824 to positions and/or orientations as shown. For example, relative to the first pivot orientation shown in FIG. 8, the display unit 806 is moved to the seventh pivot orientation by rotating tilt member 824 downward to the angle shown (clockwise about axis 826 in the viewpoint of FIG. 14), linearly translating second arm portion 804 in degree of freedom 822 toward the base support 802 and away from the user 850 to the position shown, and linearly translating second base portion 814 downward (e.g., toward ground) to the position shown.

Figure 15:
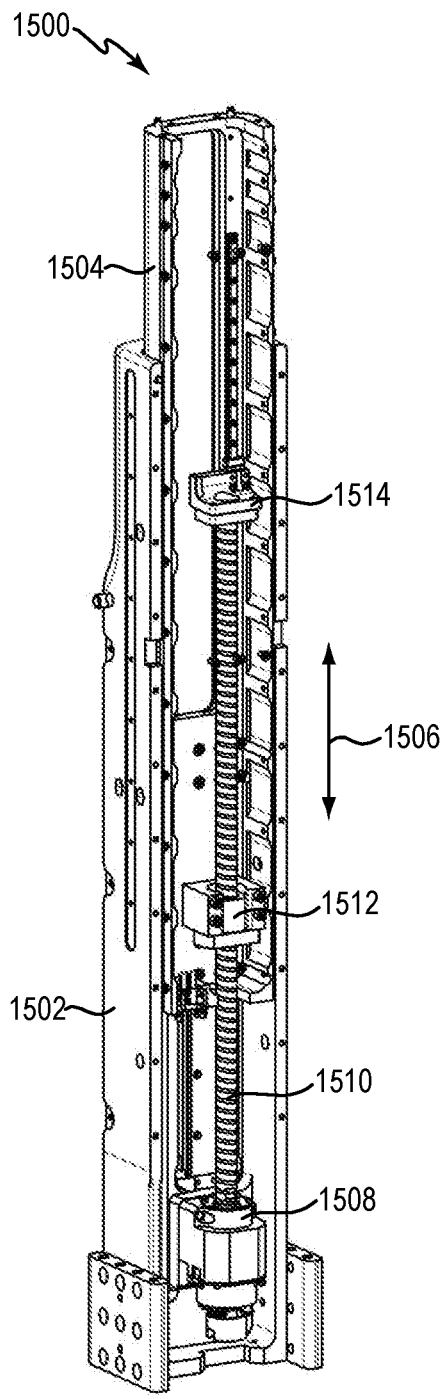
FIGS. 15-16 are perspective and side views, respectively, of an example base support for a display system, according to some implementations.
Figure 16:
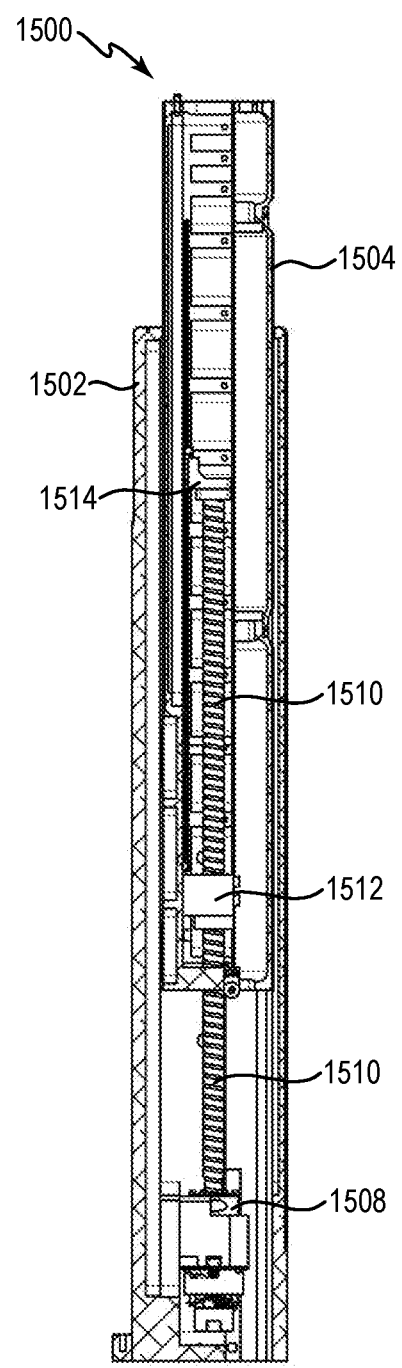

FIGS. 15 and 16 are perspective and side views, respectively, of an example base support 1500 for a display system, according to some implementations. For example, base support 1500 can be used as base support 302 of display system 300 (FIGS. 3-5), as base support 602 of display system 600 (FIG. 6), or as base support 702 of display system 700 (FIG. 7).

Base support 1500 includes a first base portion 1502 and a second base portion 1504 which are telescoping. First base portion 1502 is an elongated member that is coupled to ground, e.g., a floor or other support surface, and includes a hollow interior. Second base portion 1504 is an elongated member that is positioned in the interior of first base portion 1502 such that it is slidably engaged with the first base portion 1502. In some implementations, second base portion 1504 can include lengthwise (e.g., vertical) grooves that are engaged by mating portions of first base portion 1502, or vice-versa, to provide stability of the sliding engagement of the first and second base portions.

A drive mechanism applies force to second base portion 1504 to move this portion. The drive mechanism includes one or more actuators to linearly translate the second base portion 1504 within first base portion 1502 in the degree of freedom 1506. In this example, the drive mechanism includes a ballscrew transmission to transmit force from an actuator to the second base portion 1504. The actuator can be a rotary motor 1508 that is rigidly coupled to one end of the first base portion 1502, e.g., the end that is coupled to a grounded support. Motor 1508 has a rotating shaft that is coupled to a first end of a ballscrew 1510 that extends through the interior portion of the first base portion 1502 and through the interior portion of the second base portion 1504. Ballscrew 1510 is a threaded member that engages a threaded aperture of ballscrew nut 1512. Ballscrew nut 1512 is rigidly coupled to the second base portion 1504. In some implementations, ballscrew 1510 can be rotatably coupled at its second end to a support bearing 1514, where support bearing 1514 is rigidly coupled to the second base portion 1504. For example, support bearing 1514 can align ballscrew 1510 along a central axis through ballscrew nut 1512 parallel to ballscrew 1510. In some implementations, support bearing 1514 is not used.

In operation, the motor 1508 outputs a force on its rotatable shaft to cause the ballscrew 1510 to rotate. The rotation of the ballscrew 1510 causes the ballscrew nut 1512 and support bearing 1514 to move linearly along the longitudinal axis of the ballscrew 1510. The movement of ballscrew nut 1512 is constrained by the ballscrew 1510 and by the sliding engagement of first and second base portions 1502 and 1504. The linear motion of the ballscrew nut 1512 moves the second base portion 1504 linearly in the degree of freedom 1506. The ballscrew transmission thus converts rotary force from motor 1508 to linear force applied to the second base portion 1504. In some implementations, motor 1508 can be coupled to a sensor such as a rotary encoder that determines a rotational orientation of the motor shaft and ballscrew 1510, which can be converted to a linear position of the second base portion 1504 with respect to the first base portion 1502.

Motor 1508 can be any of a variety of types of actuators similarly as described herein for other implementations. For example, active actuators can be used, e.g., motors (e.g., DC motors), voice coils, or other types of active actuators.

Motor 1508 can be controlled using control signals from a control circuit, e.g., of a teleoperated system or other system. One or more sensors can be coupled to one or more of the components of FIG. 15 which are operative to detect the translation and/or position of the second base portion 1504 with respect to the first base portion 1502. For example, in some implementations, in addition to or instead of rotary encoder coupled to the motor 1508, a linear sensor can be coupled to the first base portion 1502 and/or second base portion 1504 to sense linear motion of the second base portion 1504 with respect to the first base portion 1502. The sensors can send signals describing sensed positions, orientations, or motion to one or more control circuits, e.g., a control system of the teleoperated system 100. In some modes or implementations, the control circuits can provide control signals indicating the sensed positions, orientation, or motion to a manipulator system. The sensors can be any of a variety of types of sensors, e.g., a magnetic sensor (e.g., magnetic incremental linear position sensor, Hall Effect sensor, etc.), optical sensor, encoder, resistance sensor, etc.

In some implementations, an additional drive mechanism can be provided on base support 1500 and coupled to an ergonomic support, e.g., an ergonomic support 214 of FIG. 2, to provide forces to cause linear up and down motion of the ergonomic support and accommodate particular user preferences for support height. In some examples, the additional drive mechanism can be mounted to the outside of the base support 1500 while the drive mechanism for second base portion 1504 can be provided on the inside of the base support 302 as shown. For example, the additional drive mechanism can use an actuator and ballscrew mechanism similarly as described above, and/or a different drive mechanism.

Figure 17:
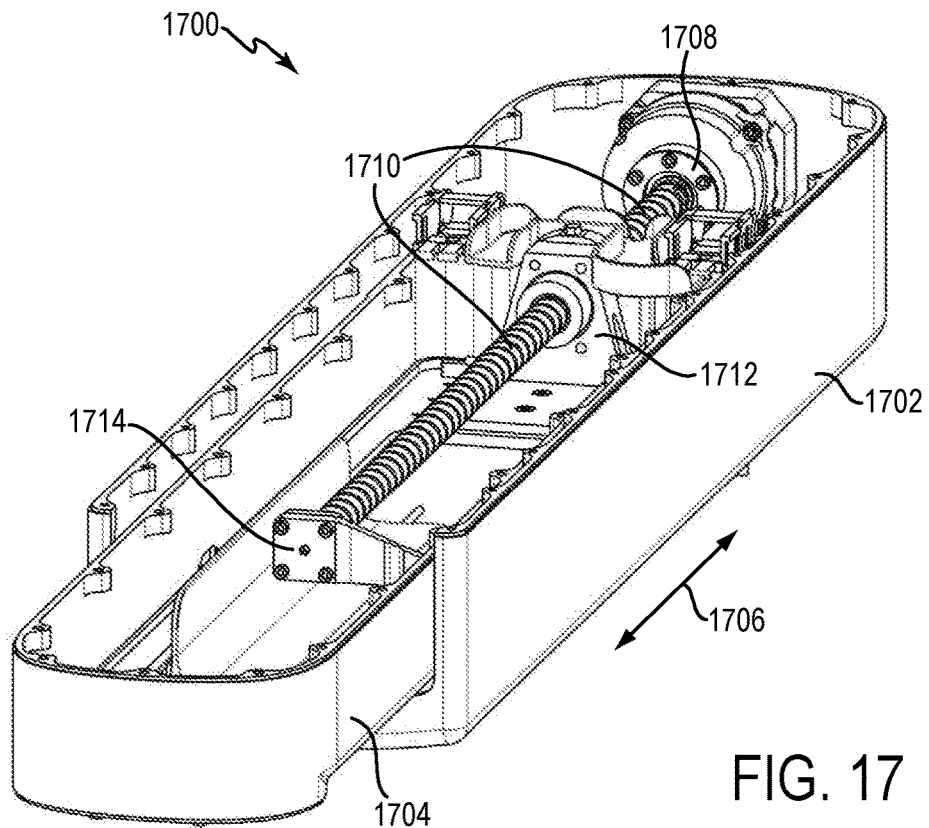
FIGS. 17 and 18 are perspective and side views, respectively, of an example arm support for a display system, according to some implementations.
Figure 18:
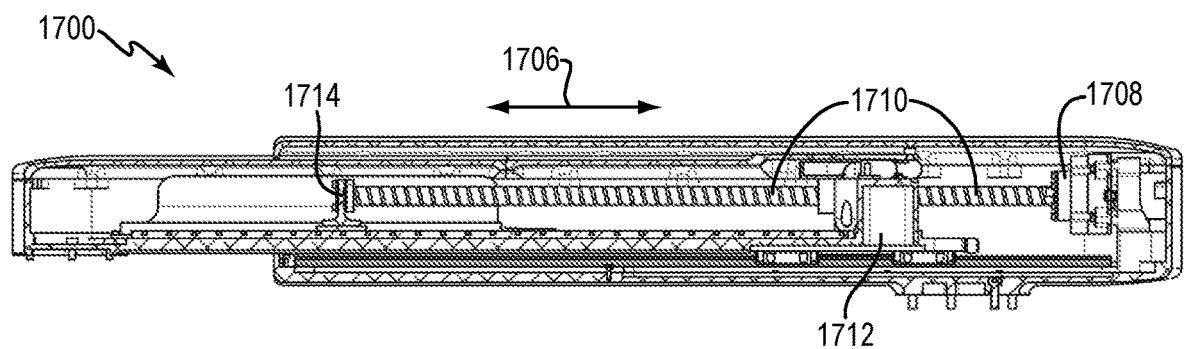

FIGS. 17 and 18 are perspective and side views, respectively, of an example arm support 1700 for a display system, according to some implementations. For example, arm support 1700 can be used as arm support 304 of display system 300 (FIGS. 3-5), as arm support 604 of display system 600 (FIG. 6), or as arm support 704 of display system 700 (FIG. 7).

Arm support 1700 includes a first arm portion 1702 and a second arm portion 1704 which are telescoping. First arm portion 1702 is an elongated member with a hollow interior and, in some implementations, can be coupled to a base support, e.g., second base portion 314, 614, or 714, or second base portion 1504 of FIG. 15. Second arm portion 1704 is an elongated member that is positioned in the interior of first arm portion 1702 such that it is slidably engaged with the first arm portion 1702. In some implementations, second arm portion 1704 can include lengthwise (e.g., horizontal) grooves that are engaged by mating portions of first arm portion 1702, or vice-versa, to provide stability of the sliding engagement of the first and second arm portions.

Second arm portion 1704 is driven by one or more actuators to linearly translate within first arm portion 1702 in the degree of freedom 1706. In this example, a ballscrew transmission is used to transmit force from an actuator to the second arm portion 1704. The actuator can be a rotary motor 1708 that is rigidly coupled to one end of the first arm portion 1702, e.g., the end that is coupled to a grounded support. Motor 1708 has a rotating shaft that is coupled to a first end of a ballscrew 1710 that extends through the interior portion of the first arm portion 1702 and through the interior portion of the second base portion 1704. Ballscrew 1710 is a threaded member that engages a threaded aperture of ballscrew nut 1712. Ballscrew nut 1712 is rigidly coupled to the second arm portion 1704. In some implementations, ballscrew 1710 can be rotatably coupled at its second end to a support 1714, and support 1714 is rigidly coupled to the second arm portion 1704 and aligns ballscrew 1710 along a central axis through the ballscrew nut 1712 parallel to the ballscrew 1710. In some implementations, support bearing 1714 is not used.

In operation, the motor 1708 outputs a force on its rotatable shaft to cause the ballscrew 1710 to rotate. The rotation of the ballscrew 1710 causes the ballscrew nut 1712 to move linearly along the longitudinal axis of the ballscrew 1710. The movement of the ballscrew nut 1712 is constrained by the ballscrew 1710 and by the sliding engagement of first and second arm portions 1702 and 1704. The linear motion of the ballscrew nut 1712 moves the second arm portion 1704 linearly in the degree of freedom 1706. The ballscrew transmission thus converts rotary force from motor 1708 to linear force applied to the second arm portion 1704. In some implementations, motor 1708 can be coupled to a sensor such as a rotary encoder that determines a rotational orientation of the motor shaft and ballscrew 1710, which can be converted to a linear position of the second arm portion 1704 with respect to the first arm portion 1702.

Motor 1708 can be any of a variety of types of actuators similarly as described herein for other implementations, e.g., active actuators such as motors (e.g., DC motors), voice coils, or other types of active actuators. Motor 1708 can be controlled using control signals from a control circuit, e.g., of a teleoperated system or other system. One or more sensors can be coupled to one or more of the components of FIG. 17 which are operative to detect the translation and/or position of the second arm portion 1704 with respect to the first arm portion 1702. For example, in some implementations, in addition to or instead of rotary encoder coupled to the motor 1708, a linear sensor can be coupled to the first arm portion 1702 and/or second arm portion 1704 to sense linear motion of the second arm portion 1704 with respect to the first arm portion 1702. The sensors can send signals describing sensed positions, orientations, or motion to one or more control circuits, e.g., a control circuit of the teleoperated system 100. In some modes or implementations, the control circuits can provide control signals indicating the sensed positions, orientations, or motion to a manipulator system. The sensors can be any of a variety of types of sensors, e.g., a magnetic sensor (e.g., magnetic incremental linear position sensor, Hall Effect sensor, etc.), optical sensor, encoder, resistance sensor, etc.

Figure 19:
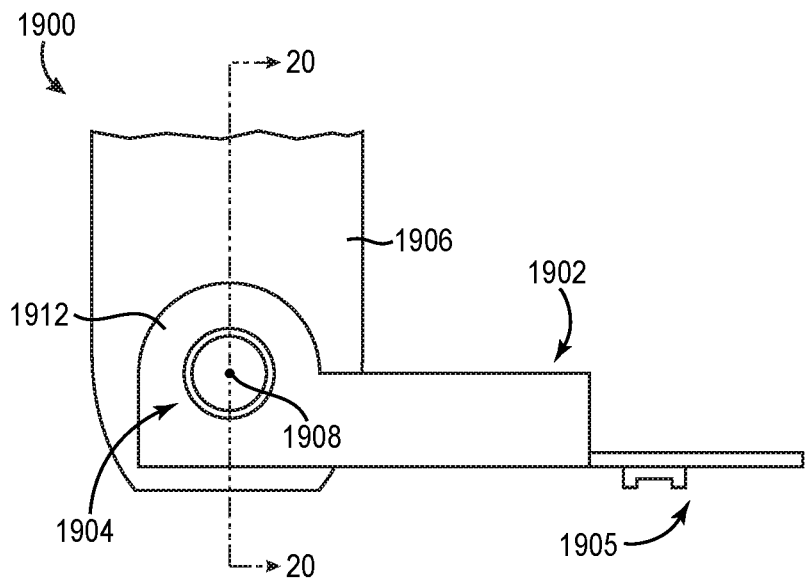
FIGS. 19-21 are side, front, and perspective views, respectively, of an example tilt mechanism, according to some implementations.
Figure 20:
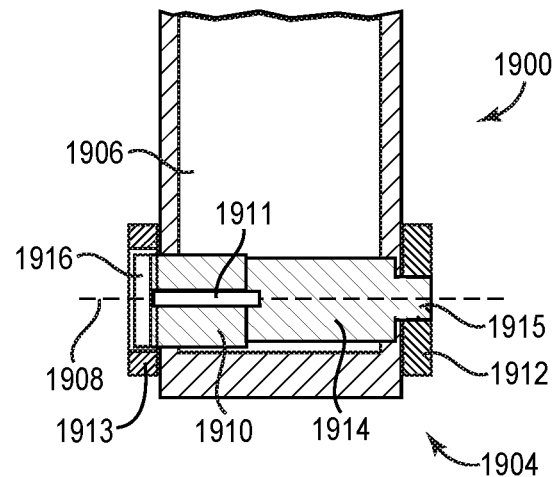
Figure 21:
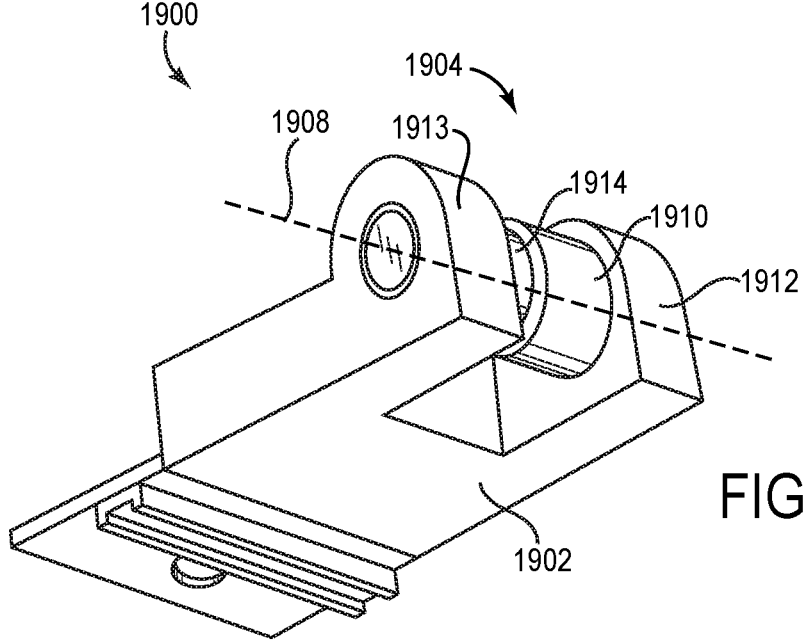

FIGS. 19, 20, and 21 are side, front, and perspective views, respectively, of an example tilt mechanism 1900, according to some implementations.

Tilt mechanism 1900 includes a tilt member 1902 and a tilt drive mechanism 1904. For example, tilt member 1902 can be used as tilt member 324 of the display system 300 (FIGS. 3-5), as tilt member 624 of the display system 600 (FIG. 6), or as tilt member 724 of the display system 700 (FIG. 7). For example, a display unit, such as display unit 306 (FIG. 3), display unit 606 (FIG. 6), or display unit 706 (FIG. 7), can be coupled to the tilt member 1902 similarly as described above. For example, a display unit can be coupled at a portion 1905 of the tilt member 1902, an example of which is described with reference to FIG. 22.

Tilt member 1902 is rotatably coupled to a support 1906. In some examples, support 1906 can be a portion (e.g., distal portion) of, or coupled to, an arm support such as second arm portion 320, 620, 720, or 1704 described above. Tilt member 1902 can rotate about a tilt axis 1908, which, for example, can be the tilt axis 326, 626, or 726 described above.

Tilt drive mechanism 1904 can include one or more actuators to drive the rotation of the tilt member 1902 to a particular orientation about tilt axis 1908. In this example, a motor 1910 includes a driven shaft 1911 that is rigidly coupled to an extended portion 1912 and/or 1913 of the tilt member 1902. Motor 1910 has a housing rigidly coupled to the support 1906. When the shaft 1911 is rotated by the motor 1910, the tilt member 1902 is rotated about tilt axis 1908. In some implementations, the driven shaft 1911 of the motor 1910 can be coupled to both first and second extended portions 1912 and 1913 of the tilt member 1902, or the driven shaft can be coupled to one of the first and second extended portions 1912 or 1913. In some implementations, the tilt member 1902 includes a single extended portion 1912 or 1913.

Motor 1910 can be any of a variety of types of actuators, e.g., active actuators such as motors (e.g., DC motors), voice coils, or other types of active actuators. Motor 1910 can be controlled using control signals from a control circuit, e.g., of a teleoperated system or other system.

In some implementations, motor 1910 is coupled to a drive transmission 1914 that can provide gearing of the output rotation of the motor shaft to increase or decrease the amount of rotation of the connected tilt member 1902, instead of tilt member 1902 being directly rotated the same amount as the motor shaft 1911. Drive transmission 1914 includes a shaft 1915 that is rigidly coupled to the extended member 1912 of the tilt member 1902. For example, drive transmission 1914 can provide gearing such that a full rotation of the drive shaft 1911 provides a partial rotation of shaft 1915, causing a partial rotation of the tilt member 1902. In some examples, drive transmission 1914 is a harmonic drive mechanism. In some implementations, a different drive transmission can be used, e.g., a capstan drive mechanism, mechanical gears, etc.

One or more sensors can be coupled to one or more of the components of the tilt mechanism 1902 which are operative to detect the rotation of the tilt member 1902 about axis 1908. For example, in some implementations, a sensor 1916 (e.g., rotary encoder) is coupled to shaft 1911 of motor 1910 and determines a rotational orientation of shaft 1911 so that a rotary orientation of the tilt member 1902 about axis 1908 can be determined (e.g., taking into account rotation reduction provided by drive transmission 1914). In some implementations, a sensor can be coupled to other components of the tilt mechanism 1900 to sense the rotary orientation of the tilt member 1902 about axis 1908. The sensor(s) can send signals describing sensed positions, orientations, or motion to one or more control circuits, e.g., a control system of the teleoperated system 100. In some modes or implementations, the control circuits can provide control signals indicating the sensed positions, orientations, or motion to a manipulator system. The sensors can be any of a variety of types of sensors, e.g., a rotary encoder, a magnetic sensor (e.g., magnetic incremental linear position sensor, Hall Effect sensor, etc.), optical sensor, encoder, resistance sensor, etc.

Figure 22:
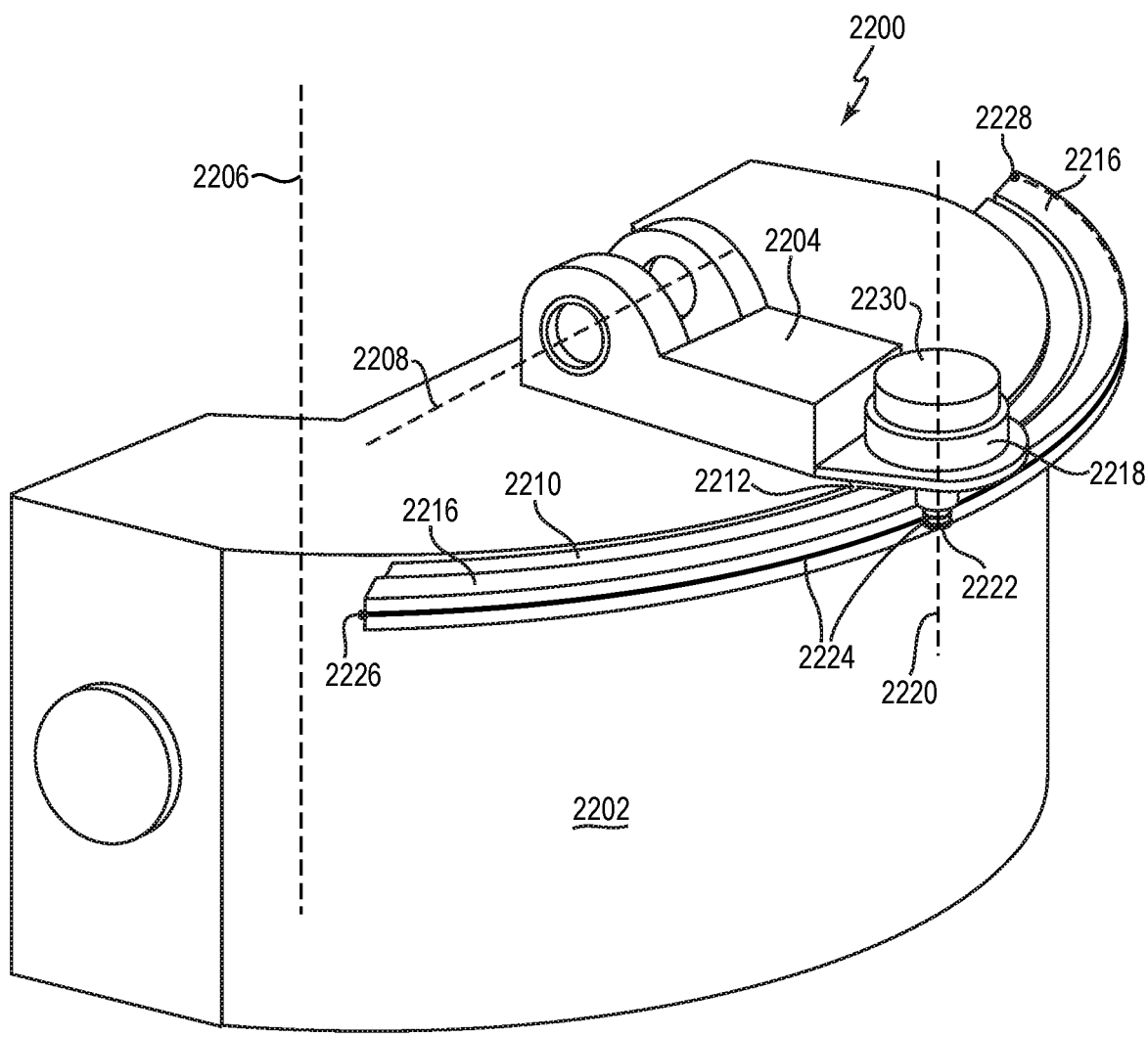
FIG. 22 is a perspective view of an example display unit mechanism, according to some implementations.

FIG. 22 is a perspective view of an example display unit mechanism 2200, according to some implementations. Display unit mechanism 2200 couples a display unit 2202 to a tilt member 2204. For example, display unit 2202 can be display unit 306, 606, or 706 of FIG. 3-5, 6, or 7, respectively. In another example, tilt member 2204 can be tilt member 324, 624, or 724 of FIG. 3, 6, or 7, or tilt member 1902 of FIGS. 19-21.

Display unit mechanism 2200 includes a rotary mechanism rotationally coupling the display unit 2202 to the tilt member 2204 and allowing the display unit 2202 to pivot about an axis 2206 with respect to the tilt member 2204. In this example, axis 2206 can be perpendicular to the axis 2208 about which the tilt member 2204 rotates. For example, axis 2206 can be axis 330, 630, or 730 described above in FIG. 3, 6, or 7, respectively, and axis 2208 can be axis 1908 of FIGS. 19-21, or tilt axis 326, 626, or 726 in FIG. 3, 6, or 7, respectively.

In this example, the rotary mechanism is a track mechanism that includes a curved track bearing including a curved track 2210 and a groove member 2212. The curved track 2210 is rigidly coupled to the display unit 2202 and is slidably engaged with a groove or aperture in groove member 2212 that is coupled to or a part of the tilt member 2204. The curvature of curved track 2210 allows the display unit 2202 to pivot about axis 2206 by sliding the curved track 2210 within the groove of groove member 2212 along the length of the curved track 2210. In some other implementations, a curved track can be coupled to the tilt member 2204 and a groove member (or a slidably-mating curved rail) can be coupled to display unit 2202, where the groove member rotates with the display unit 2202 about the axis 2206 along the length of the curved track.

Display unit mechanism 2200 includes a drive mechanism that outputs force to the display unit 2202 and drives the display unit 2202 about axis 2206. In this example, the drive mechanism includes a capstan drum 2216 which, in some implementations, is rigidly coupled to the curved track 2210 (or in some implementations, can be included as a unitary part of curved track 2210). The drive mechanism includes a motor 2218 that has a housing rigidly coupled to the tilt member 2204. Motor 2218 can be any of a variety of types of actuators, e.g., active actuators such as motors (e.g., DC motors), voice coils, or other types of active actuators. Motor 2218 can be controlled using control signals from a control circuit, e.g., of a teleoperated system or other system.

A rotating shaft of the motor 2218 rotates about an axis of rotation 2220 that, for example, can be parallel to the axis 2206 about which the display unit 2202 rotates. The shaft of motor 2218 is rigidly coupled to a capstan pulley 2222 and rotates the capstan pulley 2222 about axis 2220. In some implementations, capstan pulley 2222 is coupled to the capstan drum 2216 by a cable 2224. For example, a first end of cable 2224 can be attached to a first end 2226 of the capstan drum 2216, routed along the side surface of the capstan drum 2216, wrapped around capstan pulley 2222, and routed along the surface of the capstan drum 2216 to second end 2228 where the second end of the cable is attached. In some implementations, two cables can be used, e.g., a first cable having a first end attached to drum first end 2226 and a second end attached to capstan pulley 2222, and a second cable having a first end attached to drum second end 2228 and a second end attached to capstan pulley 2222, the two cables being routed along the side surface of the capstan drum 2216.

In operation, motor 2218 is controlled to rotate its shaft about axis 2220, causing rotation of capstan pulley 2222. The rotation of capstan pulley 2222 causes movement of cable(s) 2224 via winding and unwinding of the cable(s) 2224 around the capstan pulley 2222. The movement of the cable(s) 2224 causes display unit 2202 to rotate about axis 2206 as guided by the curved track 2210 in the groove or aperture of groove member 2212.

In some implementations, a brake can be provided to stop the motion of the display unit 2202 about the axis 2206, e.g., during deactivation of the display system. For example, a brake can be used which applies braking force about axis 2206 when power is removed so as to prevent rotation of display unit 2202, e.g., during non-operation. In various implementations, the brake can include a rotary brake that is coupled to the shaft of motor 2218 or coupled to capstan pulley 2222 to reduce or prevent the motor shaft from rotating, and/or the brake can include a linear brake that is positioned between tilt member 2204 and display unit 2202, and/or between tilt member 2204 and capstan drum 2216/curved track 2210, to cause friction in the relative movement of these components. For example, the brake can include a spring-loaded disc brake.

One or more sensors can be coupled to one or more of the components of the display unit mechanism 2200 which are operative to detect the rotation of the display unit 2202 about axis 2206. For example, in some implementations, a sensor 2230 (e.g., rotary encoder) is coupled to the shaft of motor 2218 and determines a rotational orientation of the motor shaft in order to detect the rotary orientation of the display unit 2202 about axis 2206. In some implementations, a sensor can be coupled to other components of the display unit mechanism 2200 to sense the rotary orientation of the display unit 2202. The sensor(s) can send signals describing sensed positions, orientations, or motion to one or more control circuits, e.g., a control system of the teleoperated system 100. In some modes or implementations, the control circuit can provide control signals indicating the sensed positions, orientations, or motion to a manipulator system. The sensors can be any of a variety of types of sensors, e.g., a rotary encoder, a magnetic sensor (e.g., magnetic incremental linear position sensor, Hall Effect sensor, etc.), optical sensor, encoder, resistance sensor, etc.

In other example implementations, curved track 2210 and capstan drum 2216 can be coupled to tilt member 2204, and groove member 2212 and motor 2218 can be coupled to display unit 2202.

Figure 23:
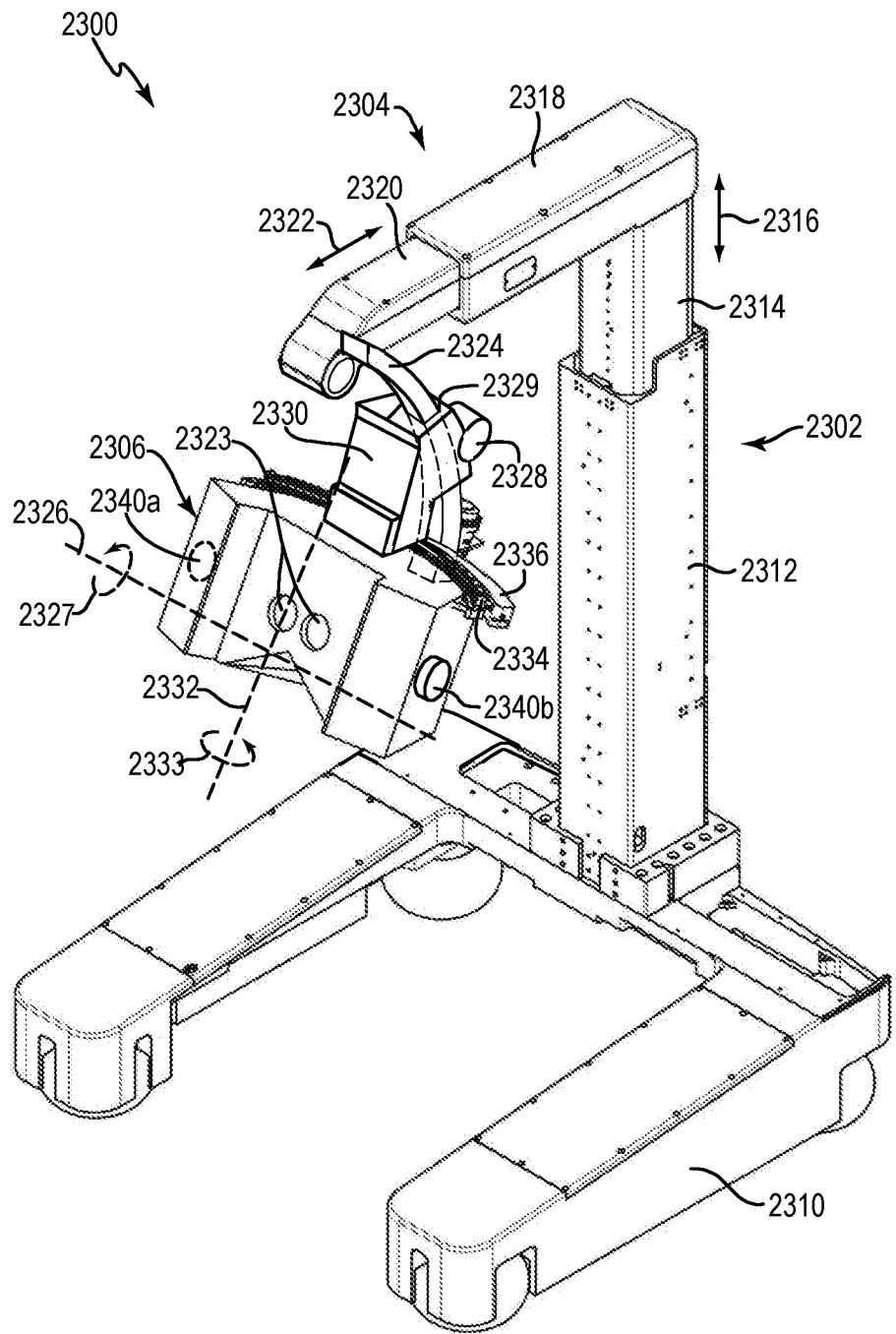
FIGS. 23-25 are perspective, front, and side views, respectively, of another implementation of a display system, according to some implementations.
Figure 24:
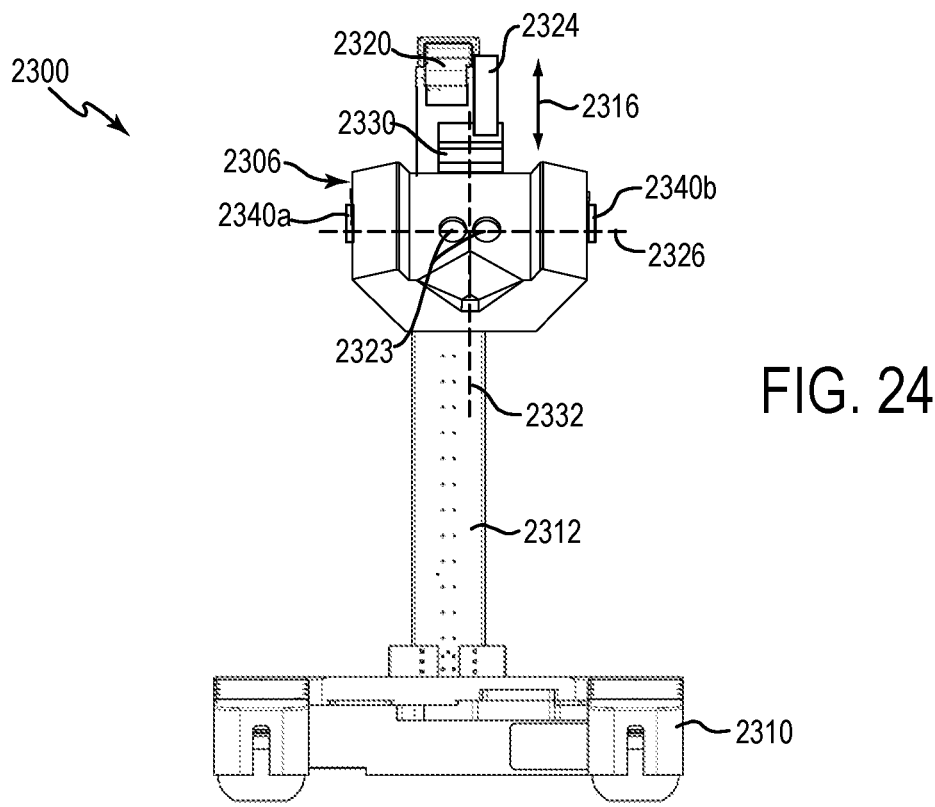
Figure 25:
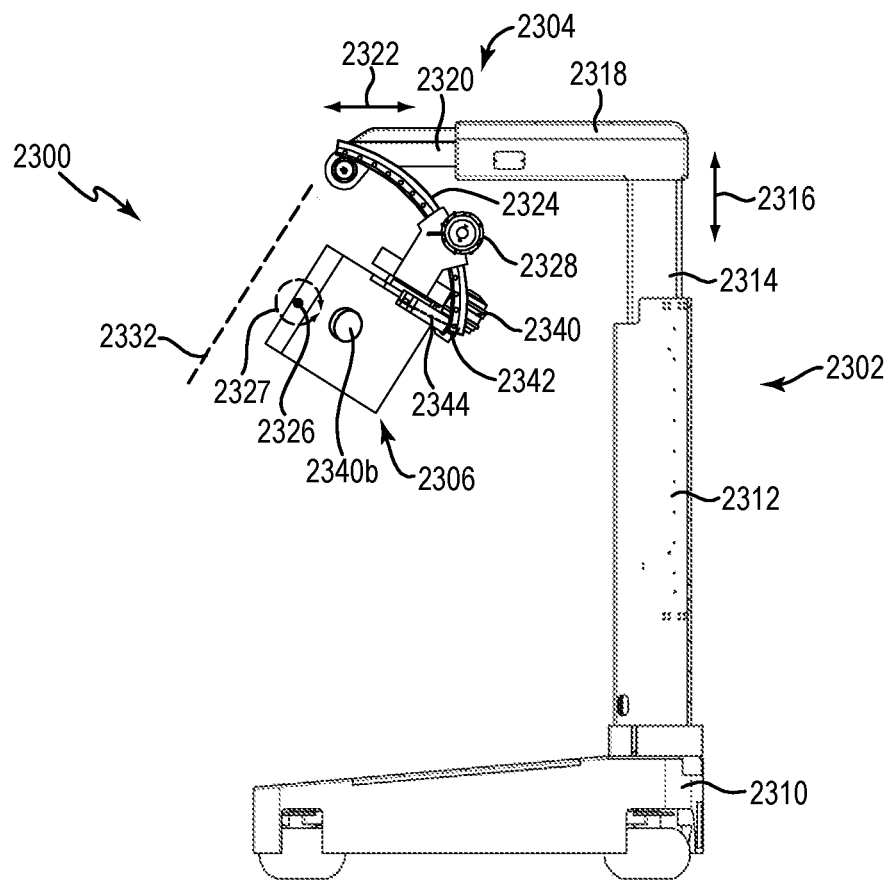

FIG. 23 is a perspective view, FIG. 24 is a front view, and FIG. 25 is a side view of an example of another implementation of a display system 2300, according to some implementations. In some examples, display system 2300 can be used in a user control system 102 of a teleoperated system as described for FIG. 1 and elsewhere herein, or can be used in other systems or as a standalone system as described above. Features of display system 2300 can be similar to those of display system 300 of FIG. 3 as described above, unless otherwise indicated.

Display system 2300 includes a base support 2302, an arm support 2304, and a display unit 2306. As described in greater detail below, display unit 2306 is provided with multiple degrees of freedom of movement by a support linkage including the base support 2302, arm support 2304 coupled to the base support 2302, and a track mechanism including a track member and a sliding member (as described below) coupled to the arm support 2304. Display unit is coupled to the sliding member.

In some implementations, base support 2302 and arm support 2304 can be similarly implemented as described above with reference to FIGS. 3-7. In some examples, base support 2302 is a vertical member that is mechanically grounded, e.g., coupled to ground. Base support 2302 can be mechanically coupled to a support structure 2310. Base support 2302 includes a first base portion 2312 and a second base portion 2314. The first base portion 2312 is a proximal portion of the base support 2302 that can be mechanically grounded, and the second base portion 2314 is a distal portion of the base support 2302 that is linearly coupled to the first base portion 2312 such that the second base portion 2314 is translatable with respect to the first base portion 2312 in a linear degree of freedom. In some examples, first base portion 2312 and second base portion 2314 are telescopically coupled, e.g., first base portion 2312 is a first telescoping base portion and second base portion 2314 is a second telescoping base portion, such that one of the portions 2312 or 2314 is configured as a tube or sleeve with a hollow interior through which the other of the portions 2314 or 2312 extends. In the example of FIGS. 23-25, second base portion 2314 is linearly translatable through an interior of first base portion 2312 in a linear degree of freedom 2316. The linear translation of second base portion 2314 with respect to first base portion 2312 can be driven by one or more actuators, e.g., motors, e.g., similarly as described above with reference to FIGS. 15 and 16. Other implementations can use different configurations. For example, first base portion 2312 can extend through the interior of second base portion 2314 such that second base portion 2314 can be linearly translated with respect to first base portion 2312. In other examples, the base portions 2312 and 2314 can be positioned adjacent to each other along their vertical lengths to allow the linear translation.

Arm support 2304 is a horizontal member that is mechanically coupled to the base support 2302. Arm support 2304 includes a first arm portion 2318 and a second arm portion 2320. The first arm portion 2318 is a proximal portion of the arm support 2304 that is rigidly coupled to the second base portion 2314 of base support 2302, and the second arm portion 2320 is a distal portion of the arm support 2304 that linearly coupled to the first arm portion 2318 such that the second arm portion 2320 is linearly translatable with respect to the first arm portion 2318 in a linear degree of freedom. In some examples, first arm portion 2318 and second arm portion 2320 are telescopically coupled, e.g., first arm portion 2318 is a first telescoping arm portion and second arm portion 2320 is a second telescoping arm portion, such that one of the portions 2318 or 2320 is configured as a tube or sleeve with a hollow interior through which the other of the portions 2320 or 2318 extends. In the example of FIGS. 23-25, second arm portion 2320 is linearly translatable through an interior of first arm portion 2318 in a linear degree of freedom 2322. The linear translation of the second arm portion 2320 with respect to the first arm portion 2318 can be driven by one or more actuators, e.g., motors, as described in greater detail with respect to FIGS. 17 and 18. Other implementations can use different configurations, e.g., first arm portion 2318 can extend through the interior of second arm portion 2320 such that the second arm portion 2320 can be linearly translated with respect to the first arm portion 2318. In other examples, the arm portions 2318 and 2320 can be positioned adjacent to each other along their vertical lengths to allow the linear translation.

In some implementations, first arm portion 2318 and second base portion 2314 can be considered to be a single piece, e.g., a middle support or middle portion that is coupled between first base portion 2312 and second arm portion 2320. The middle support includes the horizontal first arm portion 2318 coupled rigidly to the vertical second base portion 2314 that are oriented orthogonally to each other. Second arm portion 2320 is horizontally translatable in the degree of freedom 2322 with respect to the middle support, and the middle support and second arm portion 2320 are vertically translatable in the degree of freedom 2316 with respect to first base portion 2312.

In some examples as shown, arm support 2304 extends along a horizontal axis that is orthogonal to a vertical axis along which base support 2302 extends. In some examples, base support 2302 and arm support 2304 are fixed in orientation with respect to each other, e.g., they translate but do not change orientation with respect to each other. In some examples, the arm support 2304 extends along an axis above a user operating the display unit, and a vertical axis extending through the base support 2302 extends through the first arm portion 2318 of the arm support 2302. In other implementations, arm support 2304 can extend at other heights and/or configurations, e.g., below a user's head or body, at the height of the user's head, in back of user and yoking around a user, etc. Some implementations can provide components in display system 2300 to reduce vibration in the supports and members of the display system 2300 to provide a smoother experience for a user operating the display unit 2306, similarly as described for FIGS. 3-5.

Display unit 2306 is mechanically coupled to arm support 2304. Display unit 2306 is moveable in two linear degrees of freedom provided by the linear translation of the second base portion 2314 and second arm portion 2320. In some implementations, these linear degrees of freedom can be provided within a vertical plane. In some examples, as shown, the vertical plane can be defined by the base support 2302 and arm support 2304.

Display unit 2306 includes a display device that can display images, e.g., one or more display screens, projectors, or other devices. In some implementations, as in FIGS. 23-25, the display unit 2306 includes two viewports 2323, and the display device is provided behind or included in the viewports. In some implementations, one or more display screens or other display devices can be positioned on the display unit 2306 in place of viewports 2323.

Display unit 2306 is coupled to the arm support 2304 via a track member 2324 and a sliding member 2330. In the example of FIGS. 23-25, a first end of track member 2324 is rigidly coupled to a distal end of the second arm portion 2320. The track member 2324 extends in a curved or bent configuration from its first end to a second end. For example, in the orientation of FIGS. 23-25, the second end of the track member 2324 is lower than the first end. In this example, the track member 2324 extends approximately down (toward support structure 2310) and toward the base support 2302 from the first end of the track member. In some implementations track member 2324 is curved about a central axis (e.g., axis 2326). In some implementations, track member 2324 includes no linear segments or portions.

Display unit 2306 is coupled to sliding member 2330, and sliding member 2330 is slidably coupled to track member 2324. In some implementations, as shown in FIGS. 23-25, sliding member 2330 includes an aperture 2329 (or slot or groove) that extends through the sliding member, and track member 2324 extends through aperture 2329 to allow sliding member 2330 and display unit 2306 to slide along the length of the track member. Sliding member 2330 and display unit 2306 can be positioned at any of multiple positions along track member 2324. Track member 2324 thus provides a set of positions for the display unit 2306 that follow the curved configuration of track member 2324.

In the example of FIGS. 23-25, track member 2324 extends along a curved path about an axis 2326, which is a tilt axis for the display unit 2306. In some implementations, a radius of the curved track member 2324 determines the position of the tilt axis 2326. For example, the tilt axis 2326 can extend through a point that is a radius distance from the track member 2324, the point being at the center of a circle (or other shape) at least partially traced by the track member 2324. For example, as sliding member 2330 and display unit 2306 are moved along the track member 2324, these elements move rotationally about tilt axis 2326 with respect to the second arm portion 2320 in a rotary (tilt) degree of freedom 2327. In some implementations, tilt axis 2326 is oriented orthogonally to the linear degrees of freedom provided to the display unit 2306 by base support 2302 and arm support 2304. For example, sliding member 2330 can provide a rotary degree of freedom to display unit 2306 that is in a vertical plane that is the same as, or is parallel to, the vertical plane in which the degrees of freedom 2316 and 2322 are provided by base support 2302 and arm support 2304. In some implementations, tilt axis 2326 is orthogonal to the plane defined by the degrees of freedom 2316 and 2322. In some implementations, the base support 2302, arm support 2304, and guiding member 2330 can be considered to be a support linkage having display unit 2306 coupled at the distal end of the support linkage.

Sliding element 2330 and display unit 2306 can be rotated about a defined pivot axis based on movement allowed by first arm portion 2314, second arm portion 2320, and track member 2324. Some examples of such rotation about defined pivot axes is described below with respect to FIGS. 26-31.

In some other example implementations, a different mechanism can be used to slidably or moveably couple display unit 2306 to track member 2324. For example, a cam roller can be coupled to display unit 2306, and track member 2324 can be a cam follower. The cam roller engages the cam follower. For example, the cam roller can be rotatably coupled to display unit 2306 and, in some implementations, have an axis of rotation that is orthogonal to yaw axis 2332. The cam roller can be cylindrical and can roll along the curved surface of the cam follower to provide rotational motion about tilt axis 2326. For example, the cam roller can be held against the cam follower by walls or ridges of the cam follower. In some implementations, the cam follower (track member 2324) can be rigidly coupled to display unit 2306, and the cam roller can be rotatably coupled to tilt member 2324, such that the cam follower moves about tilt axis 2326 with display unit 2306.

The rotational motion of the display unit 2306 about tilt axis 2326 can be driven by one or more actuators, e.g., motors. In some implementations, a rotary motor 2328 can be rigidly coupled to the sliding member 2330, and a rotating shaft of the motor 2328 can be coupled to a capstan pulley (e.g., similar to capstan pulley 2222 shown in FIG. 22). A cable can be coupled between the first end and the second end of track member 2324 and run along the side of the track member 2324 facing motor 2328 and base support 2302 such that the track member 2324 functions as a capstan drum. The cable is wrapped around the capstan pulley that is connected to the motor shaft (e.g., similar to capstan drive mechanism described with respect to FIG. 22). In some implementations, two cables can be used instead of the cable, e.g., a first cable having a first end attached to a first end of track member 2324 first end and a second end attached to the capstan pulley, and a second cable having a first end attached to a second end of track member 2324 and a second end attached to the capstan pulley, where the two cables are routed along the side surface of the track member 2324.

With this capstan drive mechanism, the motor 2328 can be controlled to rotate the capstan pulley in either direction and move the cable(s), which pulls display unit 2306 along track member 2324 in a corresponding direction. The motor 2328 can be controlled by control signals from a control circuit (e.g., control system) to move display unit 2306 about tilt axis 2326 to a particular orientation in the tilt degree of freedom 2327. Other implementations can use different drive mechanisms to move display unit 2306 along track member 2324.

In some implementations, display unit 2306 is rotationally coupled to the sliding member 2330 and can be rotated with respect to the sliding member 2330 (and with respect to the track member 2324, arm support 2304, and base support 2302) about a yaw axis 2332. For example, this can be lateral or left-right rotation from the point of view of a user viewing images of display unit 2306 via viewports 2323. In the example of FIGS. 23-25, display unit 2306 is coupled to the sliding member 2330 by a rotary mechanism which can be a track mechanism. For example, in some implementations, the track mechanism includes a curved track bearing that includes a curved track 2334, and curved track 2334 is coupled to display unit 2306 and the curved track 2334 slidably engages a groove member that is rigidly coupled to the sliding member 2330, e.g., similarly operating as described above for FIGS. 3 and 22. This allows the display unit 2306 to rotate about yaw axis 2332 in a rotary (yaw) degree of freedom 2333 by moving the curved track 2334 through a groove of the groove member. In some implementations, a curved track is coupled to sliding member 2330 and a groove member is coupled to display unit 2306, and the groove member engages and slides along the length of the curved track to allow the rotary movement of the display unit 2306 about yaw axis 2332. In some implementations, the groove member can be about as long as the width of sliding member 2330 and/or include at least a portion of a loop through which the curved track 2334 slides.

In some implementations, curved track 2334 is a curved rail that slidably engages a groove member as described. In some implementations, a different mechanism can be used. In some examples, curved track 2334 can be a curved cam follower that engages a cam roller. For example, the cam roller can be rotatably coupled to display unit 2306 and, in various implementations, have an axis of rotation that is orthogonal to the yaw axis 2332, or parallel to the yaw axis 2332. For example, the cam roller can be cylindrical and can roll along the curved surface of the cam follower that is rigidly coupled to sliding member 2330. For example, the cam roller can be held against the cam follower by walls or ridges of the cam follower. In some implementations, the cam follower can be rigidly coupled to the display unit 2306, and the cam roller can be rotatably coupled to sliding member 2330.

The curvature (e.g., radius) of the curved track 2334 and/or groove member is selected to provide the yaw axis 2332 at a particular distance from a user-facing side of the display unit 2306 and/or from tilt axis 2326. For example, the yaw axis 2332 can be provided at a horizontal distance (parallel to horizontal degree of freedom 2322) from display unit 306 such that it approximately intersects a defined (virtual or software-defined) neck pivot axis corresponding to a pivot axis in a user's neck, as described below. The defined neck pivot axis can be used as a reference for motion of the display unit 2306 in some implementations. In the described implementation, the angle between yaw axis 2332 and a vertical axis (e.g., parallel to degree of freedom 2316) varies based on the orientation of the display unit 2306 about tilt axis 2326.

The yaw motion of the display unit 2306 about yaw axis 2332 can be driven by one or more actuators, e.g., motors. For example, motor 2340 can be a rotary motor rigidly coupled to the sliding member 2330 and having a rotatable shaft that outputs force on the display unit about yaw axis 2332 using a drive transmission. In some examples, the drive transmission can include a capstan drive mechanism, e.g., similar to the capstan drive mechanism described above with reference to FIG. 22. For example, the driven shaft of the motor 2340 can be coupled to a capstan pulley 2342. A cable 2344 can be attached to both ends of a capstan drum 2336 that is rigidly coupled to curved track 2334, where the cable is wrapped around the capstan pulley 2342, or two cables can be attached between the capstan pulley 2342 and the respective ends of capstan drum 2336. The motor 2340 rotates the capstan pulley 2342 to move the cable(s) (e.g., wind and unwind the cable(s) on the pulley), thus rotating capstan drum 2336, curved track 2334, and display unit 2306 about yaw axis 2332. In some implementations, other transmissions and/or couplings can be used to provide rotational motion of display unit 2306 about yaw axis 2332 with respect to the track member 2324 and arm support 2304, e.g., using a rotary joint similarly as described above for display system 300.

Display system 2300 thus provides display unit 2306 with vertical linear degree of freedom 2316, horizontal linear degree of freedom 2322, rotational tilt degree of freedom 2327, and rotational yaw degree of freedom 2333. For example, the vertical and horizontal degrees of freedom allow the display unit 2306 to be moved to any position within a range of motion or allowed workspace (e.g., within a vertical plane), and the tilt degree of freedom allows the display unit to be moved to a particular orientation within its range of motion (e.g., within the vertical plane or a parallel vertical plane).

A combination of coordinated movement of components of display system 2300 in at least two of these degrees of freedom allow the display unit 2306 to be positioned at various positions and orientations in its workspace, e.g., translated or rotated around a user, to facilitate a custom viewing experience for the user using the display unit. The motion of display unit 2306 in the tilt, horizontal, and/or vertical degrees of freedom allows display unit 2306 to stay close to the user's head and eyes during user head motion, and/or maintain a physical connection between the user's forehead and display unit 2306.

For example, display unit 2306 is positionable (e.g., translatable and/or rotatable) in its workspace such that eyes of the user align with the viewports of the display unit. In addition, display unit 2306 can be rotated in physical space about a defined eye pivot axis corresponding to (e.g., coincident with) an eye axis through both of a user's eyes to allow a desired vertical (e.g., up-down) eye viewing angle for the user. The display unit can be rotated about yaw axis 2332 to allow a desired yaw (e.g., left-right) viewing angle for the user. These rotations allow the display unit 2306 to be oriented comfortably for the user to view images through the viewports.

The degrees of freedom also or alternatively allow the display system 2300 to provide motion of display unit 2306 in physical space about a different defined pivot axis that can be positioned in any of various locations in the workspace of the display unit 2306. For example, the system 2300 can provide motion of display unit 2306 in physical space that corresponds to motion of a user's head when operating the display system 2300. This motion can include rotation about a defined neck pivot axis that approximately corresponds to a neck axis of a user's head at the user's neck. This rotation allows the display unit 2306 to be moved in accordance with the user's head that is directing movement of the display unit 2306, e.g., using a head input device similar to head input device 342 shown in FIGS. 3-5. Some examples of such motion of a display unit about a neck pivot axis (FIGS. 26-29) and an eye pivot axis (FIGS. 30-31) are described below.

In another example, the motion of display unit 2306 can include rotation about a defined forehead pivot axis that approximately corresponds to a forehead axis extending through the user's head at the user's forehead when the display unit 2306 is oriented, as shown, in a centered yaw rotary orientation about yaw axis 2332. In some implementations, the forehead pivot axis corresponds to a forehead axis extending through a portion of an input device of the display unit 2306 (e.g., a head input device similar to head input device 342 of FIGS. 3-5), where the portion is at or near a point of contact between the user's forehead and the input device. In some implementations, the defined forehead pivot axis can be oriented parallel to tilt axis 2326, e.g., orthogonal to the linear degrees of freedom 2316 and 2322. The defined forehead pivot axis can alternately be positioned to correspond to a different location or portion of the user's forehead or display unit.

In another example, the motion of display unit 2306 can include rotation about a defined hand input device pivot axis that approximately corresponds to an axis that extends through one or more hand input controls of display unit 2306. For example, this axis can extend through portions (e.g., the centers of grips) of both hand input controls 2340a and 2340b that are positioned on opposing (left and right) sides of display unit 2306. In some implementations, the defined hand input device pivot axis can be oriented parallel to tilt axis 2326, e.g., orthogonal to the linear degrees of freedom 2316 and 2322, similarly to the neck, eye, and forehead pivot axes described above. The hand input device pivot axis can alternately be positioned to correspond to a different location or portion of the display unit, e.g., a location of a different hand input device. For example, the hand input device pivot axis provides an axis of rotation about which the display unit 2306 can be commanded to be rotated by manipulation of the hand input devices 2340a and 2340b by the user, and/or by user manipulation of other user input devices such as head input device 342, control input devices 210 and 212, etc.

In another example, the motion of display unit 2306 in its workspace can include linear motion, e.g., based on linear translation in the vertical linear degree of freedom 2316 and horizontal linear degree of freedom 2322 and without rotational motion in the tilt and/or yaw degrees of freedom 2327 and/or 2333. In another example, the motion can include both linear motion and rotational motion. For example, display unit 2306 can be moved linearly and then rotationally in its workspace, and/or vice-versa.

During rotation of the display unit 2306 about a defined pivot axis, the movement of base support 2302 in vertical degree of freedom 2316 and/or the movement of arm support 2304 in horizontal degree of freedom 2322 can have a change in direction without a change in direction in rotation of the display unit about the defined pivot axis. For example, arm support 2304 can reverse direction as the display unit is rotated from fully up to fully down orientations. Thus, it is possible in some implementations for the base support or arm support to end up in the same position while the display unit has rotated from a first orientation to a second orientation about the defined pivot axis, where the support moves back and forth while the display unit transitions between those two orientations.

Display unit 2306 can include input devices to allow a user to provide input to manipulate the orientation and/or position of the display unit 2306 in space, and/or to manipulate other functions or components of the display system 2300 and/or larger system (e.g., teleoperated system). Some examples of input devices are described with respect to FIGS. 3-5 (e.g., hand input devices 340 and head input device 342), and such input devices can be used in display system 2300, e.g., provided on the sides and/or front facing surface of display unit 2306 in a similar manner. For example, hand input devices 2340a and 2340b can be located on display unit 2306 similarly to hand input devices 340a and 340b. User input provided from such input devices can be used to control motion of the display unit 2306 and/or displayed images and other components similarly as described above with reference to FIGS. 3-14.

In some implementations of a display system, display unit 2306 is rotatable about yaw axis 2332 in degree of freedom 2333 and one or more of the other degrees of freedom 2316, 2322, and/or 2327 are omitted from the display system 2300. For example, display unit 2306 can be rotated about yaw axis 2332 (e.g., by actuator(s) and/or manually by a user) and the display unit 2306 can be manually positioned higher and/or lower (e.g., by actuator(s) and/or manually by a user), e.g., using base support 2302 or other mechanism, and horizontal degree of freedom 2322 and/or tilt degree of freedom 2327 are omitted.

FIGS. 26-29 are side views of a portion of a display system 2600 showing rotation of a display unit about an example defined neck pivot axis, according to some implementations. Display system 2600 includes similar components to the display system 2300 of FIGS. 23-25 described above.

Figure 26:
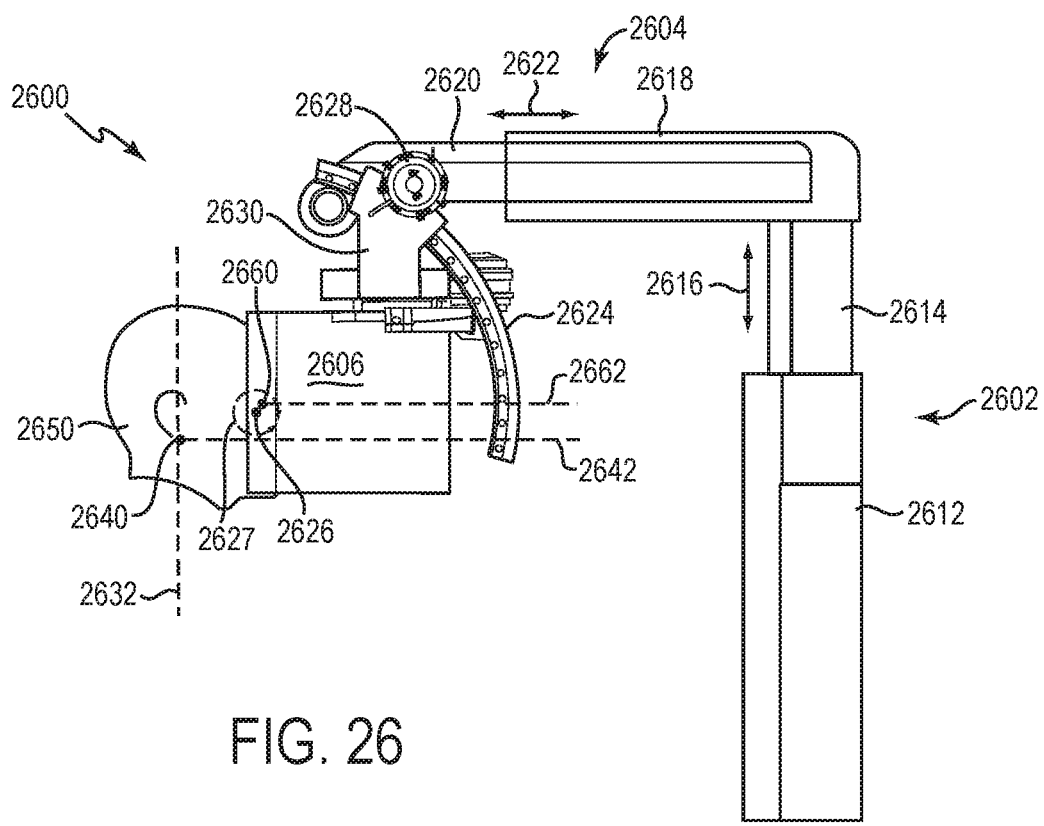
FIGS. 26-29 are side views of a portion of a display system showing rotation of a display unit about a defined neck pivot axis, according to some implementations.

In FIG. 26, display system 2600 is shown with a display unit in a first pivot orientation. Display system 2600 includes a base support 2602, an arm support 2604, and a display unit 2606. In this example, similarly to examples described above, base support 2602 includes a first base portion 2612 that is grounded and a second base portion 2614. Second base portion 2614 is linearly translatable through an interior of first base portion 2612 in a linear degree of freedom 2616. Arm support 2604 includes a first arm portion 2618 rigidly coupled to second base portion 2614, and a second arm portion 2620. Second arm portion 2620 is linearly translatable through an interior of first arm portion 2618 in a linear degree of freedom 2622.

Display unit 2606 is coupled to the second arm portion 2620 via a track member 2624 and a sliding member 2630 similarly as described in examples above with respect to FIGS. 23-25. Track member 2624 is rigidly coupled to the second arm portion 2620. Display unit 2606 is coupled to sliding member 2630, and sliding member 2630 is slidably coupled to track member 2624. Display unit 2606 rotates about tilt axis 2626 in accordance with the movement of sliding member 2630 along track member 2624.

In FIG. 26, display unit 2606 is oriented at the first pivot orientation about a defined neck pivot axis 2640 that can be approximately horizontal and can extend approximately parallel to tilt axis 2626, e.g., orthogonal to a plane defined by the degrees of freedom 2616 and 2622. In the example implementation, neck pivot axis 2640 can be positioned to intersect a head or neck of a user 2650 of display unit 2606. For example, the neck pivot axis 2640 is positioned at a location that is aligned (e.g., approximately aligned) with a pivot axis of a neck of a typical user such as user 2650 when the display unit 2606 is oriented, as shown, in a centered yaw rotary orientation about yaw axis 2632. For example, the pivot axis of the neck is a location at which a neck of a typical user operating the display unit approximately pivots. This location may be different in different users (e.g., users of different heights, different sizes of necks, etc.), and/or users may have different preferences as to where the defined neck pivot axis is located, such that in some implementations, a location determined (e.g., averaged) from preferred pivot locations of multiple users can be used for the defined neck pivot axis. In some example implementations, the defined neck pivot axis can be located at a location that is approximately aligned with a particular bone or any particular cervical vertebra of a neck of a user operating the display unit, e.g., an atlas bone or axis bone of a neck. In further examples, the defined neck pivot axis can be defined to correspond to other locations of a user's neck.

The neck pivot axis 2640 is a virtual axis that is defined based on system parameters. The movement of the base support 2602, arm support 2604, and sliding member 2630 can provide the rotation about neck pivot axis 2640. Neck pivot axis 2640 can be at different positions than shown in FIG. 26, as defined by the movement of these components in creating rotation about the desired neck pivot axis. Some implementations may allow the location of the defined neck pivot axis to be changed, e.g., by user input, to accommodate the specific preferences or physiology of particular users. In some examples, the defined neck pivot axis can be changed to a different location at which the defined neck pivot axis is parallel to tilt axis 2626 (such as a different location in which the axis is orthogonal to a vertical plane defined by the degrees of freedom 2616 and 2622), e.g., a new location that is up, down, forward, and/or back from a previous location in the point of view of a user. In some implementations, a stored profile or settings can be stored in association with a particular user and applied for use of the display system by that user, where the profile includes preferred locations for the defined neck pivot axis and/or defined eye pivot axis (described below), any of which can be loaded for system operation. These and other features (e.g., guiding the user to determine a defined neck pivot axis) can be similar to those described with respect to FIG. 8.

In the first pivot orientation shown in FIG. 26, for example, display unit 2606 can be in a horizontal view orientation about neck pivot axis 2640. For example, a view orientation of display unit 2606 with respect to neck pivot axis 2640 is indicated by a line 2642 that, in FIG. 26, extends horizontally through the neck pivot axis 2640. Rotation of display unit 2606 about the neck pivot axis 2640 is achieved by moving portion 2614 of the base support 2602, portion 2620 of the arm support 2604, sliding member 2630 to appropriate positions and/or orientations.

FIG. 26 also shows a defined eye pivot axis 2660. The defined eye pivot axis 2660 is positioned at a location that corresponds to (e.g., is coincident with) an eye axis that intersects the eyes of a typical user such as user 2650 that is looking through the viewports of the display unit 2606 when the display unit 2606 is oriented, as shown, in a centered yaw rotary orientation about yaw axis 2632. In some implementations, the defined eye pivot axis extends approximately parallel to tilt axis 2626, e.g., orthogonal to a plane defined by the degrees of freedom 2616 and 2622. This defined eye pivot axis can be orthogonal to the view orientation of the display unit 2606 when the display unit 2606 is oriented, as shown, in a centered yaw rotary orientation about axis 2632. A view orientation of display unit 2606 with respect to eye pivot axis 2660 is indicated by a sight line 2662 that, in FIG. 26, extends horizontally through eye pivot axis 2660. In some implementations, as shown, the tilt axis 2626 is located below the sight line 2662. Movement of the display system 2600 based on the eye pivot axis 2660 is described in greater detail below with respect to FIGS. 31 and 32. Movement of the display system 2600 about other defined pivot axes of the display unit 2606, e.g., forehead pivot axis or hand input device axis, can be similarly implemented to the movement about the neck and/or eye pivot axes.

Figure 27:
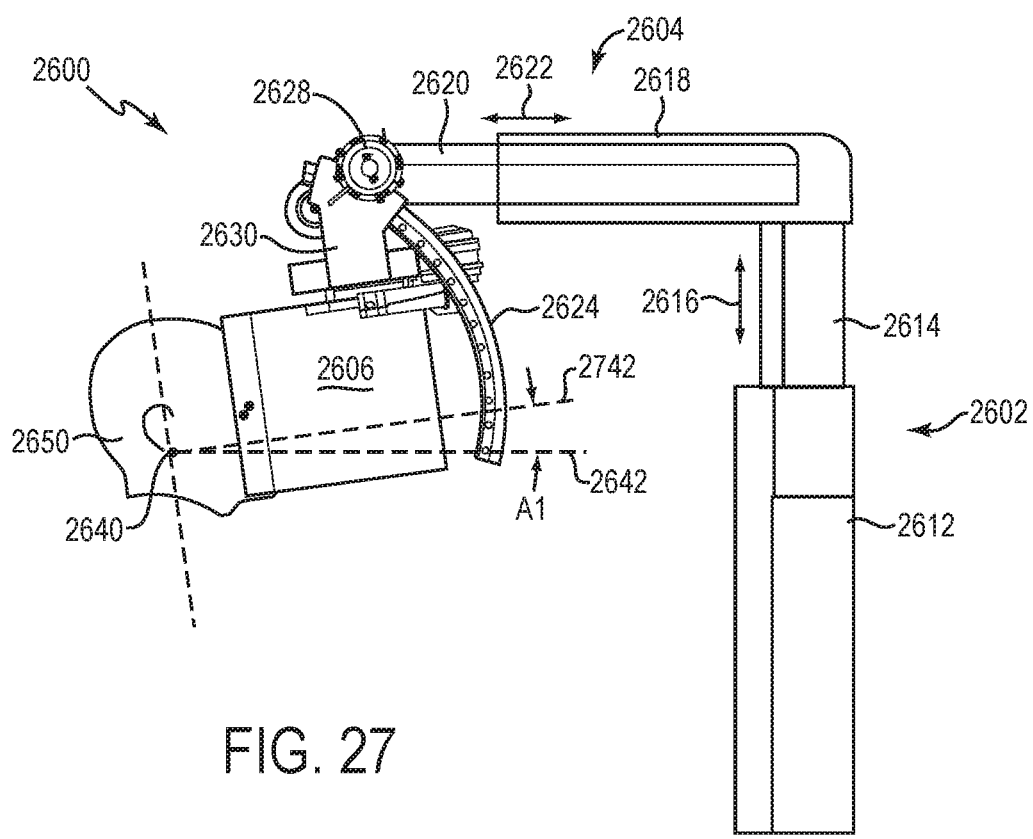

In FIG. 27, display unit 2606 is oriented at a second pivot orientation about the defined neck pivot axis 2640 to allow an "upward" view angle of the user 2650. An angle A1 is an example angle of rotation of the display unit 2606 about the neck pivot axis 2640, where angle A1 is the angle between the horizontal view orientation 2642 of the display unit 2606 and a neck-axis view orientation 2742 of display unit 2606. Display unit 2606 has been rotated about the neck pivot axis 2640 relative to the first pivot orientation shown in FIG. 26 by moving the base support 2602, arm support 2604, and sliding member 2630 to positions and/or orientations as shown. For example, relative to the first pivot orientation shown in FIG. 26, the display unit 2606 is moved to the second pivot orientation by moving the sliding tilt member 2630 upward along track member 2624 to the orientation shown (counterclockwise about axis 2626 in the viewpoint of FIG. 27), linearly translating second arm portion 2620 away from base support 2602 and toward the user 2650 to the position shown, and linearly translating second base portion 2614 upward (e.g., away from ground) to the position shown. The tilt axis 2626 is independent of the neck pivot axis 2640, since rotation of the display unit 2606 about the neck pivot axis 2640 uses rotation about the tilt axis 2626 as well as linear motion (translation) in the degrees of freedom 2622 and 2616.

In some implementations, the view angle shown in FIG. 27 is the upward (e.g., counterclockwise as shown in FIG. 27) rotational limit of the display unit 2606. In other implementations, display unit 2606 can be rotated upward (e.g., counterclockwise) by greater amounts than shown in FIG. 27 before reaching a limit to rotation in this direction.

Figure 28:
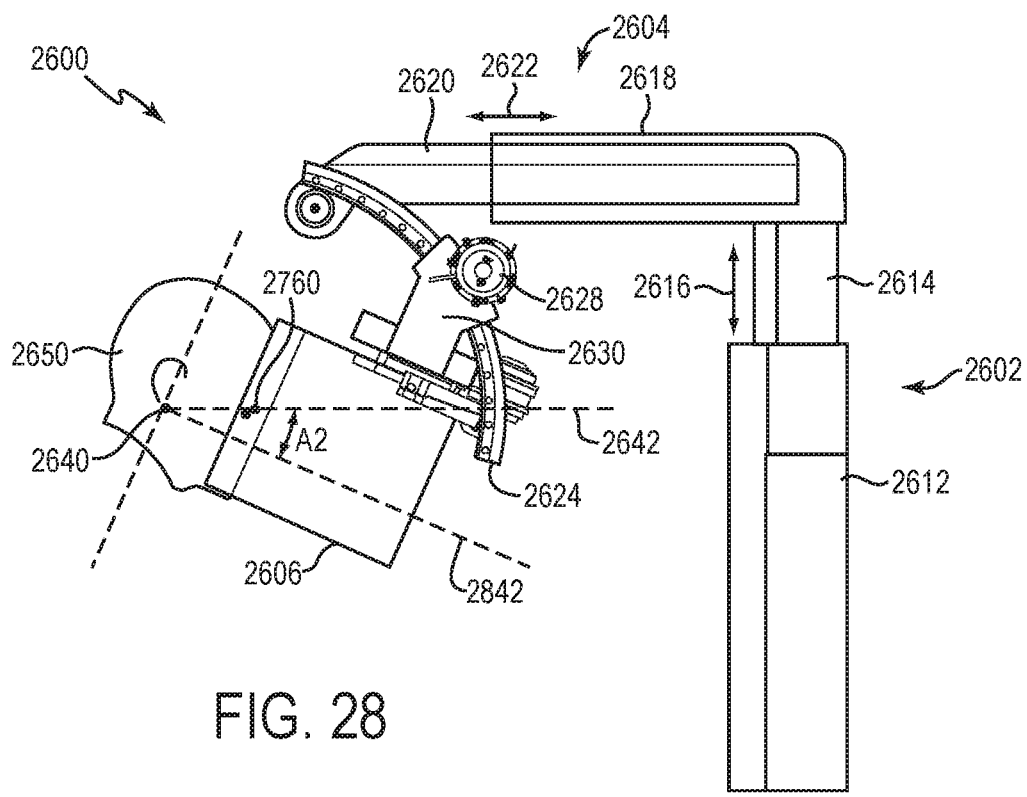

In FIG. 28, display unit 2606 is oriented at a third pivot orientation about the defined neck pivot axis 2640 to allow a "downward" view angle of the user 2650. An angle A2 is an example angle of rotation of the display unit 2606 about the neck pivot axis 2640, where angle A2 is the angle between the horizontal view orientation 2642 of the display unit 2606 and a neck-axis view orientation 2842 of the display unit. Display unit 2606 has been rotated about the neck pivot axis 2640 by moving the base support 2602, arm support 2604, and sliding member 2630 to positions and/or orientations as shown. For example, relative to the first pivot orientation shown in FIG. 26, the display unit 2606 is moved to the third pivot orientation by moving the sliding member 2630 downward to the orientation shown (clockwise about axis 2626 in the viewpoint of FIG. 28), linearly translating second arm portion 2620 in degree of freedom 2622 toward the user 2650 and away from base support 2602 to the position shown, and linearly translating second base portion 2614 downward (e.g., toward ground) to the position shown.

Figure 29:
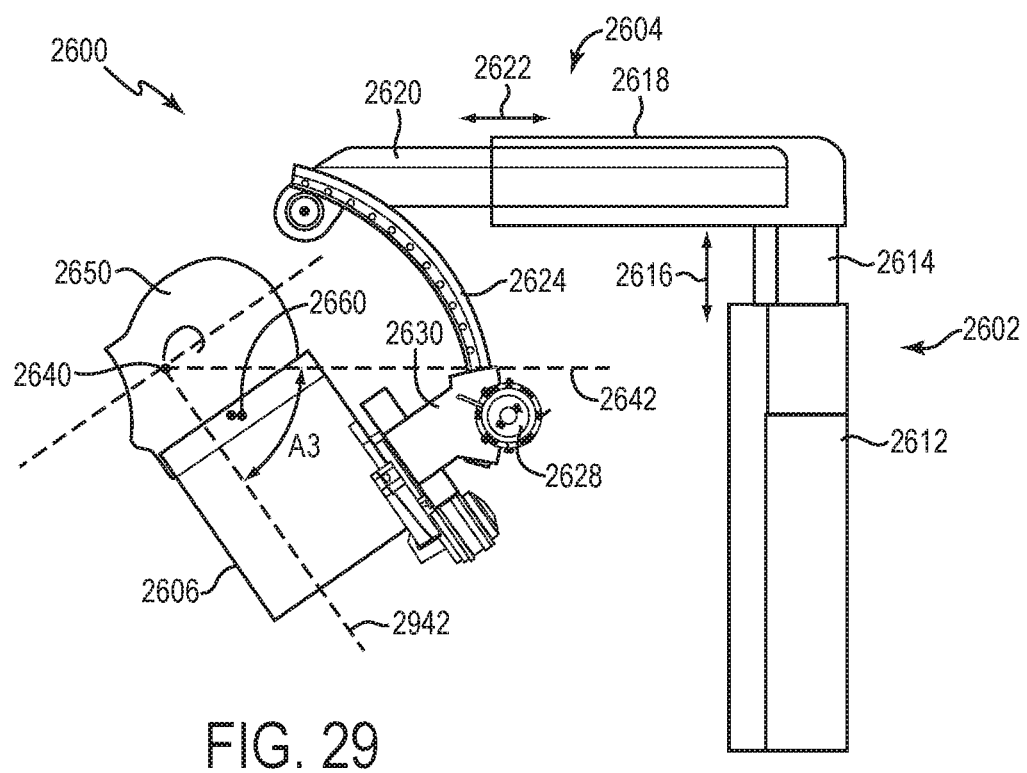

In FIG. 29, display unit 2606 is oriented at a fourth pivot orientation about the defined neck pivot axis 2640 to allow a further downward view angle of the user 2650. An angle A3 is an example angle of rotation of the display unit 2606 about the neck pivot axis 2640, where angle A3 is the angle between the horizontal view orientation 2642 of the display unit 2606 and a neck-axis view orientation 2942 of the display unit. Display unit 2606 has been rotated about the neck pivot axis 2640 by moving the base support 2602, arm support 2604, and sliding member 2630 to positions and/or orientations as shown. For example, relative to the third pivot orientation shown in FIG. 28, the display unit 2606 is moved to the fourth pivot orientation by moving the sliding member 2630 further downward to the orientation shown (clockwise about axis 2626 in the viewpoint of FIG. 29), linearly translating second arm portion 2620 in degree of freedom 2622 toward the user 2650 and away from base support 2602 to the position shown, and linearly translating second base portion 2614 downward (e.g., toward ground) to the position shown.

In the example implementations shown in FIGS. 26-29, the distance between defined neck pivot axis 2640 and tilt axis 2626 is fixed during rotation of the display unit about the defined neck pivot axis 2640.

Figure 30:
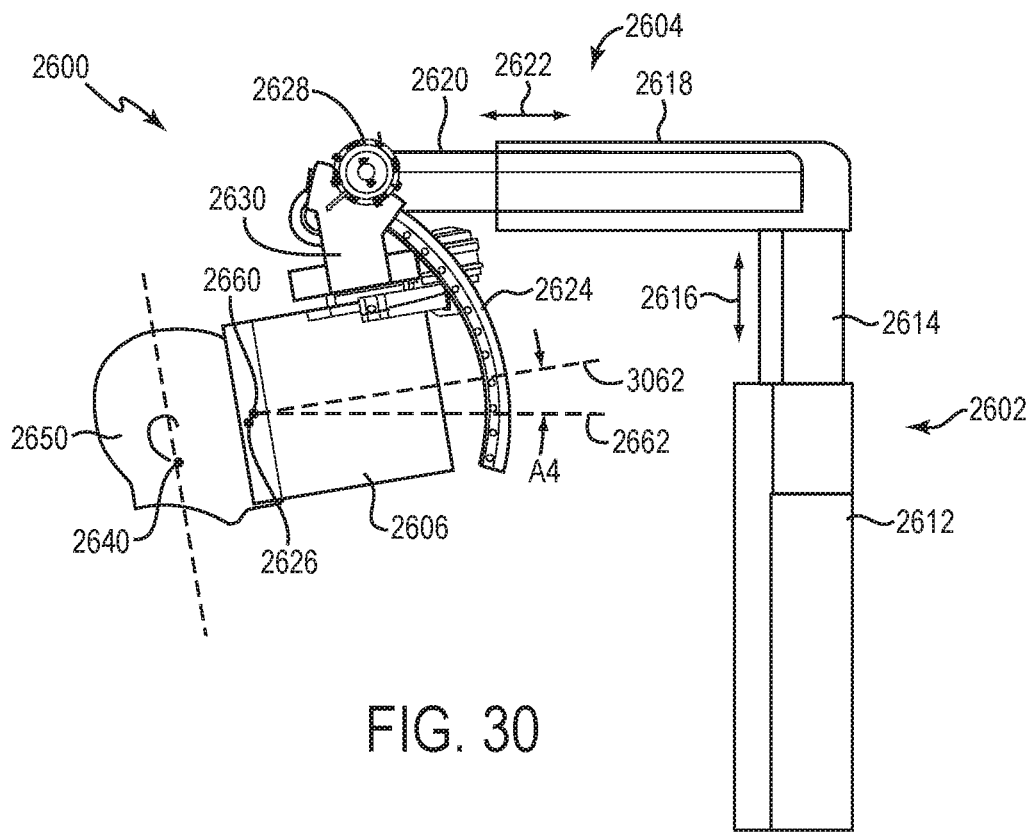
FIGS. 30 and 31 are side views of a portion of display system of FIG. 26 showing rotation of a display unit about a defined eye pivot axis, according to some implementations.
Figure 31:
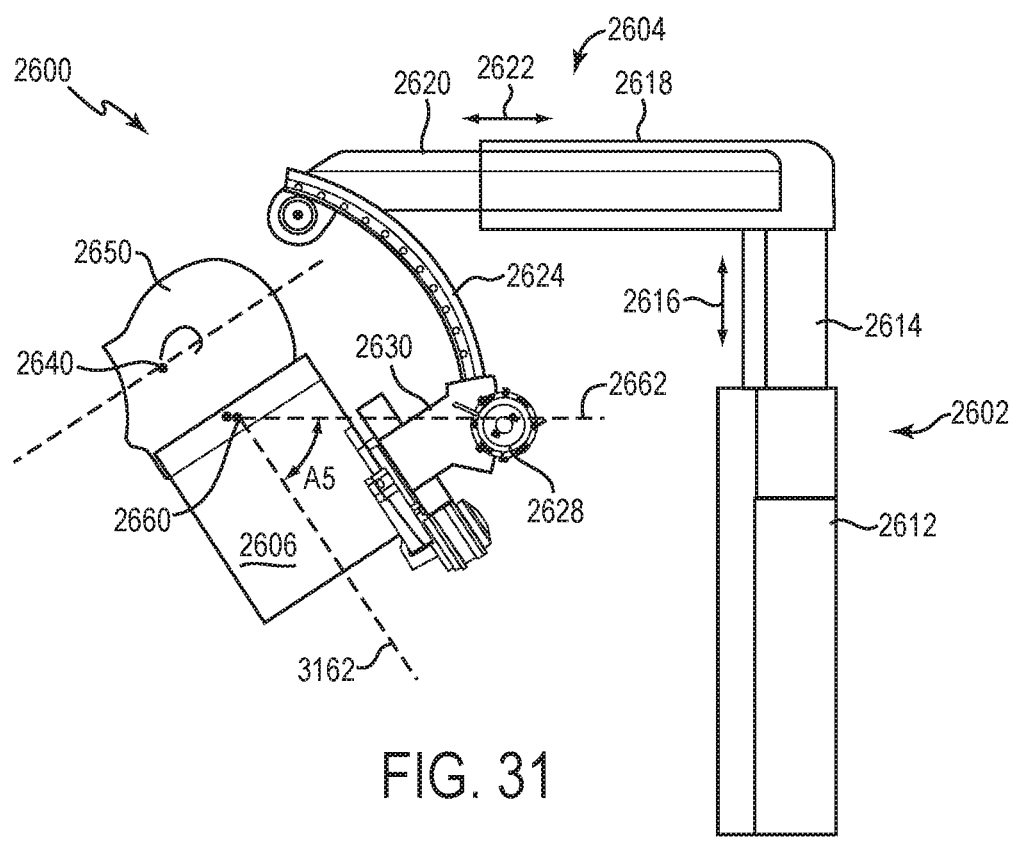

FIGS. 30 and 31 are side views of a portion of display system 2600 of FIG. 26 showing rotation of a display unit about a defined eye pivot axis, according to some implementations. Display system 2600 includes similar components to the display system 2300 described above.

In FIG. 30, display unit 2606 is oriented at a fifth pivot orientation about the defined eye pivot axis 2660 to allow an upward view angle of the user 2650. An angle A4 is an example angle of rotation of the display unit 2606 about the eye pivot axis 2660, where angle A4 is the angle between the horizontal eye-axis view orientation 2662 of the display unit 2606 (as shown in FIG. 26) and an eye-axis view orientation 3062 of the display unit. Display unit 2606 has been rotated about the eye pivot axis 2660 relative to the first pivot orientation shown in FIG. 26 by moving the base support 2602, arm support 2604, and sliding member 2630 to positions and/or orientations as shown. For example, relative to the first pivot orientation shown in FIG. 26, the display unit 2606 is moved to the fifth pivot orientation by moving sliding member 2630 upward to the angle shown (counter-clockwise about axis 2626 in the viewpoint of FIG. 30), linearly translating second arm portion 2620 toward base support 2602 and away from the user 2650 to the position shown, and linearly translating second base portion 2614 downward (e.g., toward ground) to the position shown (this movement is very small in this example). The tilt axis 2626 is independent of the eye pivot axis 2660, since rotation of the display unit 2606 about the eye pivot axis 2660 may use rotation about the tilt axis 2626 as well as linear motion (translation) in the degrees of freedom 2622 and 2616.

In FIG. 31, display unit 2606 is oriented at a sixth pivot orientation about the defined eye pivot axis 2660 to allow a downward view angle of the user 2650. An angle A5 is an example angle of rotation of the display unit 2606 about the eye pivot axis 2660, where angle A5 is the angle between the horizontal eye-axis view orientation 2662 of the display unit 2606 and an eye-axis view orientation 3162 of the display unit. Display unit 2606 has been rotated about the eye pivot axis 2660 by moving the base support 2602, arm support 2604, and member 2630 to positions and/or orientations as shown. For example, relative to the first pivot orientation shown in FIG. 26, the display unit 2606 is moved to the sixth pivot orientation by moving sliding member 2630 downward to the orientation shown (clockwise about axis 2626 in the viewpoint of FIG. 31), linearly translating second arm portion 2620 in degree of freedom 2622 away from base support 2602 and toward the user 2650 to the position shown, and linearly translating second base portion 2614 upward (e.g., away from ground) to the position shown.

In this example implementation of FIGS. 30 and 31, the eye pivot axis 2660 is close in position to the tilt axis 2626. Thus, rotation about eye pivot axis 2660 is mostly provided by rotation about tilt axis 2626 and does not require substantial movement of second arm portion 2620 and second base portion 2614. Other implementations may have a larger distance between eye pivot axis 2660 and tilt axis 2626 and require larger motions of second arm portion 2604 and second base portion 2614.

Display system 2600 (and 2300) can provide movement of a display unit about a neck pivot axis and/or eye pivot axis of a user similar to the movement shown above in FIGS. 8-14 for the display systems 300, 600 and 700 described above. In some implementations for particular defined pivot axes, display system 2600 (and 2300) can provide such movement with overall less motion and/or movement range required of the moving portions of arm support 2604 and base support 2602 than required from display systems 300, 600, and/or 700. In these examples, this is due to the tilt axis 2626 of the display unit 2606 being closer to the neck pivot axis 2640 and to the eye pivot axis 2660, allowing rotation of the display unit 2606 about tilt axis 2626 that is closer to the defined neck pivot axis or defined eye pivot axis.

Figure 32:
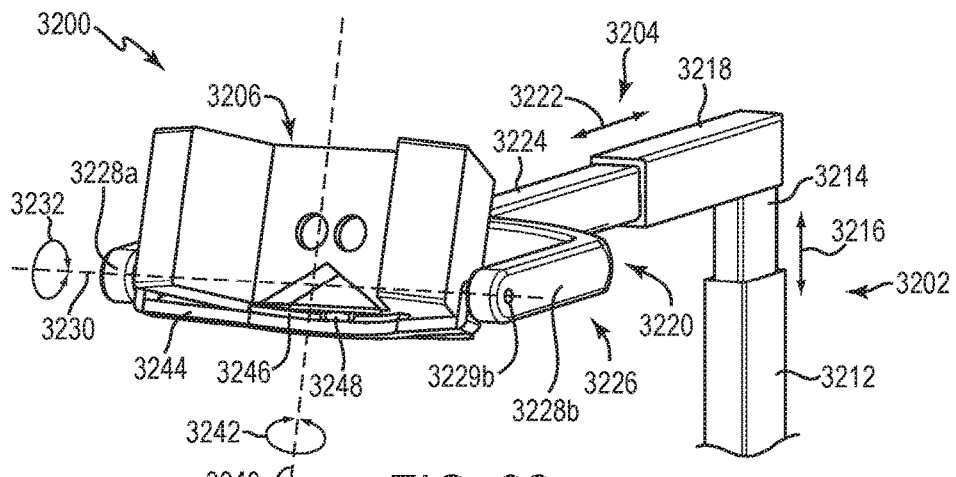
FIG. 32 is a perspective view of another implementation of a display system, according to some implementations.
Figure 33:
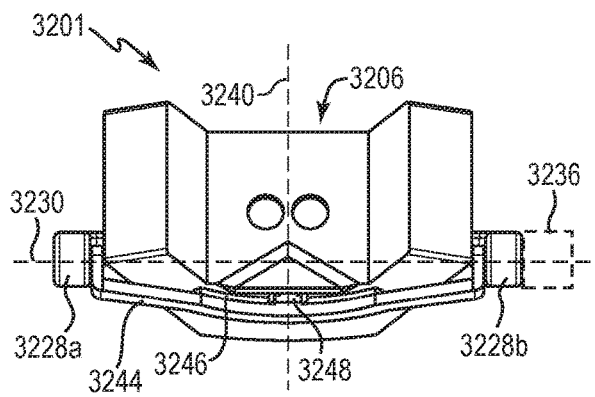
FIGS. 33-36 are front, side, top, and bottom views, respectively, of a portion of the display system of FIG. 32, according to some implementations.
Figure 34:
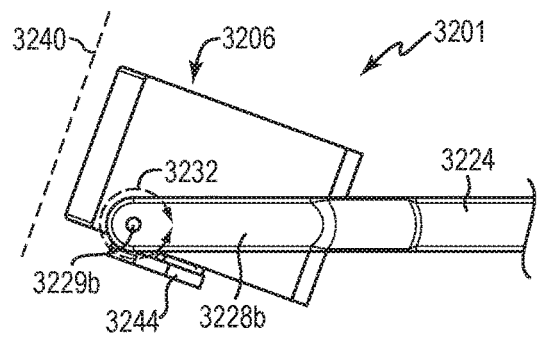
Figure 35:
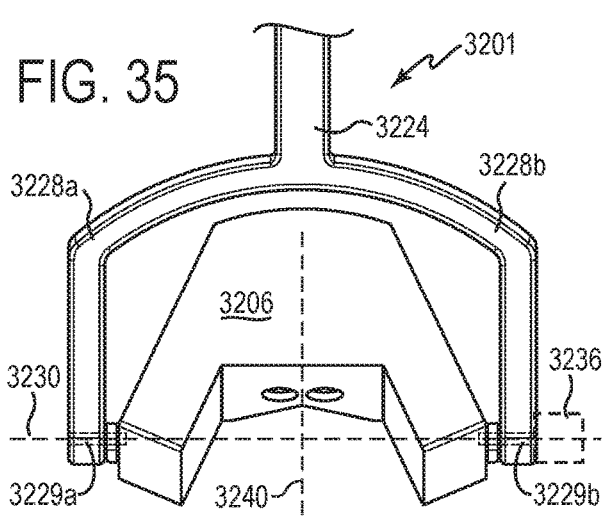
Figure 36:
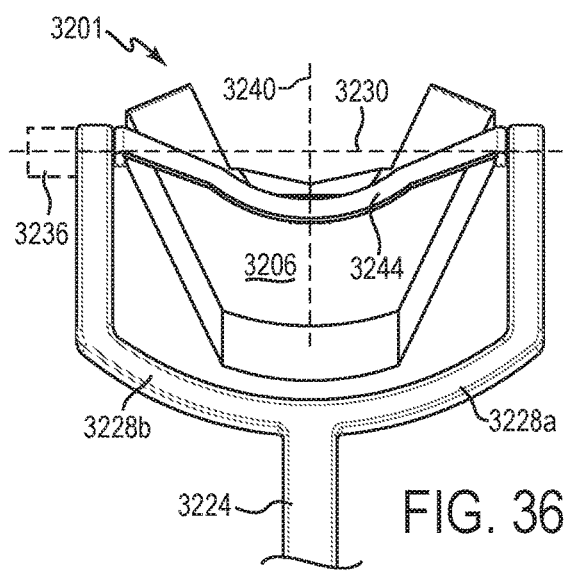

FIG. 32 is a perspective view of another implementation 3200 of a display system, and FIG. 33 is a front view, FIG. 34 is a side view, FIG. 35 is a top view, and FIG. 36 is a bottom view of a portion 3201 of the display system 3200, according to some implementations. In some examples, display system 3200 can be used in a user control system 102 of a teleoperated system as described for FIG. 1 and elsewhere herein, or can be used in other systems or as a standalone system as described above. Features of display system 3200 can be similar to those of display system 300 of FIG. 3 and/or display system 2300 as described above, unless otherwise indicated.

Display system 3200 includes a base support 3202, an arm support 3204, and a display unit 3206. Display unit 3206 is provided with multiple degrees of freedom of movement by a support linkage including the base support 3202 and arm support 3204 coupled to the base support 3202, where the display unit 3206 is coupled to the arm support 3204. In some implementations, base support 3202 and the proximal portion of arm support 3204 (coupled to base support 3202) can be similarly implemented as described above with reference to FIGS. 3-7 and 23-25.

In some examples, base support 3202 is a vertical member that is mechanically grounded, e.g., similarly as in implementations of FIGS. 3-7 and 23-25, and includes a first base portion 3212 and a second base portion 3214. The first base portion 3212 and second base portion 3214 can be linearly coupled (e.g., telescopically coupled) and allow linear translation of second base portion 3214 with respect to first base portion 3212 in a linear degree of freedom 3216, where such translation can be driven by one or more actuators, e.g., motors, e.g., similarly as described above with reference to FIGS. 15 and 16. Other implementations can use different configurations similarly as described above for implementations of FIGS. 3-7 and 23-25.

Arm support 3204 is a horizontal member that is mechanically coupled to the base support 3202. Arm support 3204 includes a first arm portion 3218 and a second arm portion 3220. First arm portion 3218 is a proximal portion of the arm support 3204 that is rigidly coupled to the second base portion 3214 of base support 3202, and the second arm portion 3220 is a distal portion of the arm support 3204 that linearly coupled to the first arm portion 3218 such that the second arm portion 3220 is linearly translatable with respect to the first arm portion 3218 in a linear degree of freedom 3222. In some examples, a proximal portion 3224 of second arm portion 3220 is telescopically coupled to first arm portion 3218, e.g., the portions 3218 or 3220 are telescoping portions similarly as described in implementations of FIGS. 2-7 and 23-25. In the example of FIGS. 32-36, proximal portion 3224 of second arm portion 3220 is linearly translatable through an interior of first arm portion 3218 in linear degree of freedom 3222. The linear translation of the second arm portion 3220 with respect to the first arm portion 3218 can be driven by one or more actuators, e.g., motors, some examples of which are described with respect to FIGS. 17 and 18. Other implementations can use different configurations similarly as described above for implementations of FIGS. 3-7 and 23-25. In some implementations, first arm portion 3218 and second base portion 3214 can be considered to be a single piece, e.g., a middle support or middle portion that is coupled between first base portion 3212 and second arm portion 3220, similarly as described above.

In some examples as shown, arm support 3204 extends along a horizontal axis that is orthogonal to a vertical axis along which base support 3202 extends. In some examples, base support 3202 and arm support 3204 are fixed in orientation with respect to each other, e.g., they translate but do not change orientation with respect to each other. In some examples, a vertical axis extending through the base support 3202 extends through the first arm portion 3218 of the arm support 3204. In various implementations, arm support 3204 can extend at various heights and/or configurations, e.g., below a user's head or body, at the height of the user's head, above a user's head, etc. Some implementations can provide components in display system 3200 to reduce vibration in the supports and members of the display system 3200, similarly as described for FIGS. 3-5.

Second arm portion 3220 includes proximal portion 3224 that is coupled to the first arm portion 3202 as described above, and a yoke portion 3226 that is rigidly coupled to the proximal portion 3224. In the described implementations, yoke portion 3226 includes two yoke members 3228a and 3228b (collectively referred to as 3228) which extend within a horizontal plane that is orthogonal to a plane defined by the proximal portion 3224 and the base member 3202. Yoke members 3228 extend in approximately opposing directions from the proximal portion 3224 and then in parallel directions parallel to the proximal portion 3224, forming an approximate U-shape as shown. The yoke members may extend in various directions in other implementations, e.g., in an approximate V-shape or other shapes.

Display unit 3206 includes a display device that can be similar as described for the implementations of FIGS. 3-7 and/or FIGS. 23-25. Display unit 3206 is rotationally coupled to arm support 3204. In these implementations, display unit 3206 is positioned between and rotationally coupled to the distal ends of the yoke members 3228. In this example, display unit 3206 is coupled to a crossbeam 3244 that is rotatably coupled to the yoke members 3228. For example, a shaft 3229a of crossbeam 3244 is rotatably coupled to yoke member 3228a, and a shaft 3229b of crossbeam 3244 is rotatably coupled to yoke member 3228b. As crossbeam 3244 rotates, display unit 3206 rotates with the crossbeam. In some implementations, shafts 3229 can be rigidly coupled to display unit 3206 without use of crossbeam 3244, e.g., if yaw motion is not being implemented for display unit 3206.

Display unit 3206 is rotatable in a rotary (tilt) degree of freedom 3232 about a tilt axis 3230 with respect to arm support 3204 and base support 3202. Tilt axis 3230 extends through the distal ends of yoke members 3228 and, for example, can be aligned with or parallel to the lengths of shafts 3229a and 3229b. In some implementations, tilt axis 3230 is oriented orthogonally to the plane defined by linear degrees of freedom 3216 and 3222 provided to the display unit 3206 by base support 3202 and arm support 3204. For example, tilt degree of freedom 3232 can be provided in a vertical plane that is the same as, or is parallel to, the vertical plane in which the degrees of freedom 3216 and 3222 are provided by base support 3202 and arm support 3204. In some implementations, base support 3202 and arm support 3204 can be considered to be a support linkage having display unit 3206 coupled at the distal end of the support linkage.

Display unit 3206 is moveable in two linear degrees of freedom provided by the linear translation of the second base portion 3214 and second arm portion 3220. For example, these linear degrees of freedom can be provided within a vertical plane. In some examples, as shown, the vertical plane can be defined by the base support 3202 and proximal portion 3224 of arm support 3204.

Display unit 3206 can be rotated about a defined pivot axis based on translation provided by first arm portion 3214 and second arm portion 3220, and by rotation about tilt axis 3230 allowed by the rotational coupling of the display unit 3206 to the yoke portion 3226. Rotation about a defined pivot axis can be similar to such rotation described above for implementations of FIGS. 3-7 and 23-25 and is further described with respect to FIG. 39.

The rotational motion of the display unit 3206 about tilt axis 3230 can be driven by one or more actuators, e.g., motors. In some implementations, a rotary motor 3236 (shown in FIGS. 33, 35, and 36 in dotted lines) can be rigidly coupled to one of the yoke members 3228 (or a respective motor coupled to each yoke member 3228), and a rotating shaft of the motor 3236 can be coupled to crossbeam 3244 (e.g., one of shafts 3229) that is coupled to the display unit 3206. In some implementations, a drive mechanism can be coupled to motor 3236, e.g., a gear mechanism or a capstan mechanism similar to capstan mechanism shown in FIG. 22. In an example capstan mechanism, a capstan drum is coupled to the driven shaft 3229 (or elsewhere on crossbeam 3244) and a capstan pulley is coupled to the shaft of motor 3236, with one or more cables coupled between drum and pulley. The motor 3236 can be controlled by control signals from a control circuit (e.g., control system) to move crossbeam 3244 and display unit 3206 about tilt axis 3230 to a particular orientation in the tilt degree of freedom 3232.

In some implementations, display unit 3206 is additionally rotatably coupled to the yoke portion 3226 of arm support 3204 to allow rotation of the display unit 3606 about a yaw axis 3240 in a yaw degree of freedom 3242 with respect to arm support 3204 and base support 3202. For example, this can be lateral or left-right rotation from the point of view of a user viewing images of display unit 3206, e.g., via viewports. In the example of FIGS. 32-36, display unit 3206 is coupled to the yoke portion 3226 by a rotary mechanism which can be a track mechanism. In some implementations, the track mechanism can be similar to the track mechanisms described above in implementations that provide yaw axis movement. For example, the track mechanism can include crossbeam 3244 and a curved track bearing that includes a curved track 3246. Curved track 3246 slidably engages a groove member 3248, e.g., operating similarly as described above for FIGS. 3 and 22. Display unit 3206 moves along a curved path constrained by the curved track 3246, causing display unit 3206 to rotate about yaw axis 3240 in rotary degree of freedom 3242. Additional examples are described below with respect to FIGS. 37 and 38. For example, curved track 3246 can be rigidly coupled to crossbeam 3244 (which is rigidly coupled to yoke portion 3226 with respect to the yaw degree of freedom), and groove member 3248 can be rigidly coupled to display unit 3206. Alternatively, a groove member can be rigidly coupled to crossbeam 3244 and the curved track can be rigidly coupled to display unit 3206. Additional groove members can be provided along the length of the curved track 3246 in some implementations.

In some implementations, a different mechanism can be used to provide rotation of display unit 3206 about yaw axis 3240. In some examples, curved track 3246 can be a curved cam follower that engages a cam roller, similarly as described above for yaw movement implementations in FIGS. 3-5 and/or 23-25.

The curvature (e.g., radius) of the curved track 3246 and/or groove member 3248 is selected to provide the yaw axis 3240 at a particular distance from a user-facing side of the display unit 3206 and/or from tilt axis 3230. For example, the yaw axis 3240 can be provided at a horizontal distance (parallel to horizontal degree of freedom 3222) from display unit 3206 such that it approximately intersects a defined (virtual or software-defined) neck pivot axis corresponding to a pivot axis in a user's neck, as described below. The defined neck pivot axis can be used as a reference for motion of the display unit 3206 in some implementations. In the described implementation, the angle between yaw axis 3240 and a vertical axis (e.g., parallel to degree of freedom 3216) varies based on the orientation of the display unit 3206 about tilt axis 3230.

The yaw motion of the display unit 3206 about yaw axis 3240 can be driven by one or more actuators, e.g., motors. For example, a rotary motor (not shown) can be rigidly coupled to the display unit 3206 and can include a rotatable shaft that outputs force on display unit 3206 about yaw axis 3240 using a drive transmission, e.g., a capstan drive mechanism, gear mechanism, etc. In some examples, the drive transmission can include a capstan drive mechanism, e.g., similar to the capstan drive mechanism described above with reference to FIG. 22. For example, the driven shaft of the motor can be coupled to a capstan pulley and a cable can be attached to both ends of a capstan drum that is rigidly coupled to curved track 3246, where the cable is wrapped around the capstan pulley (or two cables can be attached between the capstan pulley and the respective ends of capstan drum). The motor rotates the capstan pulley to move the cable(s) (e.g., wind and unwind the cable(s) on the pulley), thus rotating the capstan drum, curved track 3246, and display unit 3206 about yaw axis 3240. In some implementations, the motor and/or drive transmission can be at least partially located within a housing of display unit 3206. For example, the capstan drum can be positioned on a side of track member 3244 or crossbeam 3244 that is opposite to the user position, and the capstan pulley can be placed adjacent to the capstan drum further from the user position. In some implementations, other transmissions and/or couplings can be used to provide rotational motion of display unit 3206 about yaw axis 3240 with respect to the track member 3244 and arm support 3204.

Display system 3200 thus provides display unit 3206 with vertical linear degree of freedom 3216, horizontal linear degree of freedom 3222, rotational tilt degree of freedom 3232, and rotational yaw degree of freedom 3242. For example, the vertical and horizontal degrees of freedom allow the display unit 3206 to be moved to any position within a range of motion or allowed workspace (e.g., within a vertical plane), and the tilt degree of freedom allows the display unit to be moved to a particular orientation within its range of motion (e.g., within the vertical plane or a parallel vertical plane).

A combination of coordinated movement of components of display system 3200 in at least two of these degrees of freedom allow the display unit 3206 to be positioned at various positions and orientations in its workspace, e.g., translated or rotated around a user, to facilitate a custom viewing experience for the user, similarly as described above for the implementations of FIGS. 3-7 and/or 23-25. Further, the degrees of freedom of the display unit 3206 also or alternatively allow the display system 3200 to provide motion of display unit 3206 in physical space about a defined pivot axis that can be positioned in any of various locations in the workspace of the display unit 2306, similarly as described above, e.g., an eye pivot axis, a forehead pivot axis, a neck pivot axis, etc.).

Display unit 3206 can include input devices to allow a user to provide input to manipulate the orientation and/or position of the display unit 3206 in space, and/or to manipulate other functions or components of the display system 3200 and/or larger system (e.g., teleoperated system). Some examples of input devices are described with respect to FIGS. 3-5 (e.g., hand input devices 340 and head input device 342), and such input devices can be used in display system 3200, e.g., provided on the sides and/or front facing surface of display unit 3206 in a similar manner. User input provided from such input devices can be used to control motion of the display unit 3206 and/or displayed images and other components similarly as described above with reference to FIGS. 3-14.

In some implementations of a display system, display unit 3206 is rotatable about yaw axis 3240 in degree of freedom 3242 and one or more of the other degrees of freedom 3216, 3222, and/or 3232 are omitted from the display system 3200. For example, display unit 3206 can be rotated about yaw axis 3240 (e.g., by actuator(s) and/or manually by a user) and the display unit 3206 can be manually positioned higher and/or lower (e.g., by actuator(s) and/or manually by a user), e.g., using base support 3202 or other mechanism, where horizontal degree of freedom 3222 and/or tilt degree of freedom 3232 are omitted.

Figure 37:
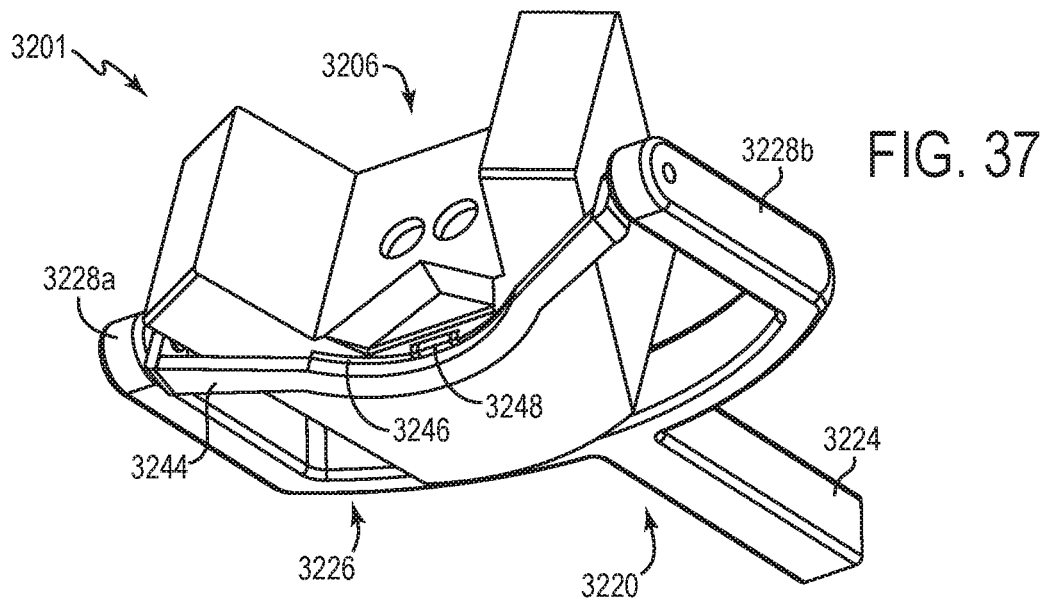
FIGS. 37 and 38 are perspective views of a portion of the display system of FIG. 32, according to some implementations.
Figure 38:
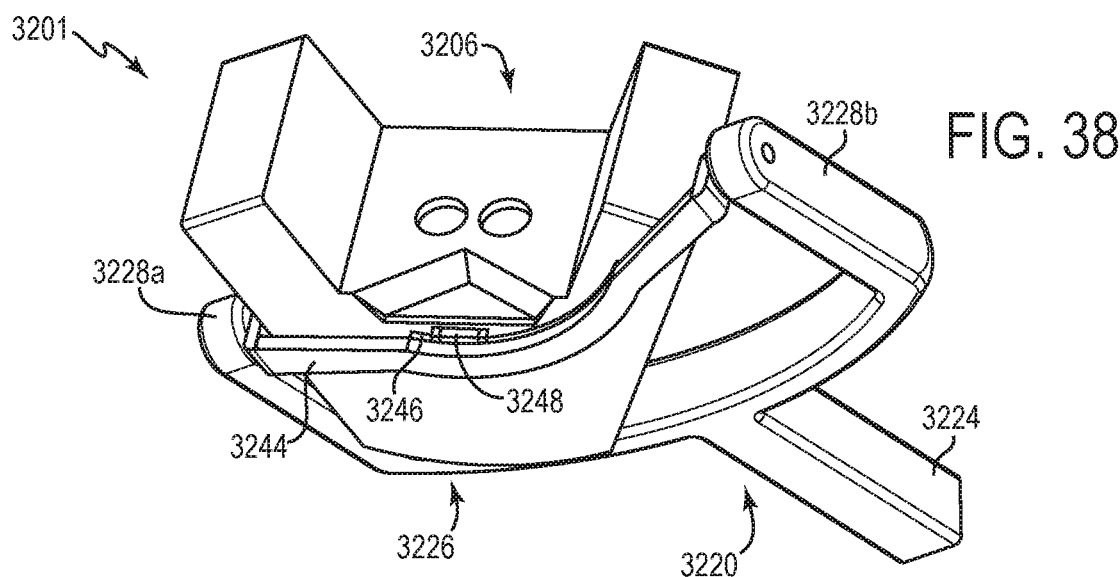

FIGS. 37 and 38 are perspective views of portion 3201 of the display system 3200 shown in FIG. 32. A perspective view of the bottom of the yoke portion 3226 and display unit 3206 is shown.

In FIG. 37, display unit 3206 is shown at a centered yaw orientation about the yaw axis 3240. For example, groove member 3248 is rigidly coupled to display unit 3206 and is centered along the curved length of the track member 3246.

In FIG. 38, display unit 3206 is shown at an orientation about the yaw axis 3240 that is changed with respect to FIG. 37. For example, groove member 3248 has been moved along the track member 3246, causing display member 3206 to be moved left, e.g., clockwise about the yaw axis 3240 if viewed from the bottom of display unit 306. As shown, track member 3246 can have a curved length that provides the display member 3206 with a limited rotational range within the space between the yoke members 3228, such that the display member 3206 can rotate about yaw axis 3240 without impacting or contacting the yoke members 3228. For example, to enable this limited rotational yaw range, the curved track can extend across (or be provided as) a central portion of crossbeam 3244. In this example, the curved track does not extend outside of the central portion, preventing groove member 3248 from moving outside that central portion. In some implementations, stops can be positioned at ends of the track member 3246 to prevent movement of groove member 3248 beyond the length of the track member 3246.

Figure 39:
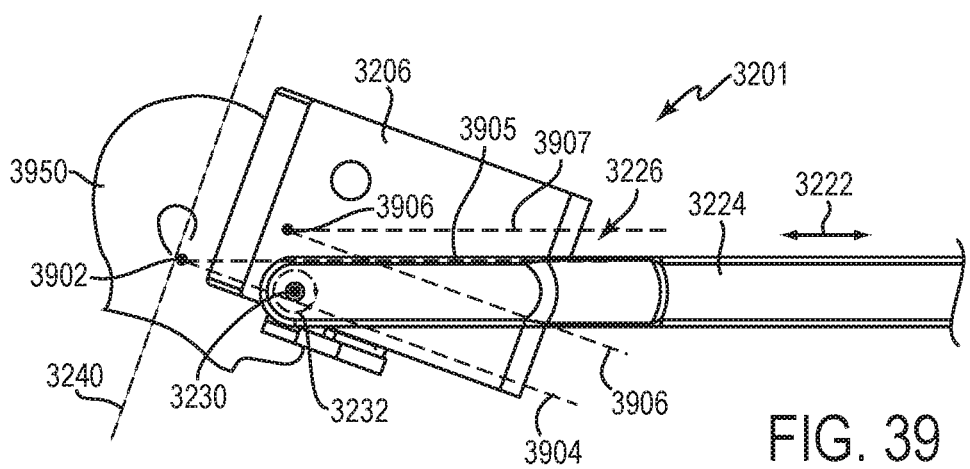
FIG. 39 is a side view of a portion of the display system of FIG. 32 showing defined pivot axes, according to some implementations.

FIG. 39 is a side view of portion 3201 of display system 3200 of FIG. 32, showing rotation of a display unit used by a user, according to some implementations. In FIG. 39, display unit 3206 is in a pivot orientation about a defined neck pivot axis 3902 that can be approximately horizontal and can extend approximately parallel to tilt axis 3230, e.g., orthogonal to a plane defined by the degrees of freedom 3216 and 3222. In the example implementation, neck pivot axis 3230 can be positioned to intersect a head or neck of a user 3950 of display unit 3206. For example, the neck pivot axis 3902 can be similar to neck pivot axis 840 or 2640 described above. The movement of the base support 3202, arm support 3204, and display unit 3206 about tilt axis 3230 can provide the rotation about neck pivot axis 3902. Neck pivot axis 3920 can be at different positions than shown in FIG. 39, as defined by the movement of these components in creating rotation about the desired neck pivot axis. These and other features (e.g., guiding the user to determine a defined neck pivot axis) can be similar to those described with respect to FIG. 8.

A view orientation of display unit 3206 with respect to neck pivot axis 3902 is indicated by a line 3904 that, in FIG. 39, extends through the neck pivot axis 3902 and is oriented to provide a downward angle with reference to a horizontal line 3905 in this example. Rotation of display unit 3206 about the neck pivot axis 3902 is achieved by moving portion 3214 of the base support 2602, portion 3220 of the arm support 2604, and display unit 3206 to appropriate positions and/or orientations. This movement can be similar in principle to the movement described with respect to FIGS. 6-11 and/or 26-29, although one or more movement directions and magnitudes may be different due to the different position of the tilt axis 3230.

FIG. 39 also shows a defined eye pivot axis 3906. The defined eye pivot axis 3906 is positioned at a location that corresponds to (e.g., is coincident with) an eye axis that intersects the eyes of a typical user such as user 3950 that is looking through viewports or at a display device of the display unit 3206 when the display unit 3206 is oriented, as shown, in a centered yaw rotary orientation about yaw axis 3240. In some implementations, the defined eye pivot axis extends approximately parallel to tilt axis 3230, e.g., orthogonal to a plane defined by the degrees of freedom 3216 and 3222. This defined eye pivot axis can be orthogonal to the view orientation of the display unit 3206 when the display unit 3206 is oriented, as shown, in a centered yaw rotary orientation about yaw axis 3240. A view orientation of display unit 3206 with respect to eye pivot axis 3906 is indicated by a sight line 3908 that, in FIG. 26, extends through eye pivot axis 3906 and is oriented to provide a downward view angle with reference to a horizontal sight line 3907 in this example. Movement of display unit 3906 about defined eye pivot axis 3906 can be similar in principle to the movement described with respect to FIGS. 12-14 and/or 30-31, although one or more movement directions and magnitudes may be different due to the different position of the tilt axis 3230. Movement of the display system 3200 about on other defined pivot axes of the display unit 3206, e.g., forehead pivot axis or hand input device axis, can be similarly implemented to the movement about the neck and/or eye pivot axes.

Display system 3200 can position the tilt axis 3230 closer to some defined pivot axes than in other implementations, e.g., implementations such as display system 300, 600, and 700 of FIGS. 3-7. In some implementations for particular defined pivot axes, display system 3200 can provide movement of display unit 3206 with overall less motion and/or movement range required of the moving portions of arm support 3204 and base support 3202 than required from display systems 300, 600, and/or 700. In these examples, this is due to the tilt axis 3230 of the display unit 3206 being closer to the neck pivot axis 3240 and to the eye pivot axis 3260, allowing rotation of the display unit 3206 about tilt axis 3226 that is closer to the defined neck pivot axis or defined eye pivot axis.

FIG. 40 is a perspective view of an example device portion 4000 of a control input device which can be used in one or more implementations described herein. In some implementations, device portion 4000 can be used as a portion of control input device 210 or 212 as described above with reference to FIGS. 1 and 2, which can be used with any of the various display system implementations described herein. In some implementations, the device portion 4000 includes one or more gimbal mechanisms.

In some implementations, device portion 4000 can be a mechanically grounded controller. For example, the device portion 4000 can be coupled to a mechanical linkage that is coupled to the ground or an object connected to ground, providing a stable platform for the use of the device portion 4000.

Device portion 4000 includes a handle 4002 which is contacted by a user to manipulate the control input device. In this example, the handle 4002 includes two grips that each include a finger loop 4004 and a grip member 4006 (grip members 4006a and 4006b). The two grip members 4006 are positioned on opposite sides of a central portion 4003 of the handle 4002, where the grip members 4006 can be grasped, held, or otherwise contacted by a user's fingers. Each finger loop 4004 is attached to a respective grip member 4006 and can be used to secure a user's fingers to the associated grip member 4006. Finger contacts 4005 can be connected or formed at the unconnected end of the grip members 4006a and 4006b to provide surfaces to contact the user's fingers.

Each grip member 4006 and finger loop 4004 can be moved in an associated degree of freedom 4008 (e.g., 4008a and 4008b). In some examples, the grip members 4006a and 4006b are each coupled to the central portion 4003 of the handle 4002 at respective rotational couplings, allowing rotational movement of the grip members about grip axes 4007a and 4007b, respectively, with respect to the central portion 4003. Each grip member 4006a and 4006b can be moved in an associated degree of freedom 4008a about axis 4007a and degree of freedom 4008b about axis 4007b, respectively, e.g., by a user contacting the grip members. For example, in some implementations the grip members 4006a and 4006b can be moved simultaneously in a pincher-type of movement (e.g., toward or away from each other). In various implementations, a single grip member 4006 and finger loop 4004 can be provided, or only one of the grip members 4006 can be moved in the degree of freedom 4008 while the other grip member 4006 can be fixed with reference to the handle 4002. For example, the orientations of grip members 4006a and 4006b in their degrees of freedom can control corresponding rotational orientations of an end effector or other manipulator instrument. One or more grip sensors (not shown) can be coupled to the handle 4002 and/or other components of the device portion 4000 and can detect the orientations of the grip members 4006a and 4006b in their degrees of freedom 4008. Some implementations can provide one or more active actuators (e.g., motors, voice coils, etc.) to output active forces on the grip members 4006 in the degrees of freedom 4008, or passive actuators (e.g., brakes) or springs between the grip members 4006 and the central portion 4003 of the handle 4002 to provide resistance in directions of the grips.

Handle 4002 is also provided with a rotational degree of freedom 4010 about a roll axis 4012 defined between a first end and second end of the handle 4002. The roll axis 4012 is a longitudinal axis in this example that extends approximately along the center of the central portion 4003 of handle 4002. For example, a user can rotate the grip members 4006 and central portion 4003 as a single unit around the axis 4012 with respect to a base of the controller portion 300, such as housing 4009 to provide control of a manipulator system component. One or more control input sensors (not shown) can be coupled to the handle 4002 to detect the orientation of the handle 4002 in the rotational degree of freedom 4010. Some implementations can provide one or more actuators to output forces on the handle 4002 in the rotational degree of freedom 4010.

Provided sensors can send signals describing sensed positions, orientations, and/or motions to one or more control circuits, e.g., a control system of the teleoperated system 100. In some modes or implementations, the control circuits can provide control signals to a manipulator system, e.g., manipulator system 104 to, for example, control any of various degrees of freedom of an end effector or other instrument of the manipulator system 104.

In various implementations, the handle 4002 can be provided with additional degrees of freedom. For example, a rotational degree of freedom 4020 about a controller yaw axis 4022 can be provided to the handle 4002 at a rotational coupling between an elbow shaped link 4024 and a link 4026, where the elbow shaped link 4024 is coupled to the handle 4002 (e.g., at housing 4009). In this example, controller yaw axis 4022 intersects and is orthogonal to the roll axis 4012. Additional degrees of freedom can similarly be provided. For example, link 4026 can be elbow-shaped and a rotational coupling can be provided between the other end of link 4026 and another link (not shown). A rotational degree of freedom 4028 about an axis 4030 can be provided to the handle 4002 at the rotational coupling. In some examples, the device portion 4000 can allow movement of the handle 4002 within a workspace of the user control system 102 with a plurality of degrees of freedom, e.g., six degrees of freedom including three rotational degrees of freedom and three translational degrees of freedom. One or more additional degrees of freedom can be sensed by control input sensors and/or actuated by actuators (motors, etc.) similarly as described above for the degrees of freedom 4008 and 4010. In some implementations, each additional degree of freedom of the handle 4002 can control a different manipulator degree of freedom (or other motion) of an end effector of the manipulator system 104.

Various kinematic chains, linkages, gimbal mechanisms, flexible structures, or combinations of two or more of these can be used with the device portion 4000 in various implementations to provide one or more degrees of freedom to the controller portion. Some further examples of linkages and/or gimbal mechanisms that can be used with device portion 4000 are described in U.S. Pat. No. 6,714,839 B2, incorporated herein by reference.

In the described example, handle 4002 includes one or more control switches 4050, e.g., coupled to the central portion 4003. In some implementations, the control switch 4050 can be moved to various positions to provide particular command signals, e.g., to select functions, options, or modes of the user control system and/or control input device (e.g., a controlling mode or non-controlling mode as described herein, or modes related to display system 300, 600, 700, 2300, or 3200). In some implementations, control switch 4050 can be implemented as a button, a rotary dial, a switch, or other type of input control. Control switch 4050 can use optical sensors, mechanical switches, magnetic sensors, or other types of sensors to detect positions of the switch. In some implementations, handle 4002 also includes a presence sensing system including one or more presence sensors that can detect the presence of a user's hand operating the handle and/or the hand positioned near the handle.

One or more display system features described herein can be used with other types of control input devices. For example, ungrounded control input devices can be used, which are free to move in space and disconnected from ground. In some examples, one or more handles similar to handle 4002 and/or grip members 4006 can be coupled to a mechanism worn on a user's hand and which is ungrounded, allowing the user to move grips freely in space. In some examples, the positions or orientations of the grips relative to each other and/or to other portions of the handle can be sensed by a mechanism coupling the grips together and constraining their motion relative to each other. Some implementations can use glove structures worn by a user's hand. Furthermore, some implementations can use sensors coupled to other structures to sense the grips within space, e.g., using video cameras or other sensors that can detect motion in 3D space. Some examples of ungrounded control input devices are described in U.S. Pat. No. 8,543,240 B2 (filed Sep. 21, 2010) and U.S. Pat. No. 8,521,331 B2 (filed Nov. 13, 2008), both incorporated herein by reference in their entireties.

Figure 41:
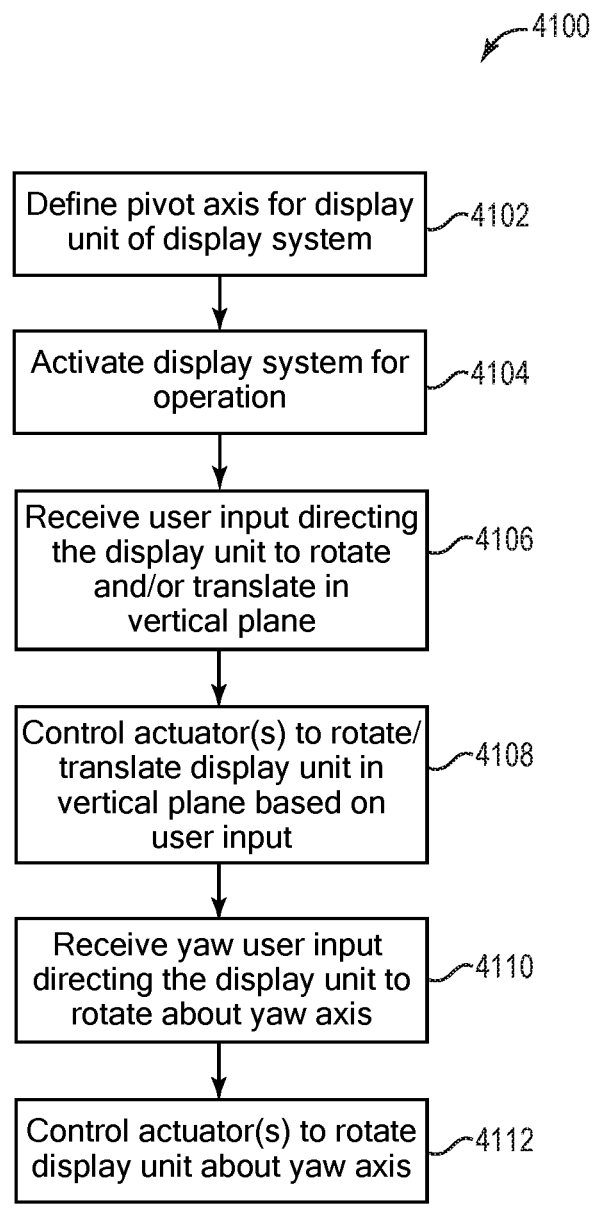
FIG. 41 is a flow diagram illustrating an example method for operating a display system including one or more features described herein, according to some implementations.

FIG. 41 is a flow diagram illustrating an example method 4100 for operating a display system including one or more features described herein, according to some implementations. In some implementations, the method can, for example, be used with an example teleoperated system or other control system in which the display system provides a displayed view in conjunction with a teleoperated manipulator system. For example, in some implementations, the display system 300 of FIG. 3, display system 600 of FIG. 6, display system 700 of FIG. 7, display system 2300 of FIG. 23, or display system 3200 of FIG. 32 can be used.

In some examples, the display system can be used in a teleoperated system such as system 100 of FIG. 1, where the display system is operated by a user who also operates one or more control input devices with his or her hand(s). A master-slave control relationship can be established between the control input device and a manipulator system, in which positions and orientations of the control input device are sensed and are transmitted to a control system, e.g., in the controller, manipulator system, and/or a separate control system. In some examples, motion of a control input device in space causes corresponding motion of a controlled instrument or other component of the manipulator system, and/or can control other functions of the manipulator system. The user input and control related to such teleoperation system components are not described in method 4100.

Other implementations of method 4100 can use a display system having one or more described features with other types of systems, e.g., non-teleoperated systems, a virtual environment implemented on a processing device and having no physical manipulator system and/or no physical subject interacting with a physical manipulator system, etc. In some implementations, the method can be partially or fully performed by a control circuit component, e.g., a control system. In some examples, the control circuit can include one or more processors, e.g., microprocessors or other control circuits, some examples of which are described below with reference to FIG. 42.

In block 4102, a pivot axis is defined for the display unit of the display system, where the display unit provides a display of images for viewing by a user (e.g., display unit 306, 606, or 706 as described herein). The display unit is to be rotated about the defined pivot axis. In some cases or implementations, the defined pivot axis coincides with a rotational axis of a mechanical component of the display system, e.g., a tilt axis 326, 626, or 726 of a tilt member as described herein. In some implementations, the defined pivot axis is a virtual axis that is based on a combination of coordinated movements of the components of the display system and does not correspond to an axis of rotation of any particular mechanical component of the display system. For example, the virtual pivot axis can be a horizontal axis such as an eye pivot axis, a neck pivot axis, forehead pivot axis, or hand input device pivot axis as described herein in various implementations.

In some implementations, the defined pivot axis can be changed to different locations in different modes or at different times of operation of the display system. In some implementations, the defined pivot axis is adjustable by the user. For example, the defined pivot axis can be determined based on user input received by the display system, e.g., via a user input device such as a keyboard, touchscreen, etc. in communication with the display system. In some examples, user input can specify one of multiple predetermined settings, where each setting defines the pivot axis at a different particular location in a workspace of the display unit of the display system. For example, one setting can define a particular eye pivot axis, and a different setting can define a particular neck pivot axis. In further examples, user input can adjust the location of the pivot axis. For example, the user input can specify to move a defined pivot axis a particular distance in space, along any of three dimensions. For example, user input can instruct a predefined eye pivot axis to be moved 5 millimeters in a vertical direction and 2 millimeters in a horizontal direction (e.g., toward a base support such as base support 302).

In block 4104, the display unit is activated for operation. In some implementations, one or more presence sensors are provided on the display system to sense a presence of the user who is in a position to operate the display system, e.g., viewing the display of the display unit. The display unit can be activated and enabled to be moveable by user input in response to detecting user presence. For example, presence sensors can detect whether a user's head is positioned close to viewing ports or windows in the display unit. In some implementations, the display unit can be used in a teleoperated system such as system 100 of FIG. 1, where the display unit is operated by a user who also operates one or more control input devices with his or her hand(s).

In block 4106, user input is received that directs the display unit to rotate and/or translate vertically, e.g., in a vertical plane. For example, user input can be received by user input devices of the display system, such as user input devices 340 and/or 342 on the display unit as described with reference to FIG. 3. The user input may also be received from user input devices provided on other components of the display system, and/or from user input devices of a system that includes or is used in conjunction with the display system, e.g., a control input device of a teleoperated system. In one example, user input can instruct actuators of the vertical base support, horizontal arm support, and tilt mechanism to output forces that moves the display unit about the defined pivot axis. In some implementations, the user input can instruct to translate the display unit in its workspace. In some implementations, the user input instructs manipulation of images displayed by the display unit, and/or manipulation of other controlled devices, in accordance with the instructed movement of the display unit.

In block 4108, one or more actuators of the display system are controlled based on the user input to rotate and/or translate the display unit in a vertical plane. For example, the actuator(s) can be controlled to rotate the display unit in the vertical plane about the pivot axis determined in block 4102, as described herein. In some implementations as described herein, a base support, arm support, and/or tilt member are moved by actuators simultaneously and in coordinated combination to cause the display unit to rotate about the defined pivot axis in accordance with the user input. In some implementations, the display unit can be translated linearly in a vertical plane based on the user input, e.g., moved based on linear movement provided by a base support and/or arm support.

In some implementations, images or user interface controls displayed by the display unit are manipulated in accordance with the user input and/or in accordance with the movement of the display unit in the vertical plane. For example, the view of a displayed image can be moved in accordance with user input and/or motion of the display unit. In additional examples, user input can manipulate views or elements of a displayed user interface, virtual environment, or other display provided by the display system. For example, user interface features such as cursors, scroll bars, lists, menus, selections of graphical elements, etc., can be moved or manipulated in accordance with the user input and/or movement of the display unit. In some examples, such a user interface can be overlaid on a displayed captured view of a work site or can be displayed to the side(s) of the captured view.

In some implementations, functions of a manipulator system can be manipulated in accordance with the user input and/or the display unit movement. For example, an actuator of a manipulator system can be controlled to move an image capture device (e.g., camera) of the manipulator system in correlation with the movement of the display unit, e.g., translating and/or rotating a camera based on corresponding motion of the display unit in its workspace. Image data is received from the image capture device and displayed by the display device of the display unit. The actuator is controlled based on commands sent to the manipulator system from the control system, where the commands are based on the user input and/or movement of the display unit. A different manipulator instrument can be controlled (e.g., via control input devices 210 and/or 212) to move at least partially simultaneously with the movement of the manipulator image capture device controlled via the display unit, such that the user can control the manipulator image capture device to change the field of view of the slave work site displayed in display unit while the user also controls the different manipulator instrument to perform tasks in a teleoperated procedure at the manipulator work site as viewed via the display unit.

Additional examples of teleoperated system functions manipulable by the user input can include, in some examples, a swap function causing control of a first manipulator arm or instrument to be swapped to a second manipulator arm or instrument; energy output for manipulator instruments; irrigation or suction at a surgical site; a clutch function to select a controlling mode and a non-controlling mode; etc.

In block 4110, yaw user input is received that directs the display unit to rotate about the yaw axis (lateral rotation axis), e.g., left or right (lateral) rotation of the display unit about a vertical axis from the user's perspective. For example, the yaw user input can be received from similar user input devices as described for block 4106, and/or from other user input devices of the display system or other system that are different from user input devices providing the user input of block 4106. In various implementations, user input can instruct the display unit to rotate left about the yaw axis, to linearly translate the display unit left, to manipulate images or user interface elements displayed by the display unit, and/or to manipulate other controlled devices.

In block 4112, one or more actuators of the display system are controlled based on the user input to rotate the display unit about the yaw axis. For example, an actuator of the track mechanism described with respect to FIGS. 3-5, FIG. 22, FIGS. 23-25, or FIGS. 32-38 can be used to rotate the display unit about yaw axis 330, 630, 730, 2332, or 3240. In one example, user input that directs rotation to the left (e.g., counterclockwise as viewed from above) causes the actuator to output force that moves the display unit counterclockwise about the yaw axis. In some implementations, images or a user interface displayed by the display unit, and/or other controlled devices, are manipulated in accordance with the movement of the display unit similarly as described for block 4108.

Blocks 4106 and 4110 can be performed in any order and/or partially or completely simultaneously, such that, e.g., user input to rotate/translate the display unit in a vertical plane can be received simultaneously with user input to rotate the display unit about the yaw axis. Similarly, blocks 4108 and 4112 can be performed in any order and/or partially or completely simultaneously based on the user input received.

The blocks 4106 to 4112 are repeated based on additional received user input that instructs the display unit to move vertically and/or about the yaw axis. Other user input may be received that deactivates the display unit operation, causes block 4102 to be performed to change the location of the defined pivot axis, or perform other functions of the display system.

The blocks and operations described in the methods disclosed herein can be performed in a different order than shown and/or simultaneously (partially or completely) with other blocks and operations, where appropriate. Some blocks and operations can be performed for one portion of data and later performed again, e.g., for another portion of data. Not all of the described blocks and operations need be performed in various implementations. In some implementations, blocks and operations can be performed multiple times, in a different order, and/or at different times in the methods.

Output such as haptic feedback on the display unit and/or visual output on a display device can be provided by the system to assist user operation of the display system and/or a teleoperated system. For example, a user interface may display warnings and/or error feedback on a display device, and/or audio output can be provided to indicate such warnings or errors. Such feedback can indicate, for example, reaching limits to the movement range of the display unit, moving the display unit such that a particular object being displayed is about to be moved out of view of the display unit, etc.

In various implementations, other types of computer-assisted teleoperated systems, in addition to surgical systems, can be used with one or more display system features described herein. Such teleoperated systems can include controlled manipulator systems of various forms. For example, submersibles, hazardous material or device disposal units, industrial applications, applications in hostile environments and worksites (e.g., due to weather, temperature, pressure, radiation, or other conditions), general robotics applications, and/or remote-control applications (e.g., remote controlled vehicle or device with a first-person view), may utilize teleoperated systems that include manipulator or slave systems for sensory transmission (conveyed visual, auditory, etc. experience), manipulation of work pieces or other physical tasks, etc., and may use mechanically grounded and/or ungrounded control input devices to remotely control the manipulator systems and a display system to view worksites of the manipulator systems. Any such teleoperated systems can be used with any of the various display system features described herein.

Figure 42:
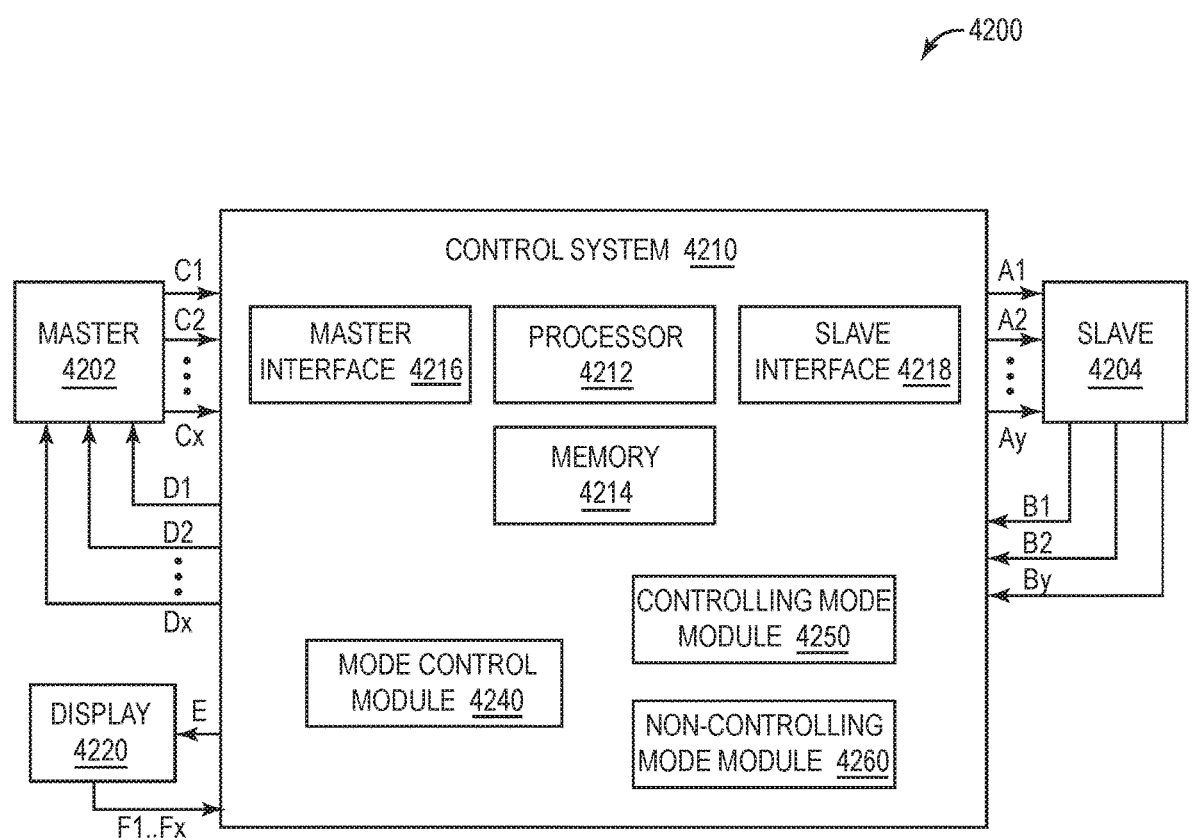
FIG. 42 is a block diagram of an example master-slave system, which can be used with one or more implementations described herein.

FIG. 42 is a block diagram of an example master-slave system 4200, which can be used with one or more implementations described herein.

As shown, system 4200 includes a master device 4202 that a user may manipulate in order to control a slave device 4204 in communication with the master device 4202. In some implementations, master device 1002 can be, or can be included in, any of user control systems described herein. In some implementations, slave device 1004 can be, or can be included in, manipulator system 104 of FIG. 1. More generally, master device block 4202 can include one or more of various types of devices providing one or more control input devices that can be physically manipulated by a user. For example, master device 4202 can include a system of one or more master control devices such as one or more hand controllers (e.g., master control devices 210 and 212 or other hand controllers described herein).

Master device 4202 generates control signals C1 to Cx indicating positions and orientations, states, and/or changes of one or more controllers in their degrees of freedom. For example, the master device 4202 can generate control signals indicating selection of input controls such as physical buttons, hand controller states, and other manipulations of the hand controller by the user. The control signals can be sent via wired connections, or wireless.

A control system 4210 can be included in the master device 4202, in the slave device 4204, or in a separate device, e.g., an intermediary device communicatively connected between master device 4202 and slave device 4204. In some implementations, the control system 4210 can be distributed among multiple of these devices.

In the example system, control system 4210 receives control signals C1 to Cx and generates actuation signals A1 to Ay, which are sent to slave device 4204. Control system 4210 can also receive sensor signals B1 to By from the slave device 4204 that indicate positions and orientations, states, and/or changes of various slave components (e.g., manipulator arm elements). These actuation and/or sensor signals can be sent via wired connections, or wireless.

Control system 4210 can include components such as a processor 4212, memory 4214, and interface hardware 4216 and 4218 such as a master interface and a slave interface for communication with master device 4202 and slave device 4204, respectively. Processor 4212 can execute program code and control operations of the system 4200, including operations related to processing sensor data from a display unit and commanding modes and components as described herein. Processor 4212 can include one or more processors of various types, including microprocessors, application specific integrated circuits (ASICs), and other electronic circuits. Memory 4214 can store instructions for execution by the processor and can include any suitable processor-readable storage medium, e.g., random access memory (RAM), read-only memory (ROM), Electrical Erasable Read-only Memory (EEPROM), Flash memory, etc. For example, the processor 4212 and memory 4214 enable control between the master control device 4202 and the slave device 4204.

The control system 4210 includes programmed instructions (e.g., a computer-readable medium storing the instructions) to implement appropriate operations and blocks of methods in accordance with aspects disclosed herein. The system may include multiple data processing circuits with one portion of the processing optionally being performed on or adjacent the slave device 4204, another portion of the processing being performed at the master device 4202, etc. Any of a wide variety of centralized or distributed data processing architectures may be employed. Similarly, the programmed instructions may be implemented as a number of separate programs or subroutines, or they may be integrated into a number of other aspects of the teleoperated systems described herein. In one embodiment, control system 4210 supports one or more wireless communication protocols such as Bluetooth, IrDA, HomeRF, IEEE 802.11, DECT, and Wireless Telemetry.

Various other input and output devices can also be coupled to the control system 4210. The output devices can include one or more display units as a component of a display system 4220. For example, display system 4220 can be similar to display system 300, 600, 700, or 2300 described herein. Display system 4220 receives command and/or data signals E from the control system 4210 to cause display of images, e.g., digital images composed of multiple pixels. The images can be generated by the control system or other system (e.g., graphical elements and animations in a user interface allowing selection of commands for a teleoperated system), and/or the images can be derived from data captured by an image capture device positioned at a slave device or other location. Display system 4220 also provides command signals F1 to Fx to the control system 4210 to control functions of the display system, including movement of a display unit (e.g., display unit 306, 606, 706, or 2306) in space as described herein. For example, the command signals F1 to Fx can be generated based on user manipulation of user input devices, as described herein, and/or based on detected events or other conditions. In some implementations, display system 4220 can enable or disable (e.g., follow or ignore) the commands F1 to Fx based on the state of the teleoperated system or control system 4210.

In this example, control system 4210 includes a mode control module 4240, a controlling mode module 4250, and a non-controlling mode module 4260. Other implementations can use other modules, e.g., a force output control module, sensor input signal module, etc. As used herein, the term "module" can refer to a combination of hardware (e.g., a processor such as an integrated circuit or other circuitry) and software (e.g., machine or processor executable instructions, commands, or code such as firmware, programming, or object code). A combination of hardware and software can include hardware only (i.e., a hardware element with no software elements), software hosted by hardware (e.g., software that is stored at a memory and executed or interpreted by or at a processor), or a combination of hardware and software hosted at hardware. In some implementations, the modules 4240, 4250, and 4260 can be implemented using the processor 4212 and memory 4214, e.g., program instructions stored in memory 4214 and/or other memory or storage devices connected to control system 4210.

Mode control module 4240 can detect when a user initiates a controlling mode and a non-controlling mode of the system, e.g., by user selection of controls, sensing a presence of a user using a master controller, sensing required manipulation of a master controller, etc. The mode control module can set the controlling mode or a non-controlling mode of the control system 4210 based on one or more control signals C1 to Cx. For example, mode control module 4240 may activate controlling mode operation if user detection module detects that a user is in proper position for use of the control input device(s) and that signals (e.g., one or more signals C1 to Cx) indicate the user has contacted the control input device(s). The mode control module 4240 may disable controlling mode if no user touch is detected on the control input device(s) and/or if a user is not in proper position for use of the control input device(s). For example, the mode control module 4240 can inform control system 4210 or send information directly to controlling mode module 4250 to prevent the controlling mode module 4250 from generating actuation signals A1 to An that move slave device 4204.

In some implementations, controlling mode module 4250 may be used to control a controlling mode of control system 4210. Controlling mode module 4250 can receive control signals C1 to Cx and can generate actuation signals A1 to Ay that control actuators of the slave device 4204 and cause it to follow the movement of master device 4202, e.g., so that the movements of slave device 4204 correspond to a mapping of the movements of master device 4202. Controlling mode module 4250 can be implemented using conventional techniques. In some implementations, controlling mode module 4250 can also be used to control forces on the master device 4202. For example, forces can be output on one or more components of the master control devices, e.g., hand grip members or mechanical links of the control input devices, using one or more control signals D1 to Dx output to actuator(s) used to apply forces to the components. Such forces can provide haptic feedback, gravity compensation, etc.

In some implementations, a non-controlling mode module 4260 may be used to control a non-controlling mode of system 4200. In the non-controlling mode, user manipulations of master device 4202 have no effect on the movement of one or more components of slave 4204. In some examples, non-controlling mode may be used when a portion of slave device 4204, e.g., a manipulator arm assembly, is not being controlled by master device 4202, but rather is floating in space and may be manually moved. For non-controlling mode, non-controlling mode module 4260 may allow actuator systems in the slave device 4204 to be freewheeling or may generate actuation signals A1 to An, for example, to allow motors in a manipulator arm to support the expected weight of the arm against gravity, where brakes in the arm are not engaged and permit manual movement of the arm.

In some implementations, non-controlling mode can include one or more other operating modes of the control system 4210. For example, a non-controlling mode can be a selection mode in which movement of a control input device in one or more of its degrees of freedom and/or selection of controls of the control input device can control selection of displayed options, e.g., in a graphical user interface displayed by display system 4220 and/or other display devices. A viewing mode can allow movement of control input devices to control a display provided from imaging devices (e.g., cameras), or movement of imaging devices, that may not be included in the slave device 4204. Control signals C1 to Cx can be used by the non-controlling mode module 4260 to control such elements (e.g., cursor, views, etc.) and control signals D1 to Dx can be determined by the non-controlling mode module to cause output of forces on the control input device(s) during such non-controlling modes, e.g., to indicate to the user interactions or events occurring during such modes.

Implementations described herein may be implemented, at least in part, by computer program instructions or code, which can be executed on a computer. For example, the code may be implemented by one or more digital processors (e.g., microprocessors or other processing circuitry). Instructions can be stored on a computer program product including a non-transitory computer readable medium (e.g., storage medium), where the computer readable medium can include a magnetic, optical, electromagnetic, or semiconductor storage medium including semiconductor or solid state memory, magnetic tape, a removable computer diskette, a random access memory (RAM), a read-only memory (ROM), flash memory, a rigid magnetic disk, an optical disk, a memory card, a solid-state memory drive, etc. The media may be or be included in a server or other device connected to a network such as the Internet that provides for the downloading of data and executable instructions. Alternatively, implementations can be in hardware (logic gates, etc.), or in a combination of hardware and software. Example hardware can be programmable processors (e.g. Field-Programmable Gate Array (FPGA), Complex Programmable Logic Device), general-purpose processors, graphics processors, Application Specific Integrated Circuits (ASICs), and the like.

Note that the functional blocks, operations, features, methods, devices, and systems described in the present disclosure may be integrated or divided into different combinations of systems, devices, and functional blocks as would be known to those skilled in the art.

Although the present implementations have been described in accordance with the examples shown, one of ordinary skill in the art will readily recognize that there can be variations to the implementations and those variations would be within the scope of the present disclosure. Accordingly, many modifications may be made by one of ordinary skill in the art without departing from the scope of the appended claims.

What is claimed is:

1. A control unit comprising:
   a first support;
   a second support coupled to the first support, wherein the second support is linearly translatable along a first axis in a first degree of freedom with respect to the first support, and at least a portion of the second support is linearly translatable along a second axis in a second degree of freedom with respect to the first support;
   a display unit rotatably coupled to the second support, wherein the display unit is rotatable about a third axis in a third degree of freedom with respect to the second support; and
   a first actuator, a second actuator, and a third actuator, wherein the first actuator is configured to output first forces on the display unit in the first degree of freedom, the second actuator is configured to output second forces on the display unit in the second degree of freedom, and the third actuator is configured to output third forces on the display unit in the third degree of freedom,
   wherein the display unit is rotatable about a defined pivot axis based on a coordinated combination of linear translation of the second support in the first degree of freedom, linear translation of at least the portion of the second support in the second degree of freedom, and rotation of the display unit in the third degree of freedom,
   wherein the first actuator, the second actuator, and the third actuator are configured to output the first forces, the second forces, and the third forces in combination to cause rotation of the display unit about the defined pivot axis,
   wherein the defined pivot axis does not correspond to an axis of rotation of any mechanical joint of the control unit, and
   wherein the defined pivot axis is configured to intersect a portion of a user operating the display unit or intersect a portion of the display unit.

2. The control unit of claim 1, wherein:
   the first support includes a first telescoping base portion and a second telescoping base portion,
   the second telescoping base portion is linearly translatable along the first axis with respect to the first telescoping base portion,
   the second support includes a first telescoping arm portion and a second telescoping arm portion,
   the second telescoping arm portion is linearly translatable along the second axis with respect to the first telescoping arm portion, and
   the second telescoping base portion of the first support is rigidly coupled to the first telescoping arm portion of the second support.

3. The control unit of claim 1, wherein:
   the second support is coupled to the first support by a middle support,
   the middle support includes a horizontal portion coupled rigidly to a vertical portion, the horizontal portion and the vertical portion being orthogonal to each other,
   the second support is horizontally translatable in the second degree of freedom with respect to the middle support, and
   the middle support and the second support are vertically translatable in the first degree of freedom with respect to the first support.

4. The control unit of claim 1, wherein:
   the display unit includes a tilt member rotatably coupled to an end of the second support,
   the tilt member rotatable about the third axis in the third degree of freedom, and
   the third axis is orthogonal to the first axis and to the second axis.

5. The control unit of claim 4, wherein:
   the display unit is rotatable about a fourth axis with respect to the tilt member in a fourth degree of freedom, and
   the fourth axis is orthogonal to the third axis.

6. The control unit of claim 4, further comprising:
   an actuator configured to output a force on the display unit about a fourth axis in a fourth degree of freedom; and
   a curved track coupled to the tilt member, wherein the display unit is coupled to the curved track, wherein the display unit, the curved track, and the tilt member are rotatable about the third axis in the third degree of freedom with respect to the second support, wherein the display unit is guided by the curved track to be rotatable with respect to the tilt member about the fourth axis in the fourth degree of freedom, and wherein the fourth axis is a yaw axis.

7. The control unit of claim 1, wherein:
the portion of the second support includes a yoke portion including two yoke members, and
the display unit is rotatably coupled to the two yoke members and is positioned between the two yoke members.

8. The control unit of claim 4, wherein a first end of the tilt member is coupled to an end of the second support, wherein the tilt member rotates within a rotatable range in which the tilt member linearly extends from the first end of the tilt member toward the first support to a second end of the tilt member, wherein the display unit is coupled to the second end of the tilt member.

9. The control unit of claim 1, wherein the first actuator, the second actuator, and the third actuator are configured to output the first forces, the second forces, and the third forces in combination to cause rotation of the display unit about the defined pivot axis to follow movement of a head of a user that operates the control unit.

10. The control unit of claim 1, wherein the display unit includes:
a hand input device provided on the display unit and configured to receive hand input from a hand of the user, wherein the hand input includes commands that cause the hand input device to output control signals to cause the actuators to move the display unit in a workspace of the display unit about the defined pivot axis.

11. The control unit of claim 1, wherein the control unit is coupled to a device including a control input device manipulable by a user to control one or more functions of a teleoperated manipulator system, wherein the one or more functions include causing an actuator of the teleoperated manipulator system to move an image capture device of the teleoperated manipulator system in accordance with manipulation of the control input device, wherein image data is received from the image capture device and displayed by the display unit.

12. The control unit of claim 1, wherein the display unit includes a head input device provided on the display unit and configured to receive head input via contact of a head of the user with the head input device, wherein the head input includes commands to move the display unit in a workspace of the display unit about the defined pivot axis.

13. The control unit of claim 1, wherein:
the defined pivot axis is positioned at a location such that the defined pivot axis extends through a neck of a user when the user operates the display unit;
the defined pivot axis extends through a hand input device provided on the display unit;
the defined pivot axis extends through a head input device provided on the display unit at a point on the head input device that is configured to contact a forehead of a user that operates the head input device; or
the defined pivot axis is coincident with an eye axis extending through the eyes of the user that operates the display unit.

14. The control unit of claim 1, wherein:
the defined pivot axis is configured to intersect a portion of the display unit.

15. A control unit comprising:
a support mechanism including:
a support linkage including a plurality of links including a first support and a second support;
a display unit coupled to the support linkage, wherein the display unit is moveable in multiple degrees of freedom based on relative movement between the plurality of links, wherein the multiple degrees of freedom include a linear first degree of freedom, a linear second degree of freedom, and a rotational third degree of freedom, wherein the display unit is rotatable about a defined pivot axis based on a coordinated combination of movement including linear translation of the second support in the first degree of freedom, linear translation of at least a portion of the second support in the second degree of freedom, and rotation of the display unit in the third degree of freedom; and
a plurality of actuators coupled to the support linkage; and
a control system in communication with the support mechanism and configured to provide control signals to the plurality of actuators to cause the display unit to rotate about a defined pivot axis, wherein the rotation about the defined pivot axis results from a coordinated combination of movement of the display unit in the linear first degree of freedom, the linear second degree of freedom, and the rotational third degree of freedom, wherein the defined pivot axis does not correspond to an axis of rotation of any mechanical joint of the control unit, and wherein the defined pivot axis is configured to intersect a portion of a user operating the display unit or intersect a portion of the display unit.

16. The control unit of claim 15, wherein the defined pivot axis is a horizontal axis aligned with an axis extending through a portion of a hand input device provided on the display unit, wherein the hand input device is configured to be operated by a hand of the user operating the display unit and the hand input device, wherein the hand input device is operable to receive hand input from the hand of the user, wherein the hand input includes commands that cause the hand input device to output control signals to cause the actuators to move the display unit in a workspace of the display unit about the defined pivot axis.

17. The control unit of claim 15, wherein:
the defined pivot axis is a horizontal axis extending through a neck of a user that operates the display unit;
the defined pivot axis is a horizontal axis aligned with an axis extending through the eyes of the user that operates the display unit; or
the defined pivot axis is a horizontal axis aligned with an axis extending through a portion of an input device provided on the display unit, wherein the portion of the input device is configured to contact a forehead of the user that operates the display unit.

18. The control unit of claim 15, wherein the defined pivot axis is adjustable in space based on user input to the control unit that defines a location of the defined pivot axis.

19. The control unit of claim 15, wherein the control system is configured to provide the control signals to control the actuators to move the display unit about the defined pivot axis to follow movement of a head of a user that operates the control unit.

20. A method comprising:
determining a defined pivot axis for a display unit;
receiving first user input at a first input device; and causing movement of the display unit in one or more degrees of freedom provided by a support linkage coupled to the display unit, wherein the movement is based on the first user input, wherein causing the movement includes:
   controlling a first actuator to cause a second link of the support linkage to linearly translate with respect to a first link of the support linkage along a first axis in a first degree of freedom;
   controlling a second actuator to cause a portion of the second link to linearly translate with respect to the first link along a second axis in a second degree of freedom; and
   controlling a third actuator to cause the display unit to rotate about a third axis in a third degree of freedom with respect to the second link,
   wherein the first actuator, the second actuator, and the third actuator are controlled to cause a coordinated combination of linear translation in the first degree of freedom, linear translation in the second degree of freedom, and rotation of the display unit in the third degree of freedom to cause the display unit to rotate about the defined pivot axis,
   wherein the defined pivot axis does not correspond to an axis of rotation of any mechanical joint of the support linkage and the display unit, and
   wherein the defined pivot axis is configured to intersect a portion of a user operating the display unit or intersect a portion of the display unit.

* * * * *